(12) United States Patent
Cho et al.

(10) Patent No.: US 10,874,335 B2
(45) Date of Patent: Dec. 29, 2020

(54) WEARABLE ELECTRONIC DEVICE

(71) Applicants: Chul-Ho Cho, Gyeonggi-do (KR);
Seong-Wook Jo, Gyeonggi-do (KR);
Seung-Min Lee, Seoul (KR);
Jea-Hyuck Lee, Gyeonggi-do (KR);
Seong-Je Cho, Gyeonggi-do (KR);
Jae-Geol Cho, Gyeonggi-do (KR);
Sun-Tae Jung, Gyeonggi-do (KR)

(72) Inventors: Chul-Ho Cho, Gyeonggi-do (KR);
Seong-Wook Jo, Gyeonggi-do (KR);
Seung-Min Lee, Seoul (KR);
Jea-Hyuck Lee, Gyeonggi-do (KR);
Seong-Je Cho, Gyeonggi-do (KR);
Jae-Geol Cho, Gyeonggi-do (KR);
Sun-Tae Jung, Gyeonggi-do (KR)

(73) Assignee: Samsung Electronics Co., Ltd

(*) Notice: Subject to any disclaimer, the term of this patent is extended or adjusted under 35 U.S.C. 154(b) by 519 days.

(21) Appl. No.: 15/081,084

(22) Filed: Mar. 25, 2016

(65) Prior Publication Data
US 2016/0278672 A1  Sep. 29, 2016

Related U.S. Application Data

(60) Provisional application No. 62/138,086, filed on Mar. 25, 2015.

(30) Foreign Application Priority Data

Aug. 21, 2015 (KR) .................. 10-2015-0118207
Jan. 26, 2016 (KR) .................. 10-2016-0009537

(51) Int. Cl.
*A61B 5/00* (2006.01)
*A61B 5/145* (2006.01)
(Continued)

(52) U.S. Cl.
CPC ........ *A61B 5/14532* (2013.01); *A61B 5/1473* (2013.01); *A61B 5/1477* (2013.01);
(Continued)

(58) Field of Classification Search
CPC ....... A61B 5/15; A61B 5/685; A61B 5/14532; A61B 5/14546; A61B 5/6802;
(Continued)

(56) References Cited

U.S. PATENT DOCUMENTS 6,275,717 B1 * 8/2001 Gross ................. A61B 5/14865
600/309
7,942,831 B2 * 5/2011 Sawa ................. A61B 5/14514
600/345

(Continued)

FOREIGN PATENT DOCUMENTS

CN   101036575   9/2007
CN   101061953   10/2007
(Continued)

OTHER PUBLICATIONS

International Search Report dated Jun. 22, 2016 issued in counterpart application No. PCT/KR2016/003056, 10 pages.
(Continued)

*Primary Examiner* — Jacqueline Cheng
*Assistant Examiner* — Tho Q Tran
(74) *Attorney, Agent, or Firm* — The Farrell Law Firm, P.C.

(57) ABSTRACT

Disclosed is a wearable electronic device including a body portion wearable on a human body, a circuit portion mounted on the body portion, and a sensor portion contacting the human body to measure a bio signal, wherein the sensor portion is detachably coupled to the body portion.

19 Claims, 56 Drawing Sheets

(51) Int. Cl.
*A61B 5/1486* (2006.01)
*A61B 5/15* (2006.01)
*A61B 5/1473* (2006.01)
*A61B 5/1477* (2006.01)

(52) U.S. Cl.
CPC ........ *A61B 5/1486* (2013.01); *A61B 5/14546* (2013.01); *A61B 5/15* (2013.01); *A61B 5/6802* (2013.01); *A61B 5/685* (2013.01); *A61B 5/6814* (2013.01); *A61B 5/6824* (2013.01); *A61B 2560/0204* (2013.01); *A61B 2560/045* (2013.01); *A61B 2562/043* (2013.01)

(58) Field of Classification Search
CPC ... A61B 5/1486; A61B 5/1477; A61B 5/1473; A61B 2562/043; A61B 2560/0204; A61B 2560/045; A61B 5/6824; A61B 5/6814
See application file for complete search history.

(56) References Cited

U.S. PATENT DOCUMENTS

| | | | |
|---|---|---|---|
| 8,721,544 | B2 | 5/2014 | Roesicke et al. |
| 2002/0022855 | A1 | 2/2002 | Bobroff et al. |
| 2002/0072103 | A1* | 6/2002 | Matsumoto ............ C12Q 1/001 435/200 |
| 2002/0180605 | A1 | 12/2002 | Ozguz et al. |
| 2004/0133164 | A1 | 7/2004 | Funderburk et al. |
| 2005/0154273 | A1 | 7/2005 | Lee et al. |
| 2005/0159678 | A1 | 7/2005 | Tanlike et al. |
| 2006/0016700 | A1* | 1/2006 | Brister ............... A61B 5/14532 205/777.5 |
| 2007/0197889 | A1 | 8/2007 | Mister et al. |
| 2007/0208241 | A1* | 9/2007 | Drucker ................. A61B 5/00 600/323 |
| 2007/0219436 | A1 | 9/2007 | Takase et al. |
| 2007/0232875 | A1 | 10/2007 | Maekawa et al. |
| 2008/0021290 | A1 | 1/2008 | Sawa et al. |
| 2011/0020852 | A1* | 1/2011 | Kojima ............... A61B 5/14532 435/14 |
| 2011/0184264 | A1* | 7/2011 | Galasso ............. A61B 5/14532 600/347 |
| 2011/0288574 | A1* | 11/2011 | Curry ................. A61B 5/14503 606/185 |
| 2012/0116190 | A1 | 5/2012 | Iketani et al. |
| 2012/0130214 | A1 | 5/2012 | Brister et al. |
| 2012/0172693 | A1 | 7/2012 | Borlah et al. |
| 2013/0053669 | A1 | 2/2013 | Yob et al. |
| 2013/0150691 | A1* | 6/2013 | Pace .................. A61B 5/14532 600/347 |
| 2014/0336487 | A1* | 11/2014 | Wang .................... A61B 5/685 600/352 |
| 2015/0028097 | A1 | 1/2015 | Lee et al. |

FOREIGN PATENT DOCUMENTS

| | | |
|---|---|---|
| CN | 100539937 | 9/2009 |
| CN | 104518273 | 4/2015 |
| EP | 1 834 589 | 9/2007 |
| EP | 1552785 | 8/2012 |
| IE | 970443 | 12/1998 |
| KR | 1020150012879 | 2/2015 |
| WO | WO 96/14026 | 5/1996 |
| WO | WO 2004/052192 | 6/2004 |
| WO | WO 2013/058879 | 4/2013 |

OTHER PUBLICATIONS

European Search Report dated Jul. 13, 2018 issued in counterpart application No. 16769131.0-1115, 16 pages.
European Search Report dated Feb. 22, 2018 issued in counterpart application No. 16769131.0-1115, 15 pages.
Chinese Office Action dated Nov. 1, 2019 issued in counterpart application No. 201680018118.4, 14 pages.

* cited by examiner

WEARABLE ELECTRONIC DEVICE

PRIORITY

This application claims priority under 35 U.S.C. § 119(a) to a U.S. Provisional Application filed in the United States Patent and Trademark Office on Mar. 25, 2015 and assigned Ser. No. 62/138,086, a Korean Patent Application filed in the Korean Intellectual Property Office on Aug. 21, 2015 and assigned Serial No. 10-2015-0118207, and a Korean Patent Application filed in the Korean Intellectual Property Office on Jan. 26, 2016 and assigned Serial No. 10-2016-0009537, the contents of each which are incorporated herein by reference.

BACKGROUND

1. Field of the Disclosure

The present disclosure relates generally to electronic devices, and more particularly, to electronic devices that are wearable a portion of a human body.

2. Description of the Related Art

Various biomarkers, such as glucose, are present in the human blood. A biomarker is a body substance by which a symptom or phenomenon shown in the human body may be measured.

Carbohydrates in food are dissolved into glucose via digestion. Glucose, which is referred to as blood sugar in the blood, is a basic energy source to the human body that is used in various tissues including brain, muscles, and fat and is delivered to various tissues through blood. Blood sugar levels increase after a meal, decrease on an empty stomach, and remain within a constant range with mutual actions by hormones including insulin or glucagon secreted from the pancreas. As blood sugar levels increase, insulin suppresses the new production of glucose from the liver while increasing the use of glucose in the muscles or fat tissues to reduce blood sugar. In contrast, as blood sugar levels decrease, more glucagon secretion occurs to allow the liver to produce more glucose, leading to an increased blood sugar level.

The increase or departure of blood sugar levels from a normal range is called diabetes, a type of a metabolic disease. A diabetic patient may be vulnerable to polyuria, polydipsia infection, abnormal vision due to microvascular complications, abnormal kidney function, peripheral neuritis, foot ulcers, dysfunction in the autonomic nervous system and its relevant symptoms in the digestive system, urogenital system or cardiovascular system. To adjust the blood sugar of diabetic patients, an oral medication or shot including an insulin secretagogue may be used to inject insulin into the human body. The amount of the oral medication or insulin is adjusted according to the blood sugar level of the diabetic patient. For accurate verification of his blood sugar level, a diabetic patient periodically measures his blood sugar level using a glucometer.

For easier measurement, the glucometer needs to be made compact, lightweight, and easily portable.

In measuring the blood sugar level of a diabetic patient using a glucometer, referred to as self-blood sugar reading, a lancet is used to collect blood from the finger and a strip sensor and reader are used to measure the blood sugar level from the collected blood. This tends to subject the patient to substantial pain as it requires the patient to use the lancet for measurement several times per day.

For minimized pain, blood sugar measurement patches have been introduced, which use micro needles with a diameter of a few tens of micrometers that are inserted into the skin and remain attached to the skin for a predetermined period of time to extract a body fluid. A blood sugar measurement patch using micro needles includes a circuit part for measuring the blood sugar level of the collected blood and a battery. Due to the limited durability of the micro needles, however, the entire patch including the circuit portion and battery are disposed of after the lifetime of the patch.

As such, there is a need in the art for a method and apparatus that promotes continuous use of components of the wearable patch.

SUMMARY

The present disclosure has been made to address the above-mentioned problems and disadvantages, and to provide at least the advantages described below. Accordingly, an aspect of the present disclosure is to provide a wearable electronic device having some replaceable parts, such as micro needles, and other parts that may be continuously used, such as a battery, detachably coupled with each other.

Another aspect of the present disclosure is to provide a wearable electronic device having an exchangeable sensor detecting a biomarker, such as lactic acid, body temperature, or blood pressure, as well as blood sugar level.

According to an aspect of the present disclosure, a wearable electronic device includes a main body wearable on a human body, a circuit unit mounted on the body unit, and a receiving unit provided in the main body and receiving a sensor unit contacting the human body to measure a bio signal, wherein the sensor unit is detachably coupled to the body unit.

According to another aspect of the present disclosure, a wearable electronic device includes a main body wearable on a human body, and a sensor unit provided in the main body and contacting a human body to measure a bio signal, wherein the sensor unit includes a working electrode, a counter electrode electrically connected with the working electrode, and a reference electrode electrically connected with the working electrode, and wherein the sensor unit measures the bio signal by varying a voltage between the reference electrode and the working electrode.

According to another aspect of the present disclosure, a wearable electronic device includes a main body wearable on a human body, a sensor unit provided in the main body and including micro needles, and an attaching device attaching the sensor unit to a human body, wherein the attaching device includes a housing, a moving unit that moves back and forth in the housing, a hooking unit provided in the housing and detachably coupled with the moving unit, a first elastic unit provided between the moving unit and the hooking unit to provide an elastic force to the moving unit, a button unit that releases a coupling between the hooking unit and the moving unit, a receiving unit provided in the moving unit and receiving the body unit, and a coupling unit provided in the moving unit and detachably coupled with the body unit.

BRIEF DESCRIPTION OF THE DRAWINGS

The above and other aspects, features, and advantages of the present disclosure will be more apparent from the following detailed description taken in conjunction with the accompanying drawings, in which.

Throughout the drawings, like reference numerals will be understood to refer to like parts, components, and structures.

DETAILED DESCRIPTION OF EMBODIMENTS OF THE DISCLOSURE

Figure 1:
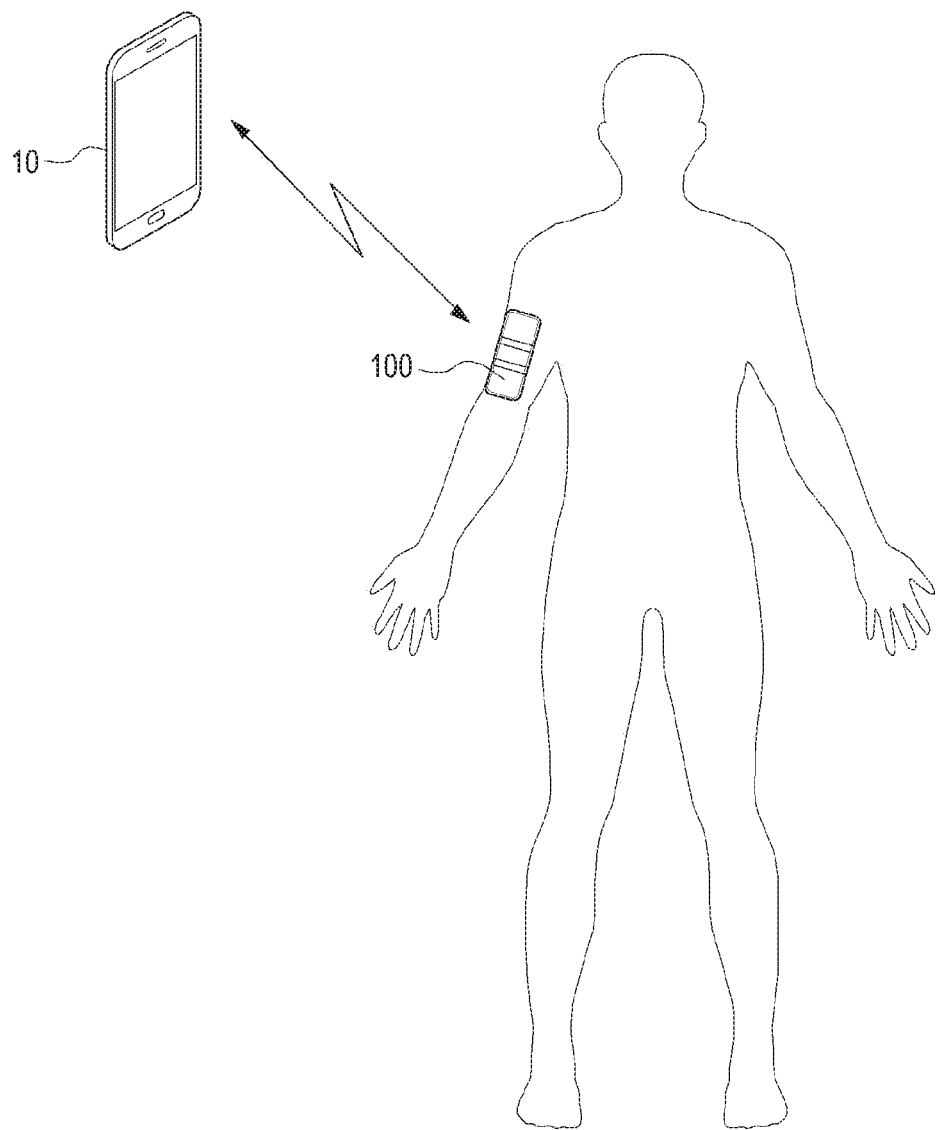
FIG. 1 illustrates a wearable device attached to a user's body according to an embodiment of the present disclosure.

Hereinafter, embodiments of the present disclosure are described with reference to the accompanying drawings. However, it should be appreciated that the present disclosure is not limited to the embodiments, and all changes and/or equivalents or replacements thereto also belong to the scope of the present disclosure. The same or similar reference denotations may be used to refer to the same or similar elements throughout the specification and the drawings. A description of known elements and/or configurations will be omitted for the sake of clarity and conciseness.

As used herein, the terms "have," "may have," "include," or "may include" a feature (such as a number, function, operation, or a component such as a part) indicate the existence of the feature and do not exclude the existence of other features.

As used herein, the terms "A or B," "at least one of A and/or B," or "one or more of A and/or B" include all possible combinations of A and B. For example, "A or B," "at least one of A and B," "at least one of A or B" refer to all of (1) including at least one A, (2) including at least one B, and (3) including at least one A and at least one B.

As used herein, the terms "first" and "second" modify various components regardless of importance and/or order and are used to distinguish a component from another component without limiting the components. For example, a first user device and a second user device indicate different user devices from each other regardless of the order or importance of the devices. A first component may be referred to as a second component, and vice versa without departing from the scope of the present disclosure.

It will be understood that when an element, such as a first element, is referred to as being operatively or communicatively "coupled with/to," or "connected with/to" another element, such as a second element, it can be coupled or connected with/to the other element directly or via a third element. In contrast, it will be understood that when a first element is referred to as being "directly coupled with/to" or "directly connected with/to" a second element, no third element intervenes between the first and second elements.

The terms as used herein are provided merely to describe some embodiments thereof, but not to limit the scope of other embodiments of the present disclosure. It is to be understood that the singular forms "a," "an," and "the" include plural references unless the context clearly dictates otherwise. The terms including technical and scientific terms used herein have the same meaning as commonly understood by one of ordinary skill in the art to which the embodiments of the present disclosure pertain. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some cases, the terms defined herein are not to be interpreted to exclude embodiments of the present disclosure.

Figure 2:
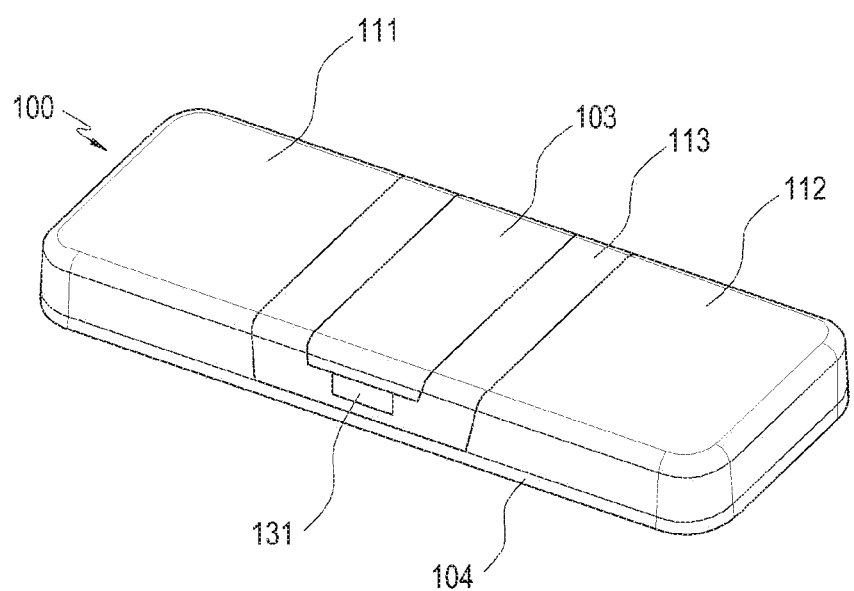
FIG. 2 is a front perspective view illustrating a wearable electronic device according to an embodiment of the present disclosure.
Figure 3:
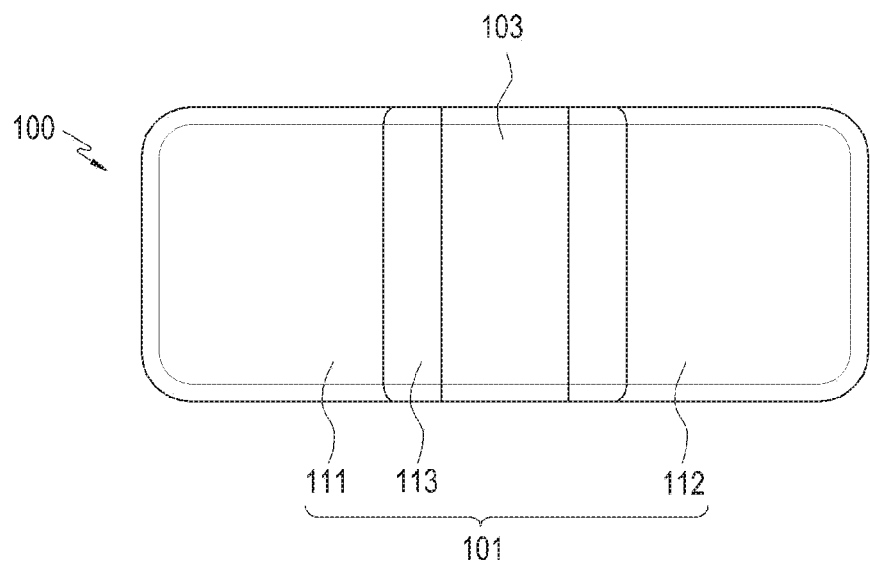
FIG. 3 is a front view illustrating a wearable electronic device according to an embodiment of the present disclosure.
Figure 4:
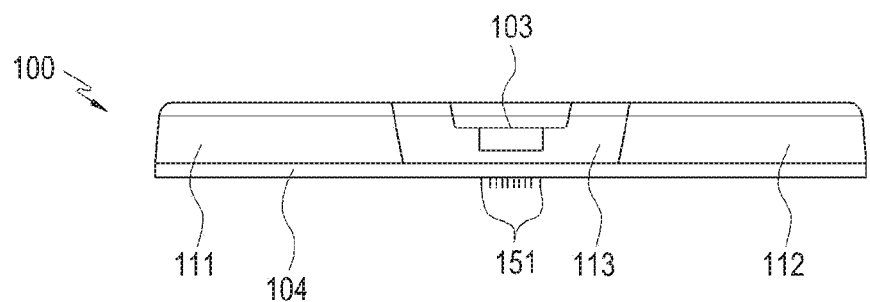
FIG. 4 is a side view illustrating a wearable electronic device according to an embodiment of the present disclosure.
Figure 5:
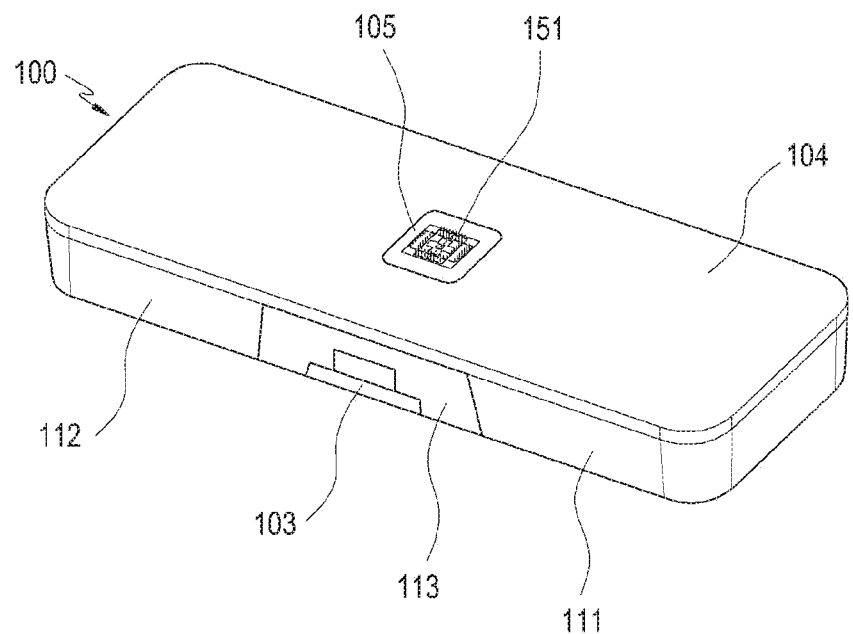
FIG. 5 is a rear perspective view illustrating a wearable electronic device according to an embodiment of the present disclosure.
Figure 6:
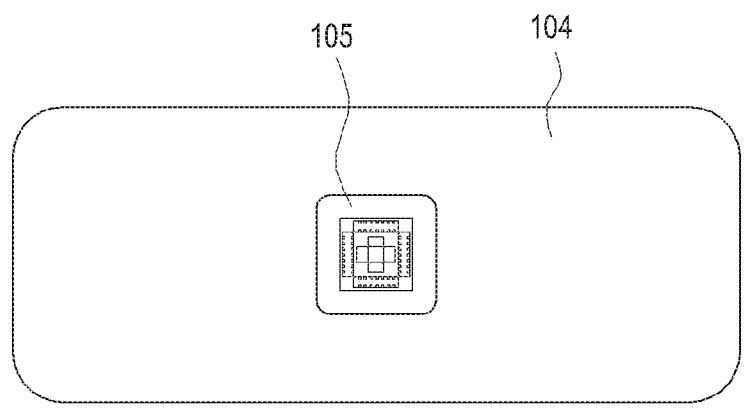
FIG. 6 is a rear view illustrating a wearable electronic device according to an embodiment of the present disclosure.

FIG. 1 illustrates a wearable device attached to a user's body according to an embodiment of the present disclosure. FIG. 2 is a front perspective view illustrating a wearable electronic device according to an embodiment of the present disclosure. FIG. 3 is a front view illustrating a wearable electronic device according to an embodiment of the present disclosure. FIG. 4 is a side view illustrating a wearable electronic device according to an embodiment of the present disclosure. FIG. 5 is a rear perspective view illustrating a wearable electronic device according to an embodiment of the present disclosure. FIG. 6 is a rear view illustrating a wearable electronic device according to an embodiment of the present disclosure.

Referring to FIGS. 1 to 6, the wearable electronic device 100 includes a main body 101 and a sensor unit 105.

The main body 101 includes a pad 104 on the rear surface of the main body 101 for placement on the user's body.

The pad 104 has an adhesive to allow the main body 101 to be worn on the user's body. The main body 101 may be separated from the user's body by an external force from the user.

The main body 101 includes a first main body 111 where a circuit unit is mounted, a second main body 112 where a battery is mounted, and a third main body 113 where the sensor unit 105 is mounted. A cover unit 103 is connected to the third main body 113 to open and close the inside of the third main body 113. The third main body 113 includes a button 131 to operate the cover unit 103. The third main body 113 is provided between the first main body 111 and the second main body 112 so that the sensor unit 105 mounted in the third main body 113 is disposed in a central area of the main body 101. As the sensor unit 105 is disposed in the central area of the main body 101, the pad 104 externally surrounds the sensor unit 105, allowing the sensor unit 105 to come in stable contact with the body skin. However, the sensor unit 105 is not limited as disposed in the central area of the main body 101, and thus may be disposed in another unit of the electronic device 100.

The sensor unit 105 contacts the body to detect a biomarker or to measure an electrical signal by the biomarker. Hereinafter, the electrical signal is referred to as a bio signal. For example, the sensor unit 105 includes micro needles 151 that are inserted into the body skin to collect a body fluid. When the micro needles 151 are inserted into the skin, the body fluid is delivered through the inside of the micro needles 151 to the sensor unit 105.

According to an embodiment of the present disclosure, the micro needles 151 are formed of conductive polymer and contain an enzyme that performs a chemical action with the body fluid. The conductive-polymer micro needles 151 receive an electric current to trigger a chemical action between the enzyme and the biomarker. The micro needles 151 measure the biomarker using an electrical signal generated by the chemical action, i.e., an electrical current.

The sensor unit 105 measures the concentration of glucose from the collected body fluid. However, the sensor unit 105 is not limited thereto, and detects various biomarkers such as lactic acid in the body fluid or measure a bio signal by the micro needle.

The circuit unit is electrically connected with the sensor unit 105 to receive a bio signal value measured by the sensor unit 105. The circuit unit includes a communication module to transmit the bio signal value to a separate electronic device 10. The communication module receives data from the separate electronic device 10, which stores the bio signal value received from the communication module or stores bio information analyzed via a separate algorithm or calculation using the bio signal value.

For example, an electrical signal value generated from a sensor by glucose in the blood, i.e., blood sugar which is a biomarker, corresponds to a bio signal value which is a blood sugar level, and high blood sugar or low blood sugar indicating whether the blood sugar level as compared with a standard value is relatively high or low corresponds to the bio information obtained by analyzing the bio signal. The separate electronic device 10 includes a display module to display the concentration of the biomarker, such as the concentration of the user's blood sugar or a relative numerical value. The separate electronic device 10 includes a display device to display a graph or statistical rendition of bio signal values by the biomarker received from the wearable electronic device 100, so that the user may hourly or daily identify the variation in concentration of the biomarker.

Figure 7:
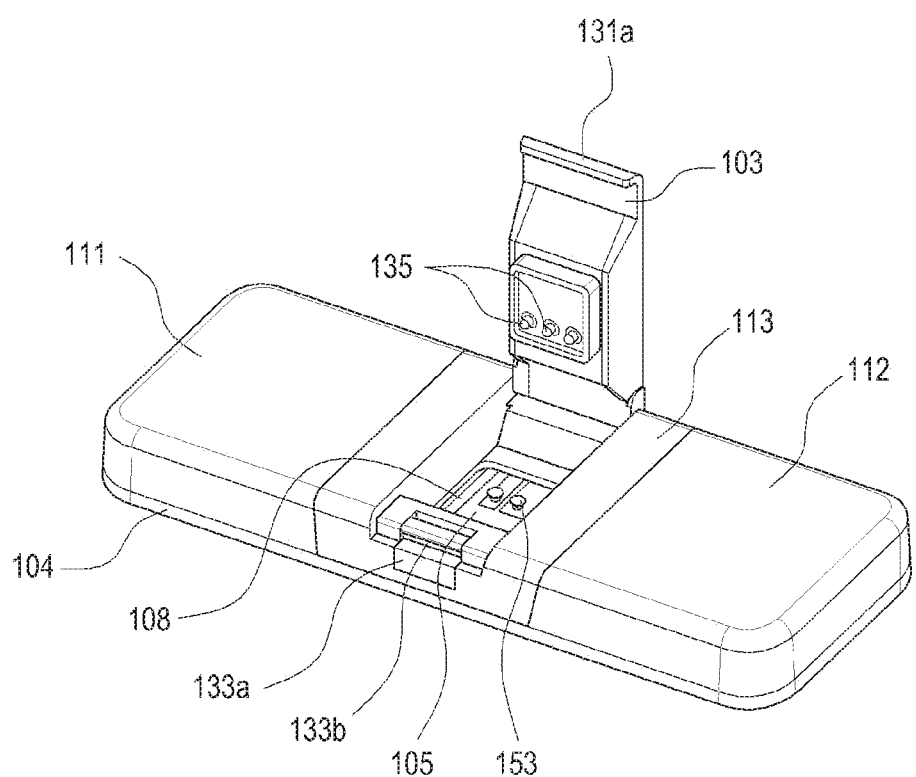
FIG. 7 is a front perspective view illustrating a wearable electronic device with a cover unit opened according to an embodiment of the present disclosure.
Figure 8:
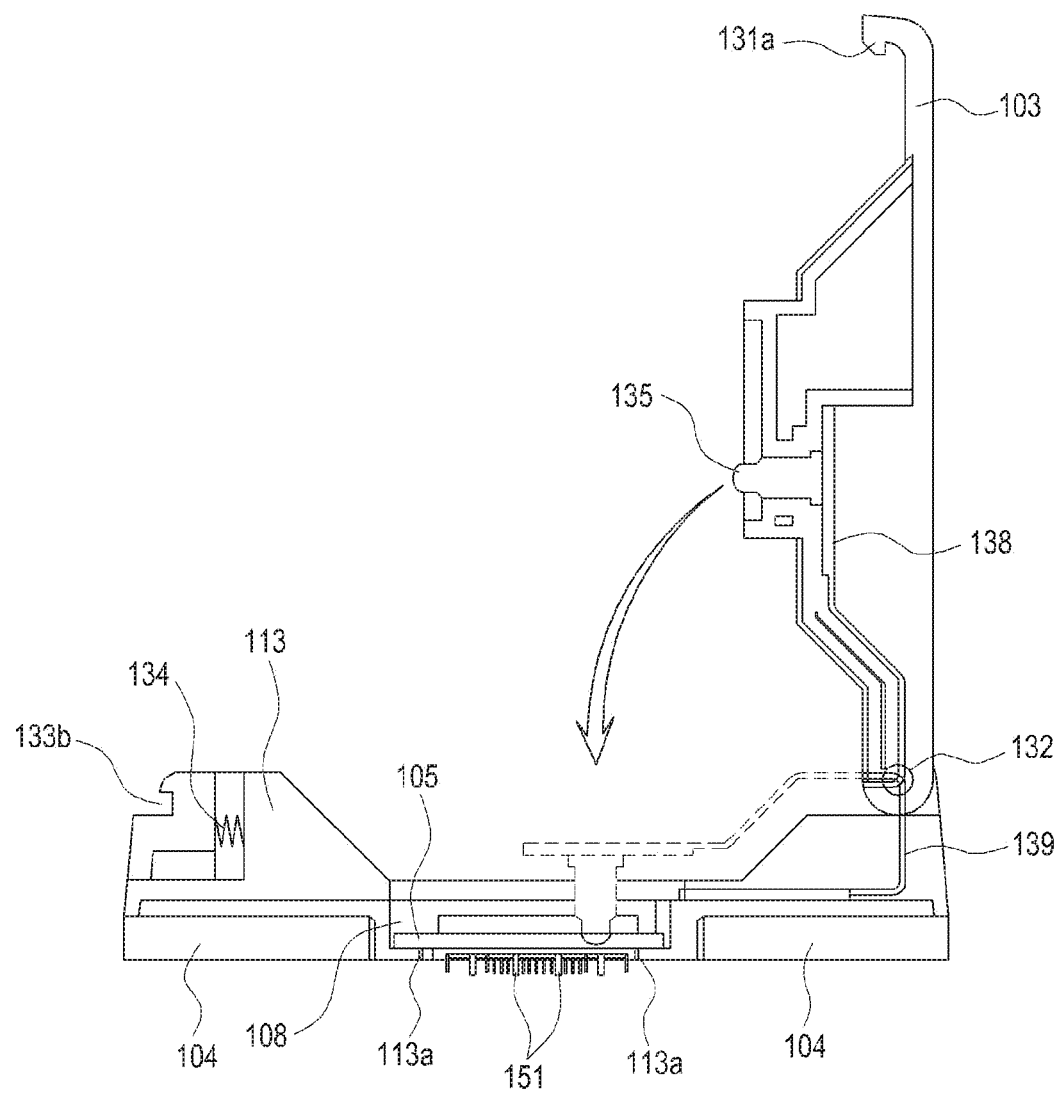
FIG. 8 is a cross-sectional view illustrating a wearable electronic device with a cover unit opened according to an embodiment of the present disclosure.
Figure 9:
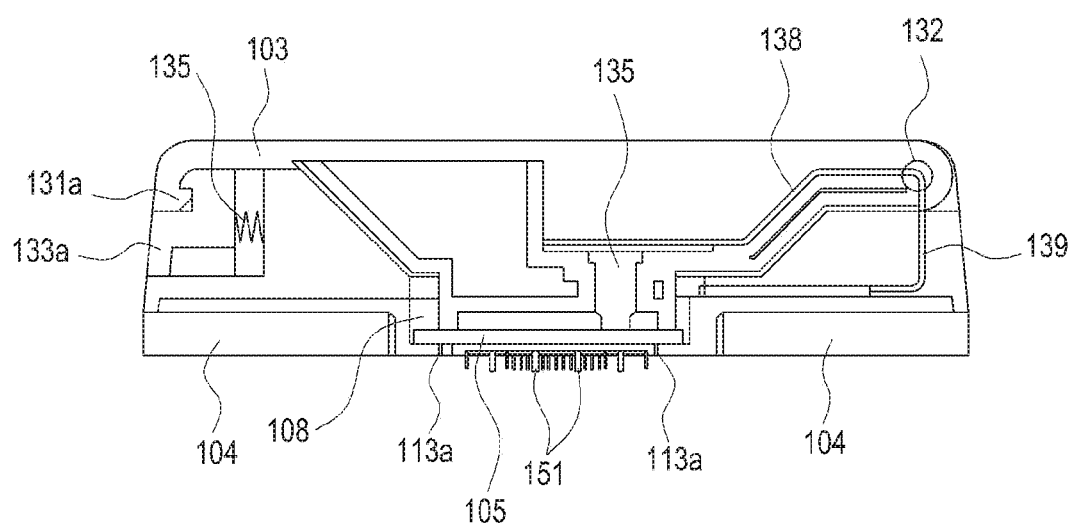
FIG. 9 is a cross-sectional view illustrating a wearable electronic device with a cover unit closed according to an embodiment of the present disclosure.

FIG. 7 is a front perspective view illustrating a wearable electronic device with a cover unit opened according to an embodiment of the present disclosure. FIG. 8 is a cross-sectional view illustrating a wearable electronic device with a cover unit opened according to an embodiment of the present disclosure. FIG. 9 is a cross-sectional view illustrating a wearable electronic device with a cover unit closed according to an embodiment of the present disclosure.

Referring to FIGS. 7 to 9, the wearable electronic device includes a receiving unit for receiving the sensor unit 105 and a cover unit 103 for fastening the sensor unit 105.

The receiving unit is provided in the third main body 113 to provide a space where the sensor unit 105 is received. The sensor unit 105 may be mounted or separated from a space opened to the front of the third main body 113 to the receiving unit. The receiving unit includes an opening where a unit of the rear surface of the sensor unit, such as where the micro needles 151 are arranged, is exposed to the outside of the third main body 113 and a seating unit 113a where another unit of the rear surface of the sensor unit 105, such as an edge of the sensor unit 105, is seated.

The opening passes through the rear surface of the third main body 113 so that the micro needles 151 are projected from the rear surface of the third main body 113. The seating unit 113*a* extends from the third main body 113 to the opening to partially close the opening. The rear surface of the seating unit 113*a* is formed to be disposed on the same plane as the rear surface of the pad 104 to allow the rear surface of the seating unit 113*a* to contact the user's skin. However, the rear surface of the seating unit 113*a* is not limited thereto, and may be disposed on a different plane than the rear surface of the pad 104.

The sensor unit 105 is seated on the seating unit 113*a* through the front surface of the third button unit 113, and the micro needles 115 are projected from the rear surface of the main body 113 through the opening to be inserted into the body skin.

The cover unit 103 fastens the sensor unit 105 received in the receiving unit while covering the front surface of the third main body 113. The front surface of the cover unit 103 is generally on the same plane as the front surface of the first main body 111 and the second main body 112. The cover unit 103 includes a hinge unit 132 hinged to the third main body 113 to rotate about the third main body 113, so as to cover or to open the front surface of the receiving unit. As the cover unit 103 rotates to cover the front surface of the third main body 113, the sensor unit 105 is received in or separated from the receiving unit through the front surface of the main body 113 to be replaced with other sensor unit 105. In contrast, as the cover unit 103 rotates to cover the front surface of the receiving unit, the cover unit 103 fastens the sensor unit 105 to the receiving unit while pressing the front surface of the sensor unit 105 received in the receiving unit.

The cover unit 103 includes a hooking unit 131*a* that extends and projects from an end of the cover unit 103. The main body 113 includes a button 133*a* with a hooking hole 133*b* where the hooking unit 131*a* is inserted. As the hooking unit 131*a* is inserted and fastened to the hooking hole 131*b*, the cover unit 103 is coupled with the third main body 113 while covering the front surface of the receiving unit. The third main body 113 includes an elastic unit 134, such as a spring, which is provided between the button 133*a* and the third main body 133 to provide an elastic force. As the button 133*a* presses the elastic unit by an external force from the user, the hooking unit 131*a* fastened to the hooking hole 133*b* may be released, and thus, the coupling between the cover unit 103 and the third main body 113 may be released, opening the front surface of the receiving unit.

The cover unit 103 includes contact terminals 135 electrically connected with the sensor unit 105. The contact terminals 135 connect to their respective contact pads 153 of the sensor unit 105, providing a path through which the electrical signal for the biomarker measured by the sensor unit 105 is transferred to the circuit unit. The cover unit 103 includes a first circuit board 138 provided between the contact terminals 135 and the circuit unit to allow an electrical signal to flow therethrough. For example, the sensor unit 105 is electrically connected with the circuit unit sequentially passing through the contact pads 153, the contact terminals 135, and the first circuit board 138.

The contact terminals 135 transfer current from the circuit unit to the sensor unit 105 and include an elastic force allowing the contact terminals 135 to be extended or contracted along a longitudinal direction of the contact terminals 135. For example, the contact terminals 135 may be pogo pins. The contact terminals 135, as coupled to the third cover unit 113 with the cover unit 103 covering the receiving unit, may be pressurized abutting the contact pads 153 of the sensor unit 105. As the contact terminals 135 are contracted, the contact terminals 135 remains in contact with the contact pads 153.

As such, as the sensor unit 105 is received in the receiving unit and fastened by the cover unit 103 or is removed from the receiving unit as the cover unit 103 rotates, the sensor unit 105 may be replaced from the main body when necessary, while the circuit unit and battery in the main body may be continuously used along with the exchanged sensor unit 105.

Figure 10:
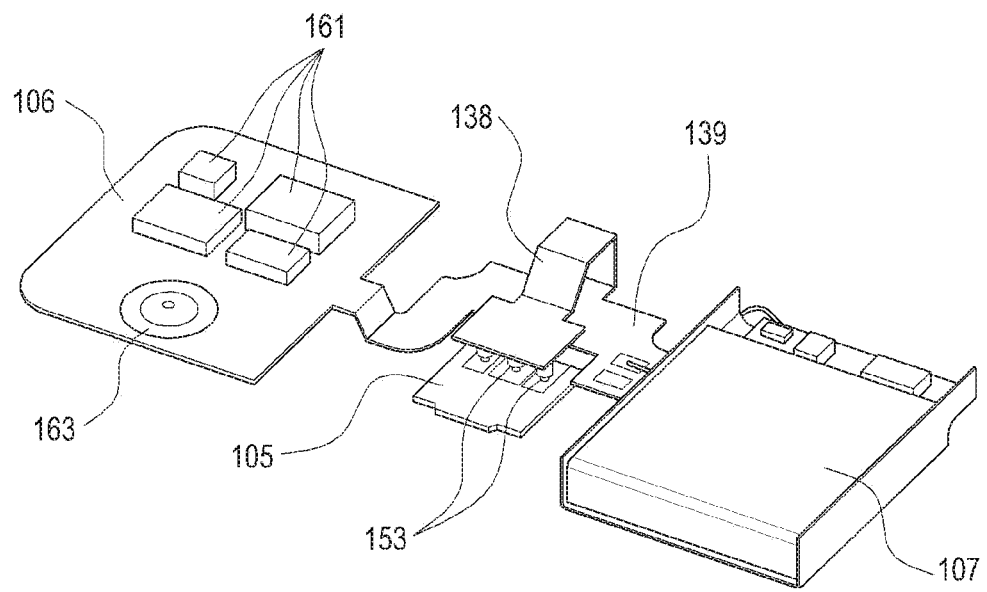
FIG. 10 is a front perspective view illustrating a circuit unit, sensor unit, and battery of a wearable electronic device according to an embodiment of the present disclosure.
Figure 11:
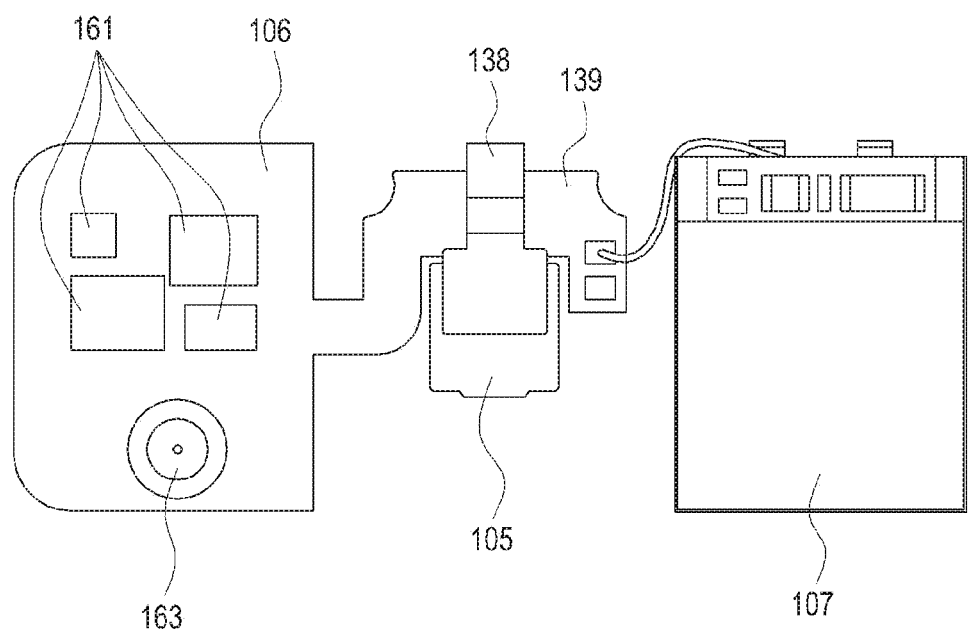
FIG. 11 is a front view illustrating a circuit unit, sensor unit, and battery of a wearable electronic device according to an embodiment of the present disclosure.
Figure 12:
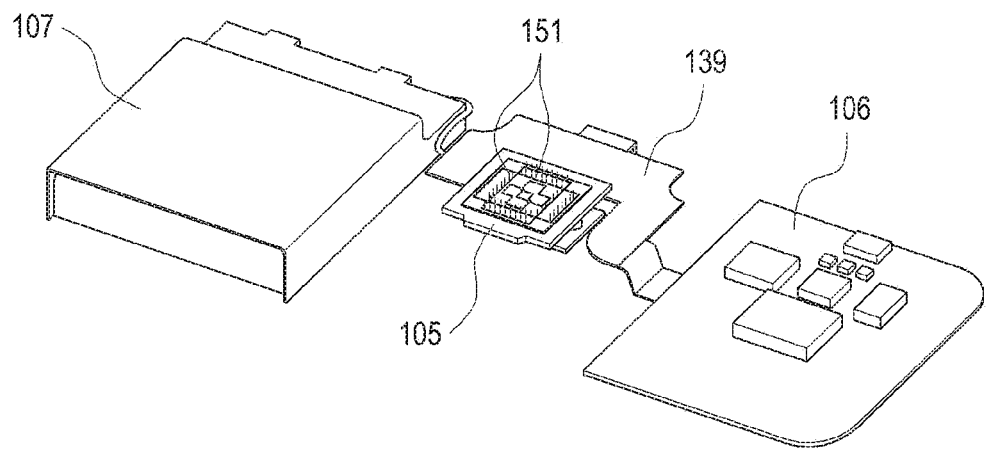
FIG. 12 is a rear perspective view illustrating a circuit unit, sensor unit, and battery of a wearable electronic device according to an embodiment of the present disclosure.
Figure 13:
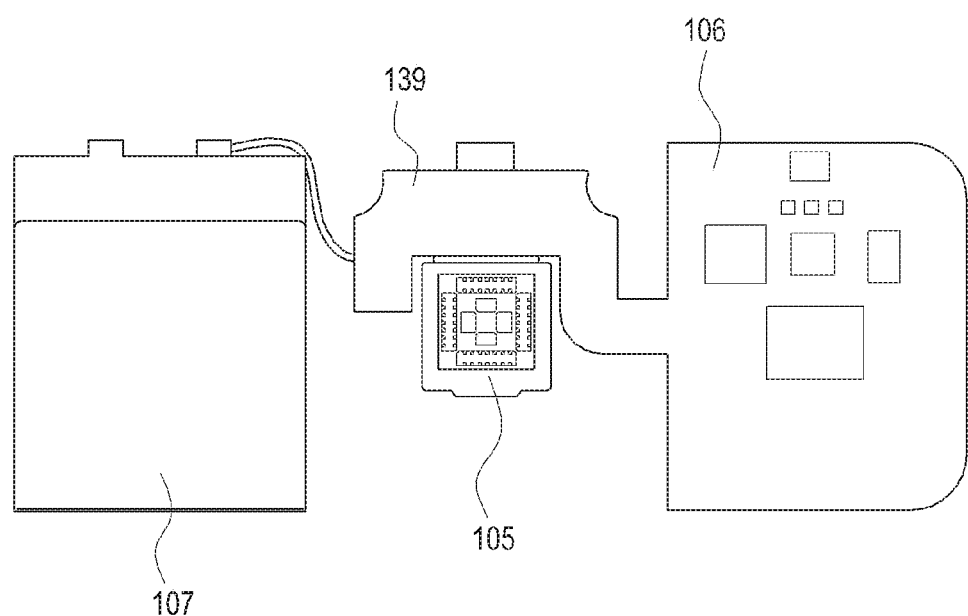
FIG. 13 is a rear view illustrating a circuit unit, sensor unit, and battery of a wearable electronic device according to an embodiment of the present disclosure.

FIG. 10 is a front perspective view illustrating a circuit unit, sensor unit, and battery of a wearable electronic device according to an embodiment of the present disclosure. FIG. 11 is a front view illustrating a circuit unit, sensor unit, and battery of a wearable electronic device according to an embodiment of the present disclosure. FIG. 12 is a rear perspective view illustrating a circuit unit, sensor unit, and battery of a wearable electronic device according to an embodiment of the present disclosure. FIG. 13 is a rear view illustrating a circuit unit, sensor unit, and battery of a wearable electronic device according to an embodiment of the present disclosure.

Referring to FIGS. 10 to 13, the wearable electronic device includes a second circuit board 139 connected with the circuit unit 106.

The circuit unit 106 includes various electronic parts 161, such as a main chipset, communication module, power supplying unit, and storage unit, mounted thereon. The main chipset receives an electrical signal for a biomarker measured by the sensor unit 105. The sensor unit 105 controls various electronic parts including the communication module, power supplying unit, and storage unit. The communication module communicates bio signals by the biomarker or communicate values by the bio signals, i.e., bio signal values under the control of the main chipset. The power supplying unit stably supplies current to the sensor unit 105 under the control of the main chipset. The storage unit stores the bio signal values under the control of the main chipset. The circuit unit 106 includes a switch 163 that turns on/off the wearable electronic device.

The second circuit board 139 is provided between the circuit unit 106 and the battery 107 to supply power from the battery 107 to the circuit unit 106. The second circuit board 139 is connected with the first circuit board 138 to be electrically connected with the sensor unit 105 via the contact terminals connected with the first circuit board 138.

According to an embodiment of the present disclosure, a method for manufacturing a wearable electronic device includes preparing the second circuit board 139 so that the circuit unit 106, the sensor unit 105, and the battery 107 are electrically connected with one another while the sensor unit 105 is disposed between the circuit unit 106 and the battery 107, as shown in FIGS. 10 to 13.

Figure 14:
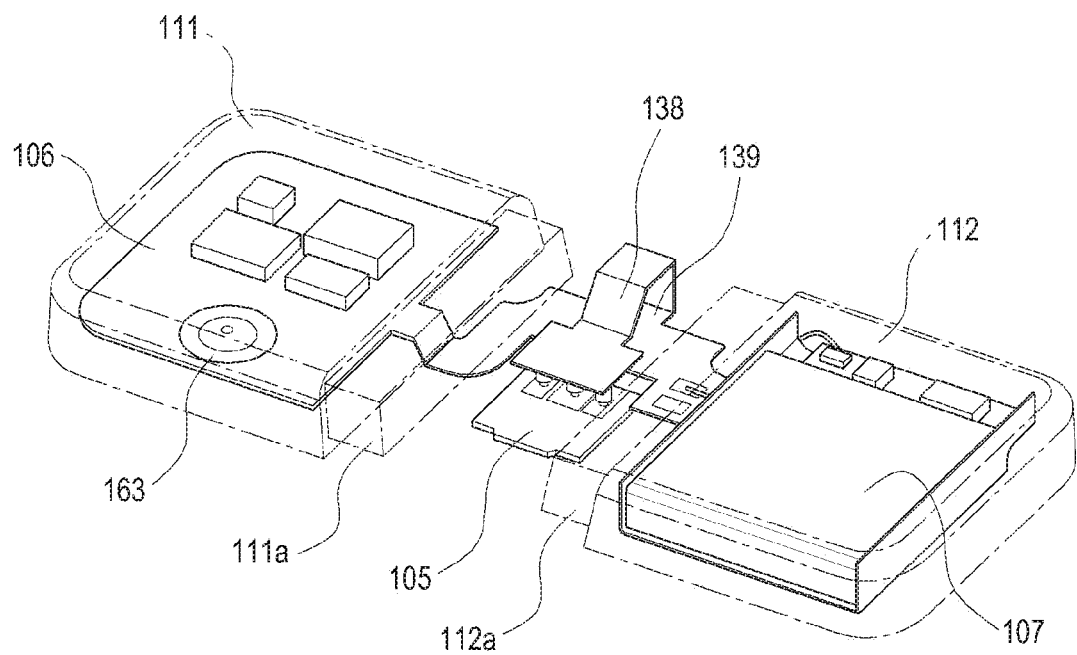
FIG. 14 is a front perspective view illustrating a first main body and a second main body of a wearable electronic device according to an embodiment of the present disclosure.

FIG. 14 is a front perspective view illustrating a first main body and a second main body of a wearable electronic device according to an embodiment of the present disclosure.

Referring to FIG. 14, the first main body 111 surrounds the circuit unit 106, and the second main body 112 surrounds the battery 107. The first main body 111 and the second main body 112 protect the circuit unit 106 and the second main body 112, respectively, from the outside. The first main body 111 and the second main body 112 are formed of rubber by an inserting molding method. Accordingly, the switch 163 in the circuit unit 106 receives the user's external force through the rubber first main body 111 as the user pressurizes the first main body 111 on the switch 163, thereby turning on/off the wearable electronic device.

Figure 15:
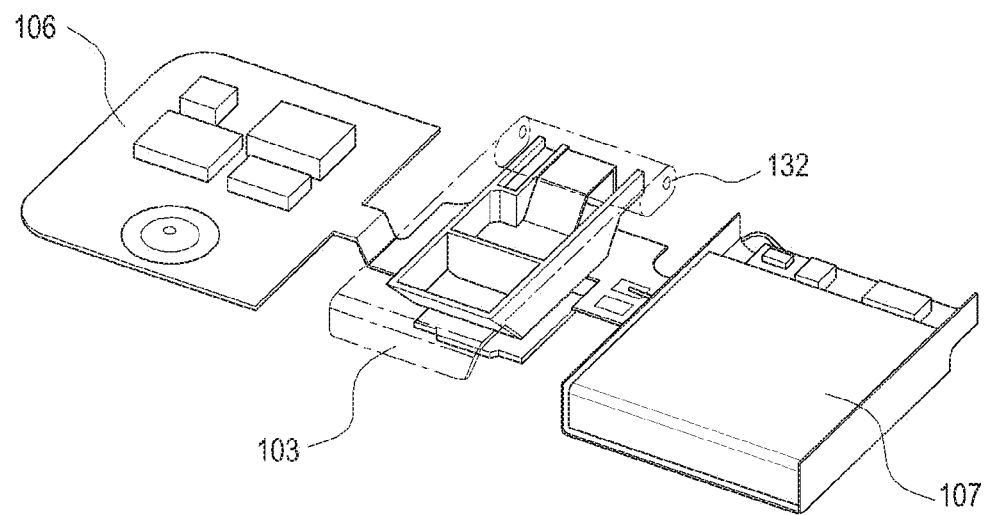
FIG. 15 is a front perspective view illustrating a cover unit of a wearable electronic device according to an embodiment of the present disclosure.

FIG. 15 is a front perspective view illustrating a cover unit of a wearable electronic device according to an embodiment of the present disclosure.

Referring to FIG. 15, the cover unit 103 surrounds the first circuit board 138 and includes a first cover unit for seating the first circuit board 138 and a second cover unit, along with the first cover unit, surrounding the first circuit board 138.

Figure 16:
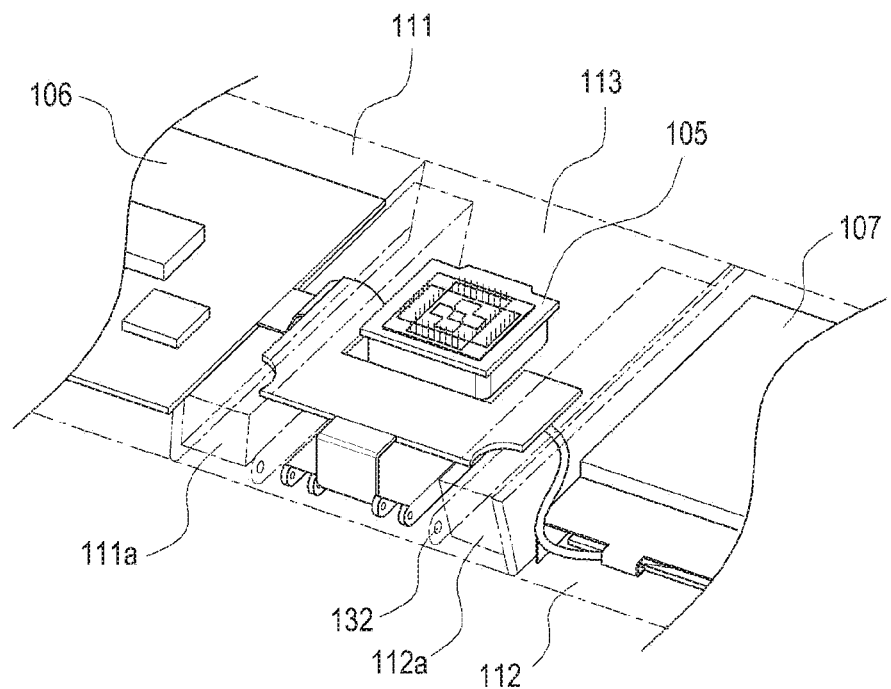
FIG. 16 is a rear perspective view illustrating a third main body of a wearable electronic device according to an embodiment of the present disclosure.

FIG. 16 is a rear perspective view illustrating a third main body of a wearable electronic device according to an embodiment of the present disclosure. Referring to FIG. 16, the third main body 113 is hinged to the cover unit 103.

The first main body 111 includes a first protrusion 111a projecting towards the second main body 112, and the second main body 112 includes a second protrusion 112a projecting towards the first main body 111.

The third main body 113 is provided between the first main body 111 and the second main body 112 to surround the first and second protrusions to thereby fasten each of the first main body 111 and the second main body 112. The first main body 111 remains fastened to the second main body 112 by the third main body 113.

Figure 17:
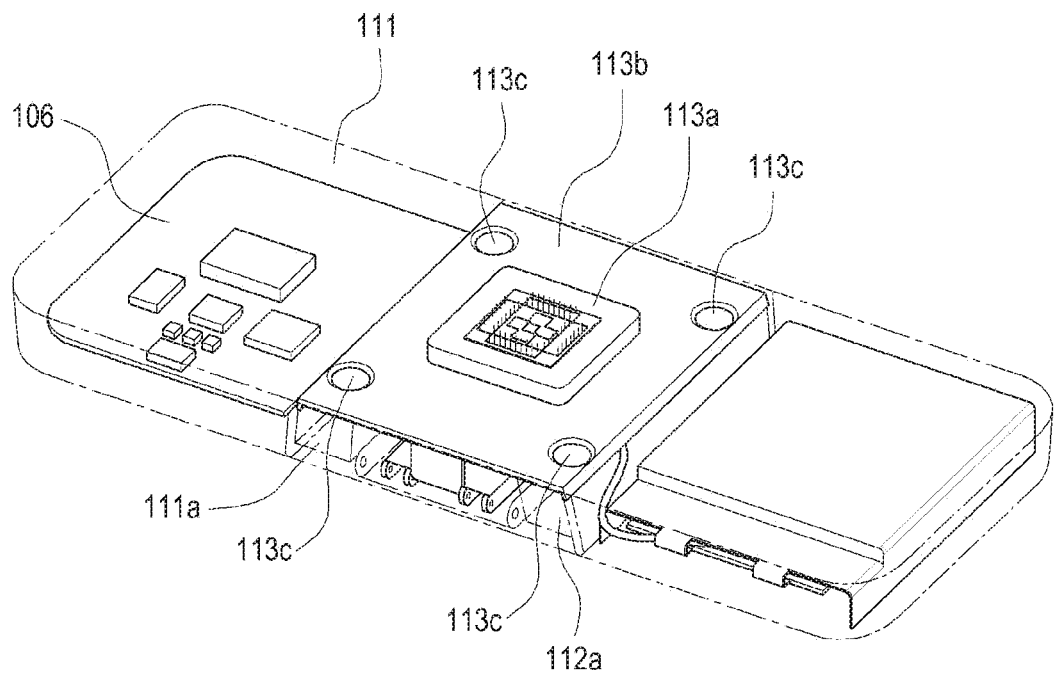
FIG. 17 is a rear perspective view illustrating an example where a receiving unit is coupled to a third main body in a wearable electronic device according to an embodiment of the present disclosure.
Figure 18:
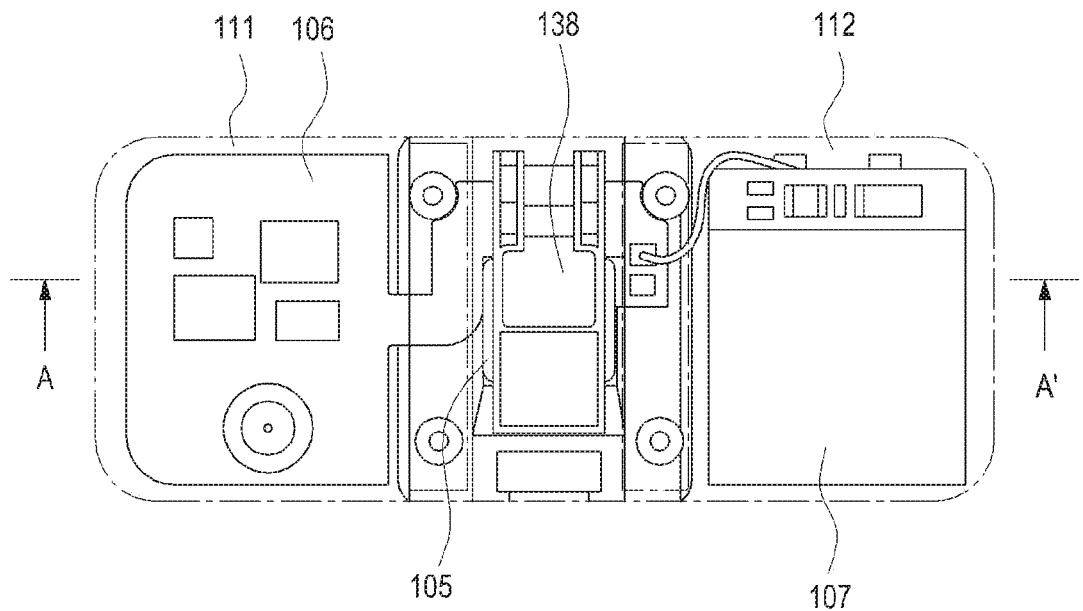
FIG. 18 is a front view illustrating the inside of a wearable electronic device according to an embodiment of the present disclosure.
Figure 19:
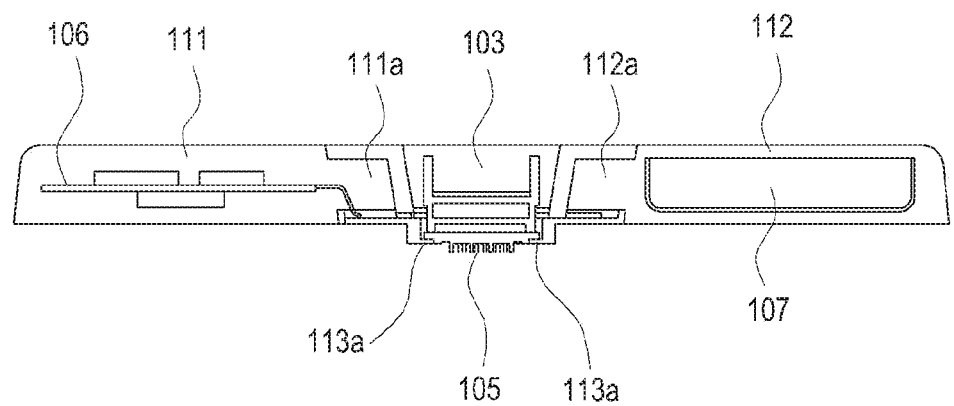
FIG. 19 is a cross-sectional view illustrating the inside of a wearable electronic device according to an embodiment of the present disclosure.

FIG. 17 is a rear perspective view illustrating an example where a receiving unit is coupled to a third main body in a wearable electronic device according to an embodiment of the present disclosure. FIG. 18 is a front view illustrating the inside of a wearable electronic device according to an embodiment of the present disclosure. FIG. 19 is a cross-sectional view illustrating the inside of a wearable electronic device according to an embodiment of the present disclosure.

Referring to FIGS. 17 to 19, the third main body 113 includes a receiving unit 113b for receiving the sensor unit 105.

The receiving unit 113b includes a seating unit for seating the sensor unit 105 while surrounding the rear surface of the third main body 113. The receiving unit 113b is coupled with the third main body 113 via bolts 113c.

As shown in FIG. 5, the pad 104 may be attached to the first, second, and third body units 111, 112, and 113 in the form of surrounding the projecting unit of the sensor unit 105.

Figure 20:
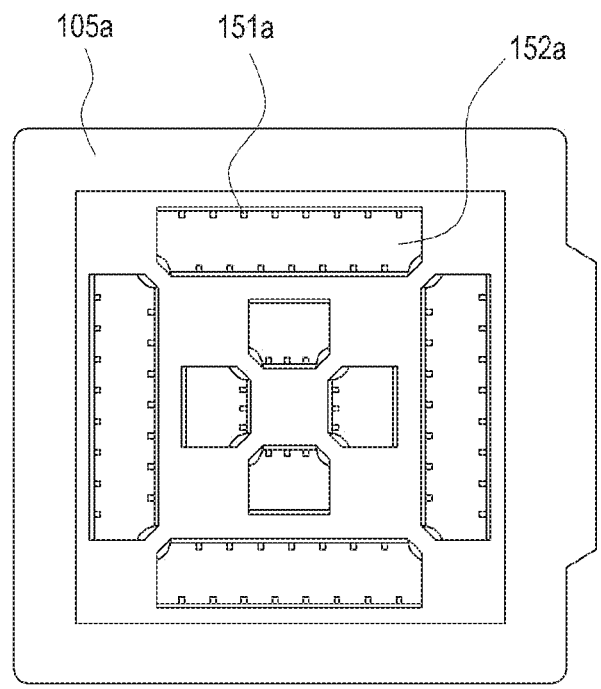
FIG. 20 is a rear view illustrating a sensor unit according to an embodiment of the present disclosure.
Figure 21:
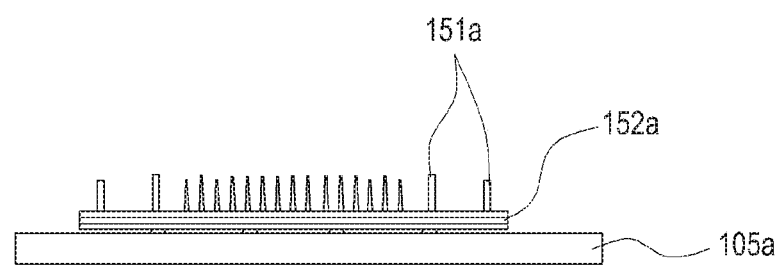
FIG. 21 is a side view illustrating a sensor unit according to an embodiment of the present disclosure.
Figure 22:
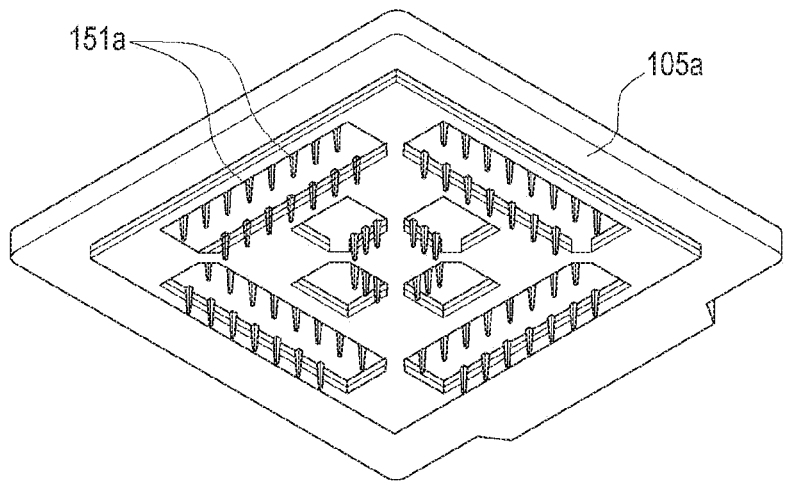
FIG. 22 is a rear perspective view illustrating a sensor unit according to an embodiment of the present disclosure.
Figure 23:
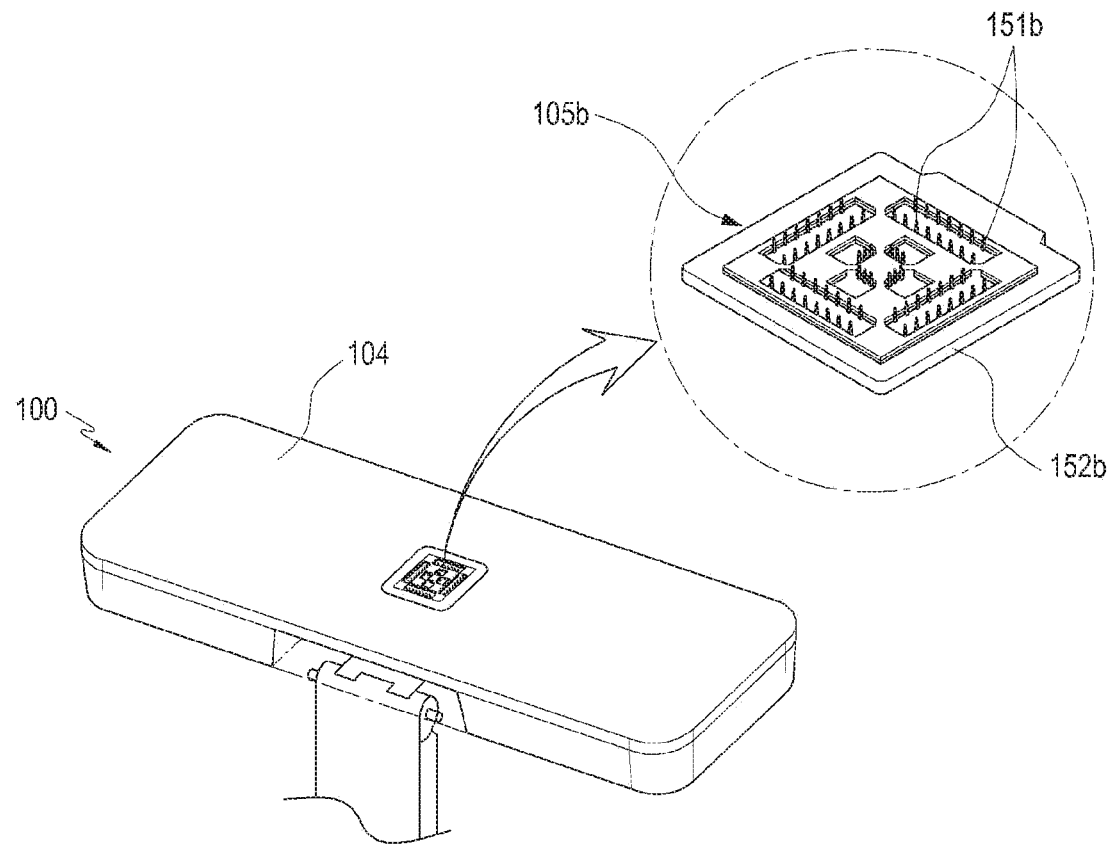
FIG. 23 is a rear perspective view illustrating a sensor unit according to an embodiment of the present disclosure.

FIG. 20 is a rear view illustrating a sensor unit according to an embodiment of the present disclosure. FIG. 21 is a side view illustrating a sensor unit according to an embodiment of the present disclosure. FIG. 22 is a rear perspective view illustrating a sensor unit according to an embodiment of the present disclosure. FIG. 23 is a rear perspective view illustrating a sensor unit according to an embodiment of the present disclosure.

Referring to FIGS. 20 to 23, the sensor unit includes micro needles 151a, a moving unit 152a, and a casing 105a.

The micro needles 151a are inserted into the body skin to collect a body fluid, such as blood, conveyed through the inside of the micro needles 151a to the moving unit 152a. The moving unit 152 is connected with the micro needles 151a to provide a transfer path to the casing 105a, which receives from the moving unit 152 and includes a working electrode and a counter electrode. The body fluid is provided between the working electrode and the counter electrode, and the blood sugar in the body fluid is measured by the amount of current flowing between the working electrode and the counter electrode.

According to an embodiment of the present disclosure, the micro needles 151a are formed of conductive polymer and contain an enzyme that performs a chemical action with the body fluid. The conductive-polymer micro needles 151 receive an electric current to trigger a chemical action between the enzyme and the biomarker, and measure the biomarker using an electrical signal generated by the chemical action, i.e., an electrical current.

Figure 24:
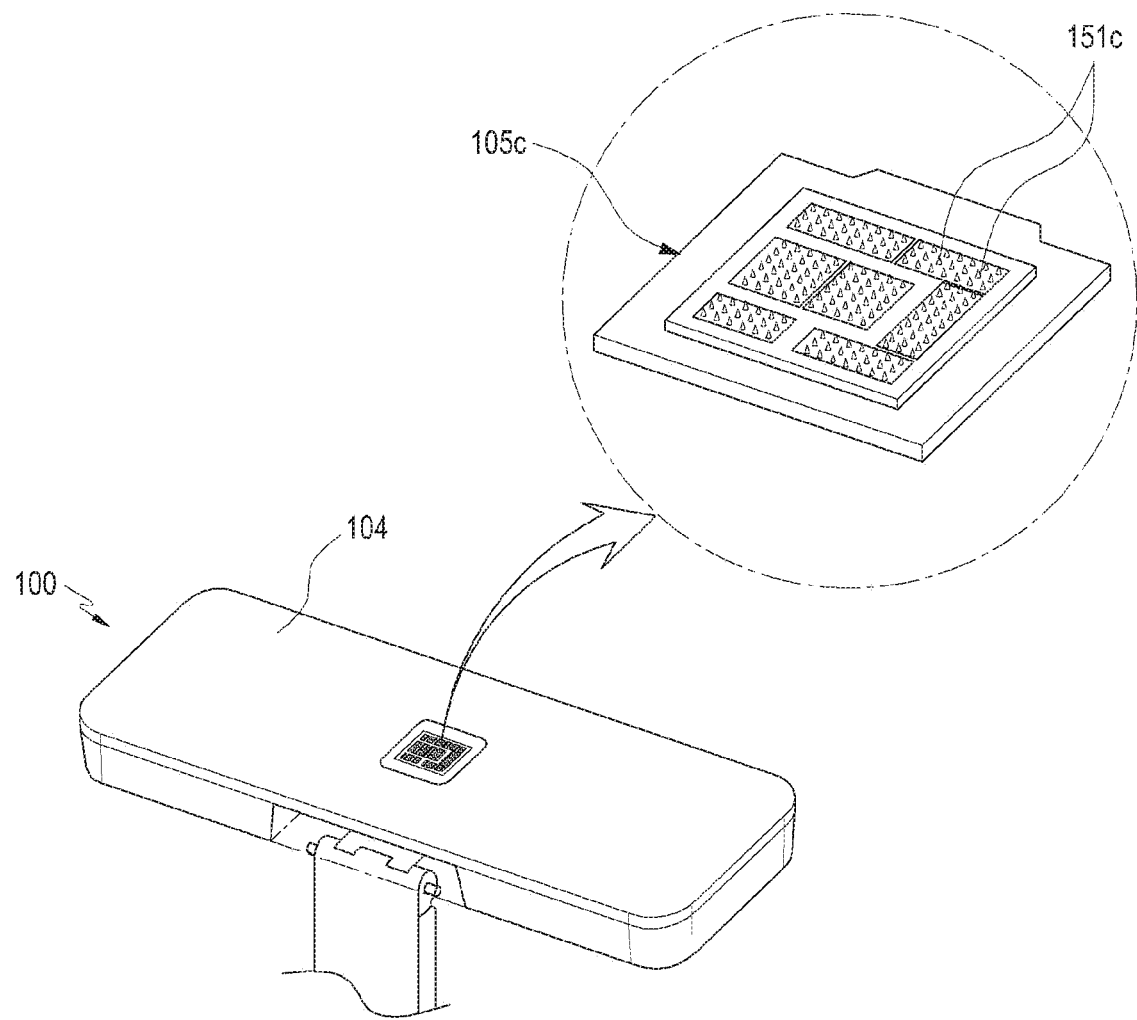
FIG. 24 is a rear perspective view illustrating a sensor unit according to an embodiment of the present disclosure.

FIG. 24 is a rear perspective view illustrating a sensor unit according to an embodiment of the present disclosure.

Referring to FIG. 24, the sensor unit 105c includes micro needles 151c with a different arrangement from those described above. As such, the sensor unit 105c includes various arrays of micro needles.

Figure 25:
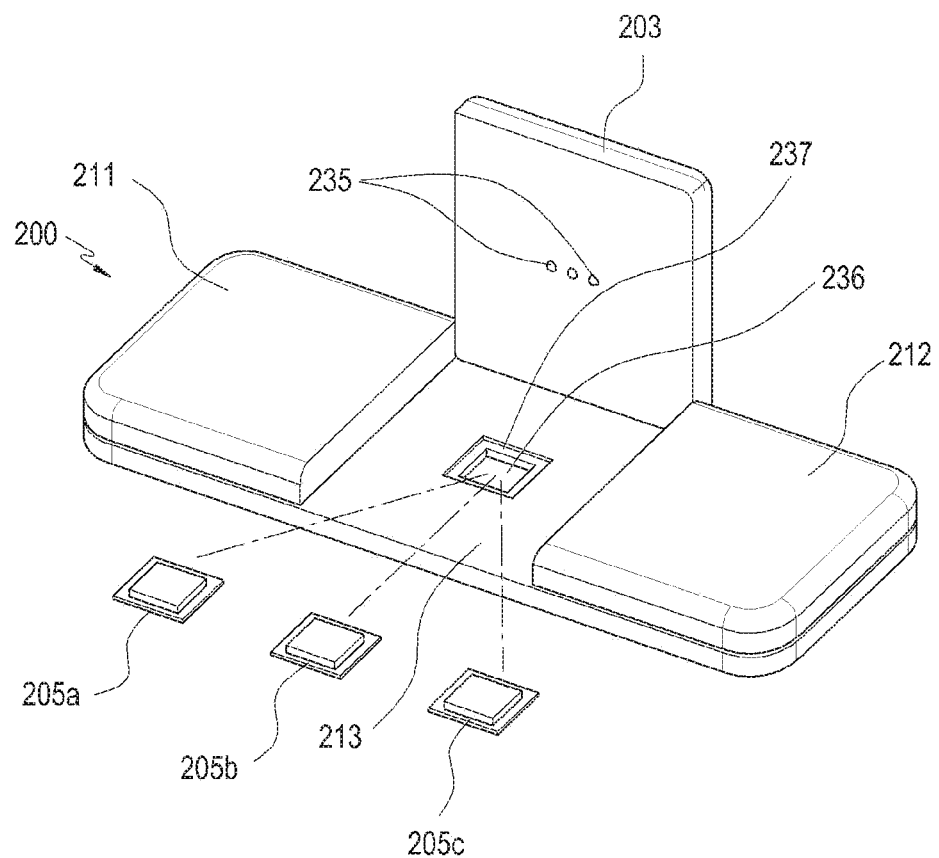
FIG. 25 is a front perspective view illustrating a wearable electronic device according to an embodiment of the present disclosure.

FIG. 25 is a front perspective view illustrating a wearable electronic device according to an embodiment of the present disclosure.

Referring to FIG. 25, the wearable electronic device 200 includes body units 211, 212, and 213, cover units 203, and sensor units 205a, 205b, and 205c. In this embodiment, the detailed description of similar elements to those described above is omitted, and the description will primarily focus on the sensor units.

The sensor units include a first sensor unit 205a, a second sensor unit 205b, and a third sensor unit 205c. The first sensor unit 205a measures blood sugar in a similar manner to the above-described embodiments. The second sensor unit 205b measures lactic acid in the body fluid. The third sensor unit 205c measures the body blood pressure using an optic sensor. In this embodiment, the first, second, and third sensor units are described merely as an example, without limiting the type of sensor units. For example, the sensor units measure at least one of cholesterol, minerals, cytokine, hormones, viruses, and germs present in the user's body. The sensor units identify a biomarker for measuring proteins, deoxyribonucleic acid (DNA), ribonucleic acid (RNA), and metabolic substances to determine the presence of a disease, such as cancer. At least one of the sensor units may be an optic sensor for measuring the body temperature, and another one of the sensor units may be a heartbeat measuring sensor.

Any one of the sensor units 205a, 205b, and 205c may be received in the receiving unit 236 while seated on the seating unit 237. The cover unit 203 rotates with the third main body 213 to hide and fasten the sensor unit 213. The sensor unit received in the receiving unit 236 is electrically connected with the contact terminals 235 mounted in the cover unit 203. Another of the sensor units 205a, 205b, and 205c is also received in the receiving unit 236. The sensor units 205a, 205b, and 205c may be the same size or may be sized differently to be received in the receiving unit 237.

As such, in the wearable electronic device 200, any one of the sensor units 205a, 205b, and 205c may be equipped to measure blood sugar and may be replaced with another of the sensor units 205a, 205b, and 205c to measure various biomarkers such as lactic acid or blood pressure.

Figure 26:
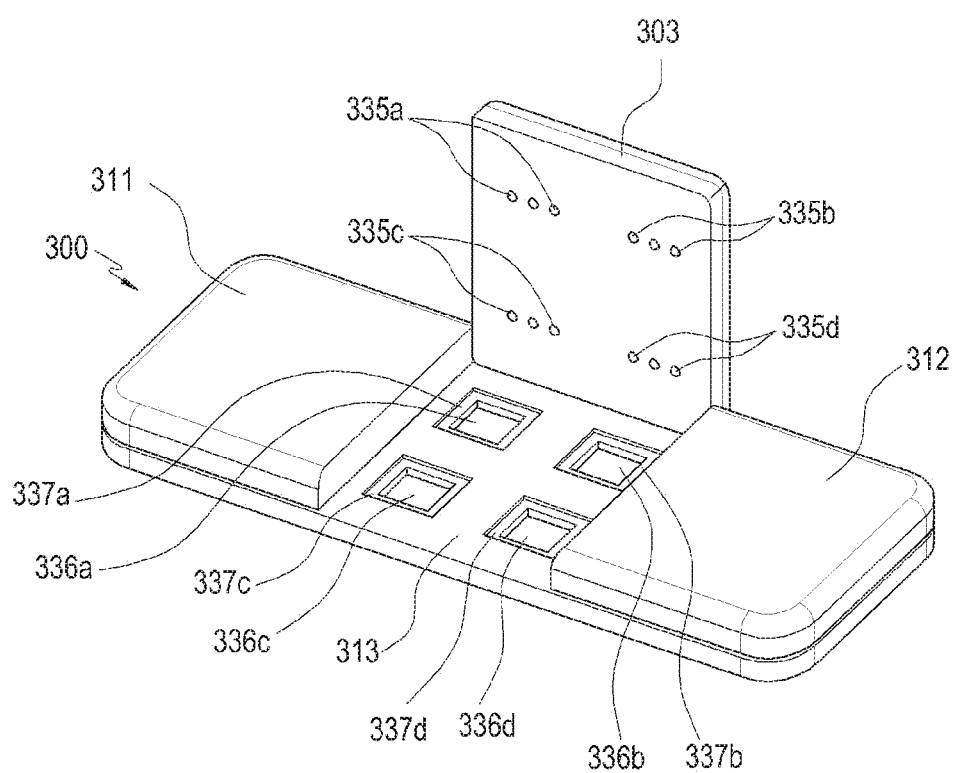
FIG. 26 is a front perspective view illustrating a wearable electronic device according to an embodiment of the present disclosure.
Figure 27:
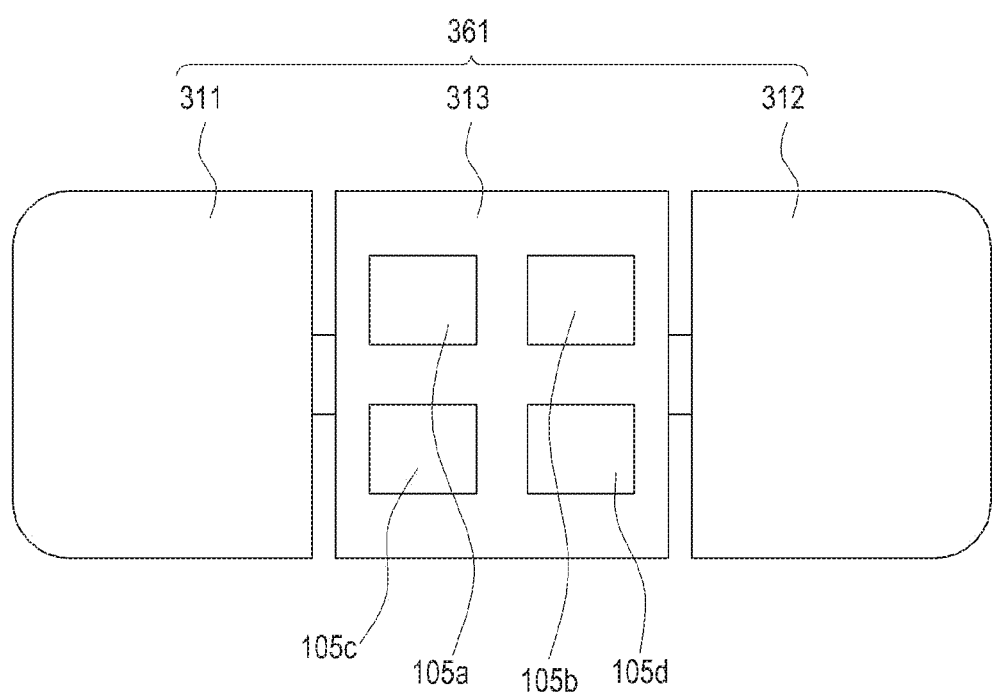
FIG. 27 is a front view illustrating a wearable electronic device according to an embodiment of the present disclosure.

FIG. 26 is a front perspective view illustrating a wearable electronic device according to an embodiment of the present disclosure. FIG. 27 is a front view illustrating a wearable electronic device according to an embodiment of the present disclosure.

Referring to FIGS. 26 and 27, the wearable electronic device 300 includes a main body 361, a cover unit 303, sensor units 105a, 105b, 105c, and 105d, and a plurality of receiving units 336a, 336b, 336c, and 336d. In this embodiment, the detailed description of similar elements to those described above is omitted.

The plurality of receiving units 336a, 336b, 336c and 336d are provided in the third main body 313 and include their respective seating units 337a, 337b, 337c, and 337d. The plurality of receiving units 336a, 336b, 336c, and 336d receive the sensor units 105a, 105b, 105c, and 105d, respectively. The sensor units 105a, 105b, 105c, and 105d are similar to the sensor unit described above, and thus the detailed description thereof is omitted. While the sensor units 105a, 105b, 105c, and 105d are received in the receiving units 336a, 336b, 336c, and 336d, respectively, the cover unit 303 hides and fastens the sensor units 105a, 105b, 105c, and 105d. The cover unit 303 includes contact terminals 335a, 335b, 335c, and 335d respectively corresponding to the sensor units 105a, 105b, 105c, and 105d to electrically connect the circuit unit with the sensor units 105a, 105b, 105c, and 105d.

The plurality of sensor units 105a, 105b, 105c, and 105d measure the same biomarker, such as blood sugar. The circuit unit compares electrical signal values by the biomarkers received from the plurality of sensor units 105a, 105b, 105c, and 105d, and when the respective measured biomarker values have a large deviation, more accurately measures biomarkers, such as by transferring signals for re-measurement.

The plurality of sensor units 105a, 105b, 105c, and 105d measure different biomarkers in a similar manner to those described above in connection with the above embodiments. The sensor units 105a, 105b, 105c, and 105d are mounted together in the wearable electronic device 300 to simultaneously measure biomarkers.

Figure 28:
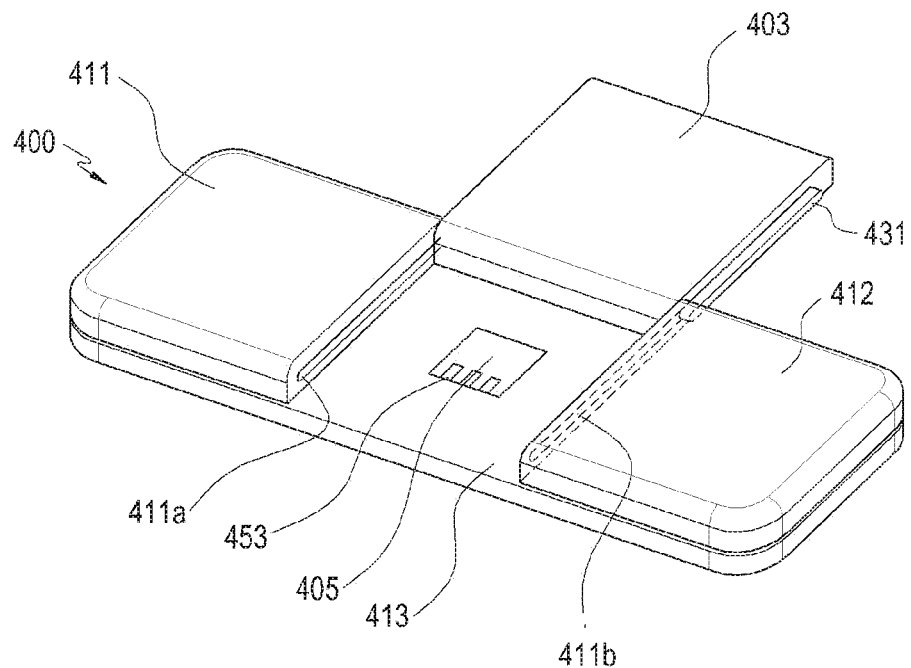
FIG. 28 is a front perspective view illustrating a wearable electronic device according to an embodiment of the present disclosure.
Figure 29:
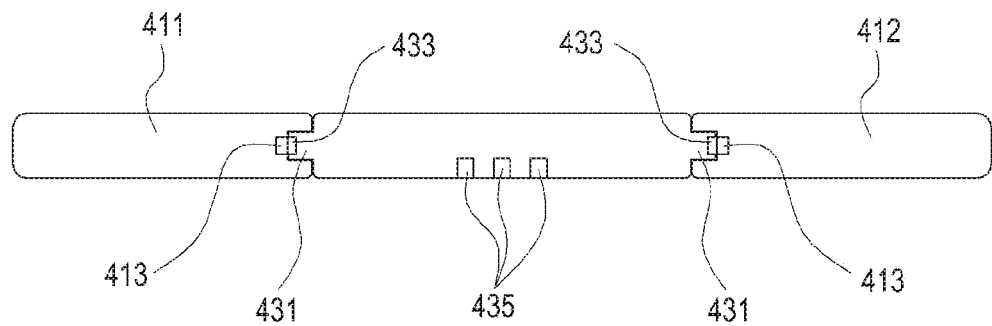
FIG. 29 is a cross-sectional view illustrating a wearable electronic device according to an embodiment of the present disclosure.
Figure 30:
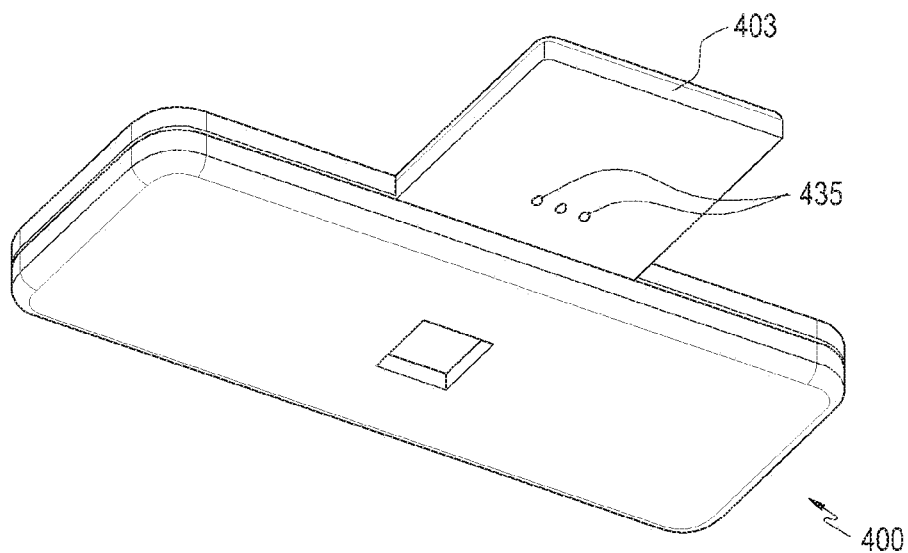
FIG. 30 is a rear perspective view illustrating a wearable electronic device according to an embodiment of the present disclosure.

FIG. 28 is a front perspective view illustrating a wearable electronic device according to an embodiment of the present disclosure. FIG. 29 is a cross-sectional view illustrating a wearable electronic device according to an embodiment of the present disclosure. FIG. 30 is a rear perspective view illustrating a wearable electronic device according to an embodiment of the present disclosure.

Referring to FIGS. 28 to 30, the wearable electronic device 400 includes body units 411, 412, and 413, a cover unit 403, and a sensor unit 405. The description of similar elements to those described above in the above embodiments is omitted, and the structure in which the cover unit is slid in the body units will now be described.

The body units 411, 412, and 413 include a first main body 411 where the circuit unit is mounted, a second main body 412 where the battery (not shown) is mounted, and a third main body 413 where the sensor unit 405 is mounted. The first main body 411 and the second main body 412 include cover guide units 411a and 411b respectively guiding two opposite ends 431 of the cover unit 403, which are projected and inserted into the cover guide units 411a and 411b. In this manner, the cover unit 403 may slide on the third main body 413.

An end of the cover unit 403 may be constrained by the cover guide units 411a and 411b so that the cover unit 403 may be fastened onto the third main body 413. As the cover unit 403 opens the receiving unit, the sensor unit 405 is detachably connected with the third main body 413. As the cover unit 403 is slid on the third main body 405 while the sensor unit 405 is received in the receiving unit, the cover unit 403 fastens the sensor unit 405 to the receiving unit.

The cover unit 403 includes a first contact terminal 435 connected with the contact pad 453 of the sensor unit 405. As the cover unit 403 is slid on the third main body 405 while the sensor unit 413 is received in the receiving unit, the contact terminal 435 is electrically connected with the contact pad 453.

Both ends 431 of the cover unit 403 include a second contact terminal 433 which is electrically connected with the first contact terminal 435. A second contact pad 413 is provided on an inner surface of the cover guide units 411a and 411b to be connected with the second contact terminal 433. The second contact pad 413 is electrically connected with the circuit unit provided in the first main body 411. The two opposite ends 431 of the cover unit 403 are inserted into the cover guide units 411a and 411b and slid, so that the second contact terminal 433 is connected with the second contact pad 413. Accordingly, the sensor unit 405 is electrically connected the circuit unit 413 sequentially passing through the first contact terminal 435, the second contact terminal 433, and the second contact pad 413. The second contact terminal 433 is connected With the second contact pad 413 connected with the battery (not shown) of the second main body 412 to electrically connect the circuit unit with the battery.

Figure 31:
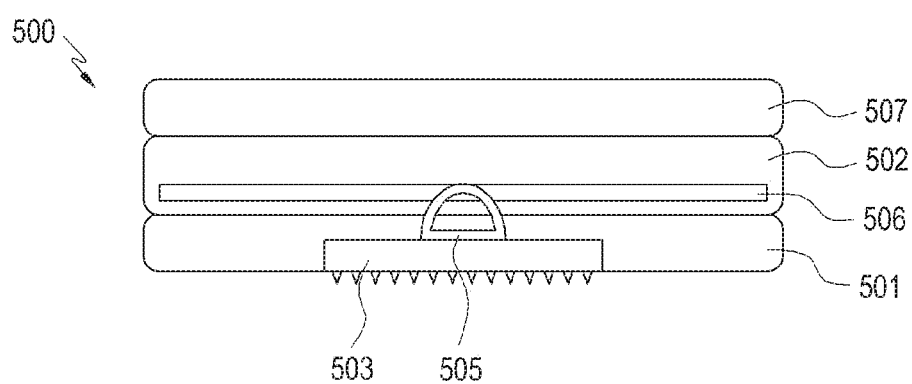
FIG. 31 is a cross-sectional view illustrating a wearable electronic device according to an embodiment of the present disclosure.

FIG. 31 is a cross-sectional view illustrating a wearable electronic device according to an embodiment of the present disclosure.

Referring to FIG. 31, the wearable electronic device 500 includes body units 501 and 502, a battery 507, and a sensor unit 503 and includes a structure in which the body units 501 and 502, the battery 507, and the sensor unit 503 are sequentially stacked.

The body units 501 and 502 include a first main body 501 for mounting the sensor unit 503, a second main body 502 for mounting the circuit unit 506, and a contact terminal 505 connecting the sensor unit 503 with the circuit unit 506.

Figure 32:
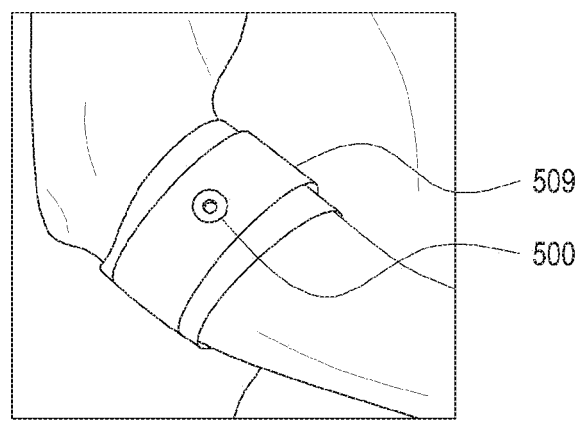
FIG. 32 illustrates a wearable device attached to a user's arm according to an embodiment of the present disclosure.

FIG. 32 illustrates a wearable device attached to a user's arm according to an embodiment of the present disclosure.

Referring to FIGS. 31 and 32, the wearable electronic device 500 may be mounted on a band 509 that is worn on the user's body, such as an arm.

Figure 33:
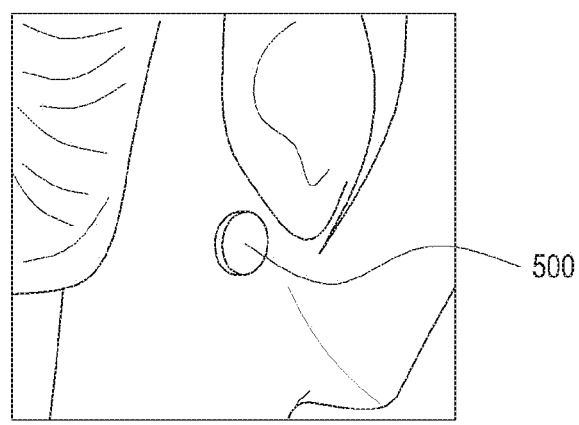
FIG. 33 illustrates a wearable device attached under a user's ear according to an embodiment of the present disclosure.

FIG. 33 illustrates a wearable device attached under a user's ear according to an embodiment of the present disclosure.

Referring also to FIGS. 31 and 32, the wearable electronic device 500 may be attached under the user's ear. The first main body 501, the second main body 502, and the battery may be stacked in various designs while reducing the area contacting the user's body.

Figure 34:
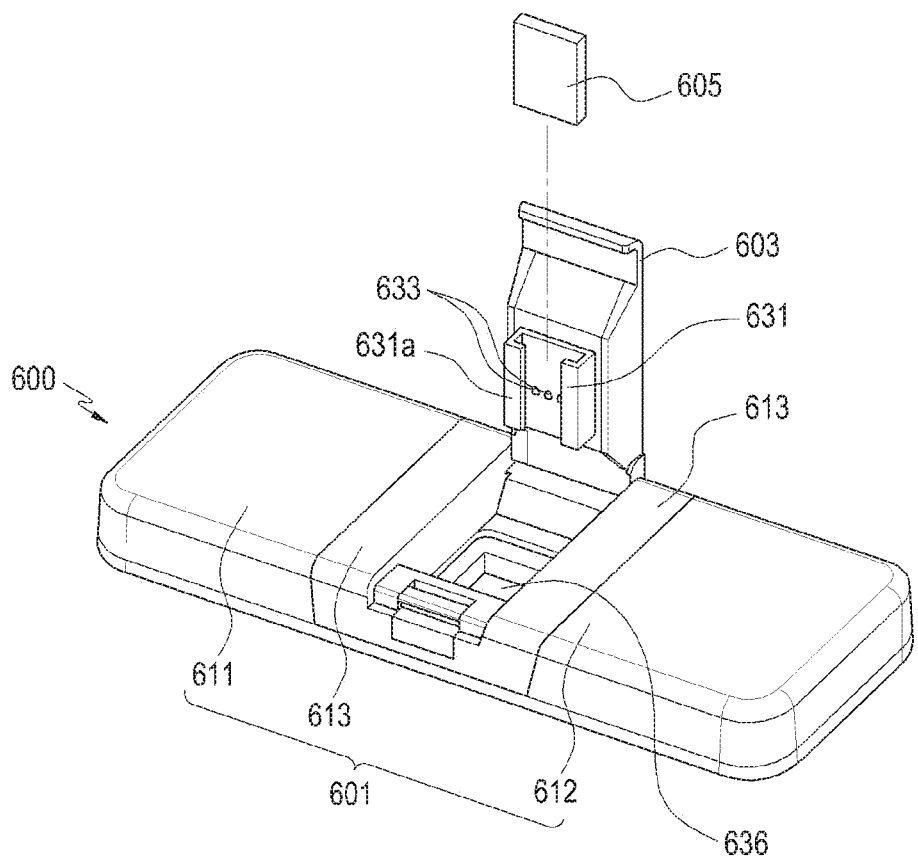
FIG. 34 is a front perspective view illustrating a wearable electronic device according to an embodiment of the present disclosure.
Figure 35:
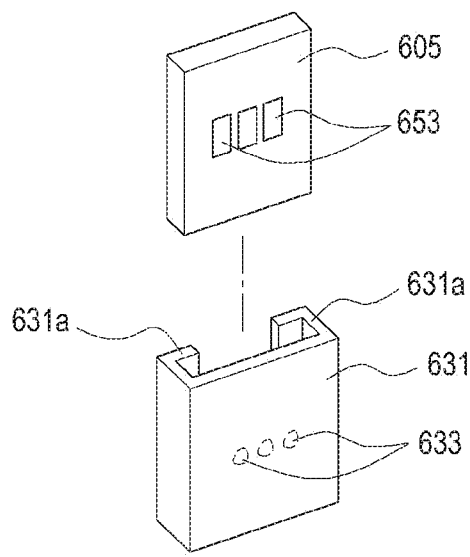
FIG. 35 is a perspective view illustrating a sensor unit inserted into a guide unit of a wearable electronic device according to an embodiment of the present disclosure.

FIG. 34 is a front perspective view illustrating a wearable electronic device according to an embodiment of the present disclosure. FIG. 35 is a perspective view illustrating a sensor unit inserted into a guide unit of a wearable electronic device according to an embodiment of the present disclosure.

Referring to FIGS. 34 to 35, the wearable electronic device 600 includes a main body 601, a cover unit 603, and a sensor unit 605. The body unit 601 includes a first body unit 611, a second body unit 612 and a third body unit 613. In this embodiment, the description of similar elements to those described above in the above embodiments is omitted, and this description will primarily focus on the structure in which the sensor unit 605 is detachably coupled to the cover unit 603.

The cover unit 603 includes a sensor guide unit 631 corresponding to both ends of the sensor unit 605. The sensor guide unit 631 includes a protrusion 631a that is extended from the two opposite ends of the sensor guide unit 631 to partially surround the rear surface of the sensor unit 605, which is inserted and fastened to the sensor guide unit 631.

The cover unit 603 rotates on the third main body 613 to receive the sensor unit 605 in the receiving unit 636. The receiving unit 636 includes a space corresponding to the sensor guide unit 631 where the sensor unit 605 is inserted. As the sensor unit 605 is inserted into or removed from the sensor guide unit 631, the sensor unit may be replaced from the wearable electronic device 600 when necessary.

The sensor unit 605 includes a contact pad 653, and the sensor guide unit 631 includes a contact terminal 633 electrically connected with the contact pad 653. As the sensor unit 605 is slid and coupled to the sensor guide unit 631, the contact terminal 633 is connected to the contact pad 653.

Figure 36:
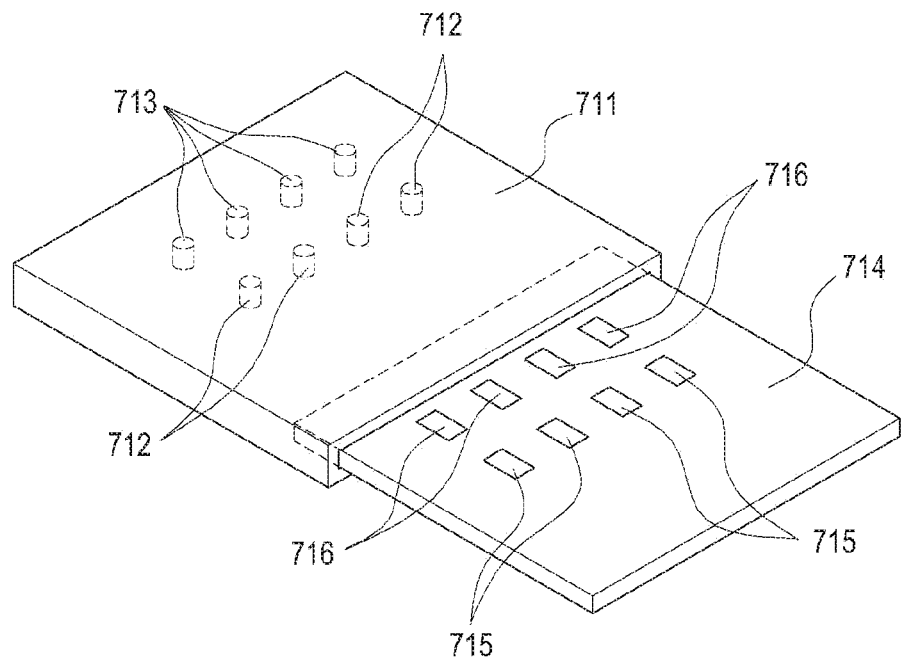
FIGS. 36, 37 and 38 are perspective views illustrating a process of connecting contact terminals of a wearable electronic device to contact pads according to an embodiment of the present disclosure.
Figure 37:
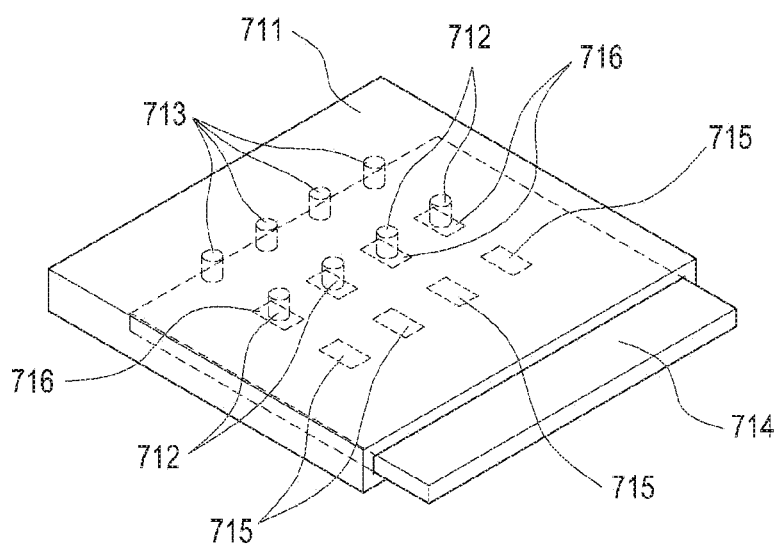
Figure 38:
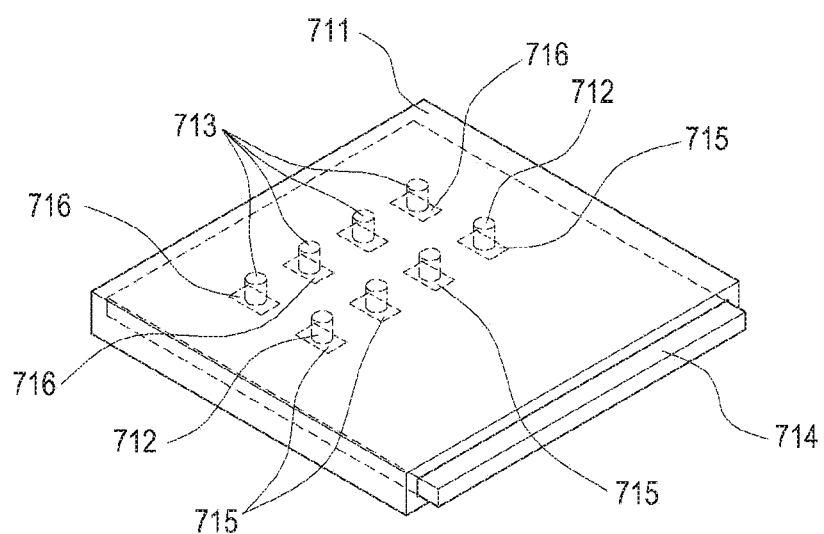

FIGS. 36 to 38 are perspective views illustrating a process of connecting contact terminals of a wearable electronic device to contact pads according to an embodiment of the present disclosure.

Referring to FIGS. 36 to 38, the sensor guide unit 711 of the wearable electronic device includes contact terminals 712 and 713.

The contact terminals include first contact terminals 712 arranged in one direction and second contact terminals 713 arranged in a direction parallel with the first contact terminals 712.

The sensor unit 714 includes first contact pads 715 arranged in one direction and second contact pads 716 arranged in a direction parallel with the first contact pads 716. While the sensor unit 714 is inserted into the guide unit 711, as shown in FIG. 37, the first contact terminals 712 contact the second contact pads 716 to detect the insertion of the wearable electronic device into the sensor unit 714.

As shown in FIG. 38, as the sensor unit 714 is inserted and fastened to the sensor guide unit 711, the first contact terminals 712 are connected with the first contact pads 715, and the second contact terminals 713 are connected with the second contact pads 716. Depending on whether the contact terminals 712 and 713 are electrically connected with the contact pads 714 and 715, respectively, the circuit unit determines the type of the sensor unit 714. For example, as shown in FIG. 36, when any one of the contact pads 714 and 715 is not provided, as the sensor unit 714 is inserted into the sensor guide unit 711, any one of the contact terminals 712 and 713 is not electrically connected, and the circuit unit determines the type of sensor unit 714 depending on whether each contact terminal 712 and 713 is electrically connected. That is, the type of the sensor unit 714 mounted in the sensor guide unit 711 may be set depending on whether there are the contact pads 715 and 716.

Figure 39:
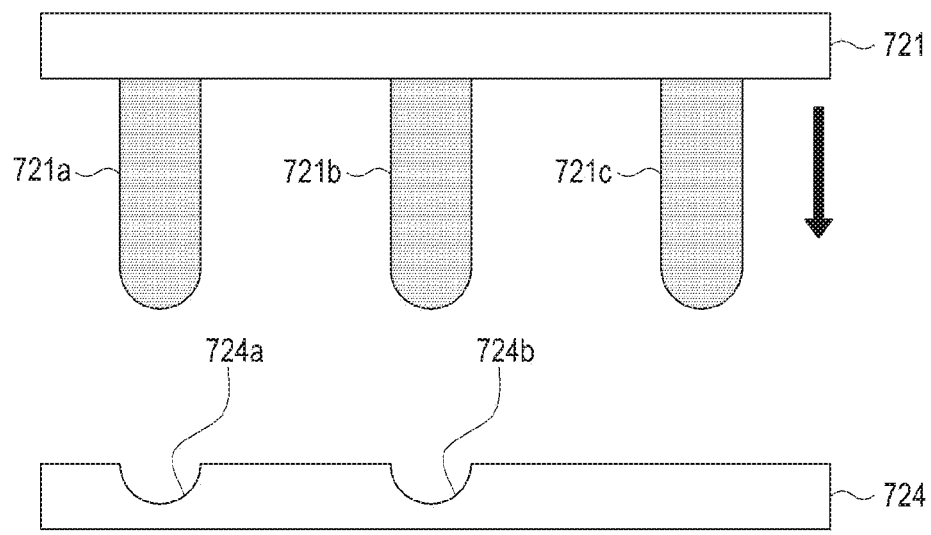
FIG. 39 illustrates contact terminals of a wearable electronic device prior to their insertion into contact holes according to an embodiment of the present disclosure.
Figure 40:
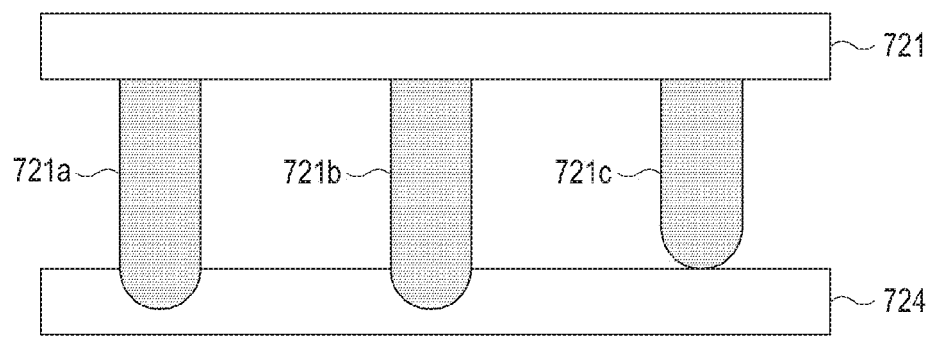
FIG. 40 illustrates some contact terminals of a wearable electronic device inserted into contact holes according to an embodiment of the present disclosure.

FIG. 39 illustrates contact terminals of a wearable electronic device prior to their insertion into contact holes according to an embodiment of the present disclosure. FIG. 40 illustrates some contact terminals of a wearable electronic device inserted into contact holes according to an embodiment of the present disclosure.

Referring to FIGS. 39 and 40, the sensor unit 724 includes a first connection hole 724a and a second connection hole 724b. However, the number of connection holes is not limited thereto.

According to an embodiment of the present disclosure, the cover unit 721 of the wearable electronic device includes contact terminals 721a, 721b, and 721c, and the cover unit 721 rotates towards the sensor unit 724. The contact terminals 721a, 721b, and 721c may be extended or contracted along a longitudinal direction in a similar manner to the above-described embodiments. The contact terminals 721a, 721b, and 721c may be elastic units such as the pogo pins 135 shown in FIG. 7. The contact terminals include a first contact terminal 721a, a second contact terminal 721b, and a third contact terminal 721c. However, the number of contact terminals is not limited thereto.

As the cover unit 721 approaches the sensor unit 724, the first contact terminal 721a is inserted into the first connection hole 724a, and the second contact terminal 721b is inserted into the second connection hole 724b. By contrast, the third contact terminal 721c does not have a corresponding connection hole.

The circuit unit determines the type of the sensor unit depending on the contact terminals inserted into the connection holes 721a and 721b or a combination of the contact terminals 724a and 724b. For example, the circuit unit determines that the sensor unit having the first connection hole 724a and the second connection hole 724b respectively corresponding to the first contact terminal 721a and the second contact terminal 721b is to measure blood sugar, as shown in FIG. 39. As another example, if a third connection hole is provided on the sensor unit 724, upon having the first connection hole 724a and the third connection hole respectively corresponding to the first contact terminal 721a and the third contact terminal 721c, the circuit unit determines that the sensor unit is to measure blood pressure.

The connection holes 724a and 724b are electrically connected with the contact terminals 721a and 721b, respectively. The circuit unit determines the type of the sensor unit mounted in the wearable electronic device depending on whether each of the contact terminals is electrically connected with any one of the connection holes.

Figure 41:
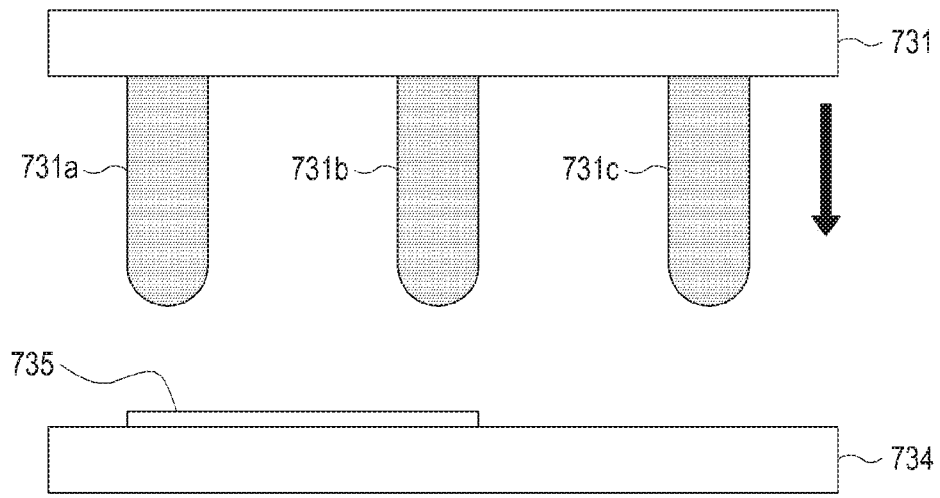
FIG. 41 illustrates an example where contact terminals of a wearable electronic device before connected to contact pads according to an embodiment of the present disclosure.
Figure 42:
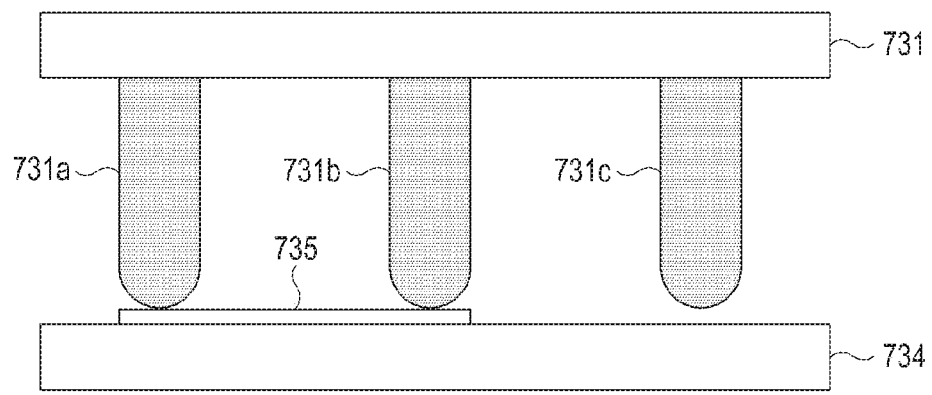
FIG. 42 illustrates some contact terminals of a wearable electronic device connected to contact pads according to an embodiment of the present disclosure.
Figure 43:
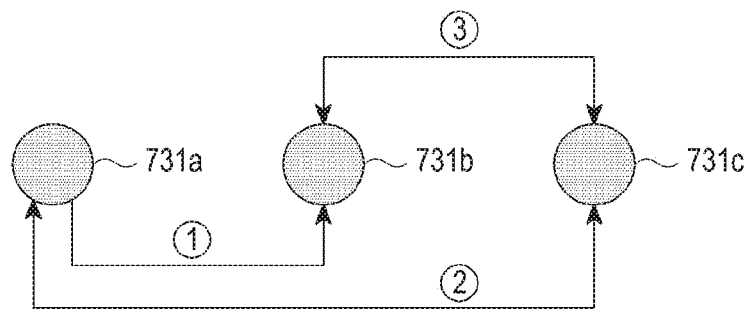
FIG. 43 illustrates an electrical connection between contact terminals of a wearable electronic device and contact pads according to an embodiment of the present disclosure.

FIG. 41 illustrates an example where contact terminals of a wearable electronic device before connected to contact pads according to an embodiment of the present disclosure. FIG. 42 illustrates some contact terminals of a wearable electronic device connected to contact pads according to an embodiment of the present disclosure. FIG. 43 illustrates an electrical connection between contact terminals of a wearable electronic device and contact pads according to an embodiment of the present disclosure.

Referring to FIGS. 41 to 43, the cover unit 731 of the electronic device includes contact terminals 731a, 731b, and 731c. The contact terminals include a first contact terminal 731a, a second contact terminal 731b, and a third contact terminal 731c. However, the number of contact terminals is not limited thereto.

The sensor unit 734 includes a contact pad 735 electrically connected with at least a pair of contact terminals among the contact terminals. For example, as shown in FIG. 43 at ①, the contact pad 735 is electrically connected with the first contact terminal 731a and the second contact terminal 731b, and the circuit unit determines that the sensor unit 734 is to measure blood sugar. For example, as shown in FIG. 43 at ③, when the second contact terminal 731b and the third contact terminal 731c are electrically connected with the contact pad, the circuit unit determines that the sensor unit 734 is to measure blood pressure. As shown in FIG. 43 at ②, when the first contact terminal 731a and the third contact terminal 731c are electrically connected via the contact pad, the circuit unit determines the type of the sensor unit.

Figure 44:
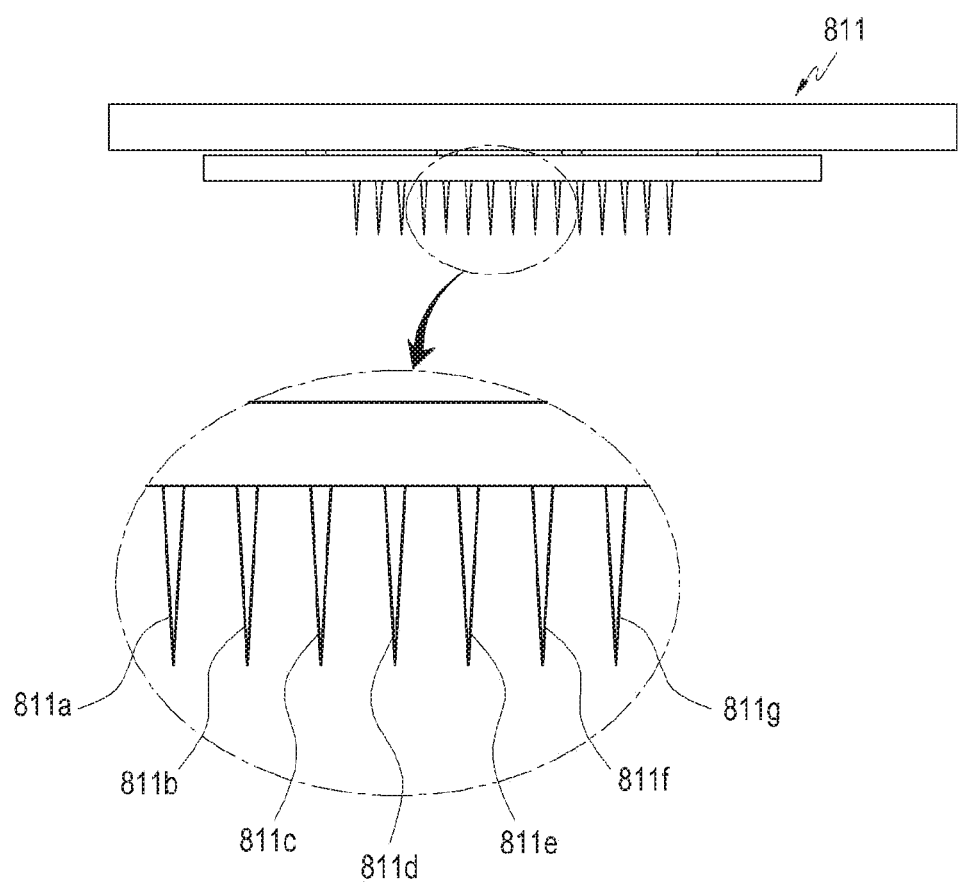
FIG. 44 is a side view illustrating a sensor unit according to an embodiment of the present disclosure.
Figure 45:
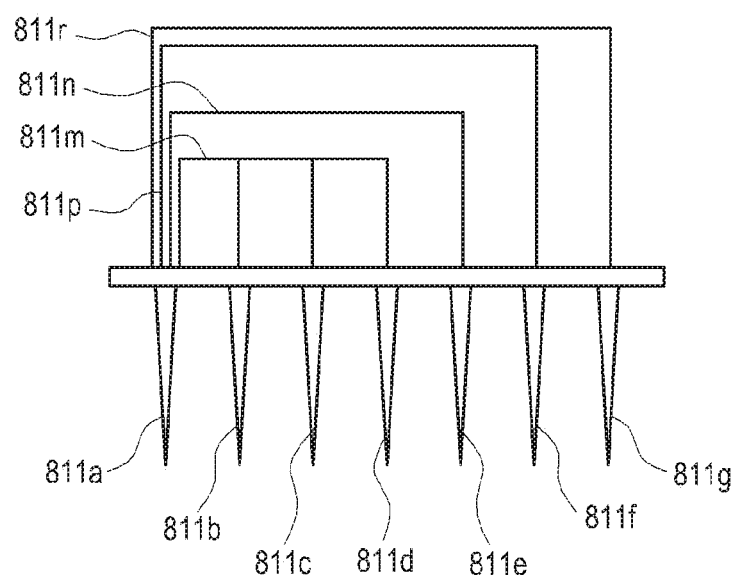
FIG. 45 illustrates an electrical connection between a reference electrode of a sensor unit and each working electrode according to an embodiment of the present disclosure.

FIG. 44 is a side view illustrating a sensor unit according to an embodiment of the present disclosure. FIG. 45 illustrates an electrical connection between a reference electrode of a sensor unit and each working electrode according to an embodiment of the present disclosure.

Referring to FIGS. 44 and 45, the sensor unit 811 includes a plurality of micro needles 811a, 811b, 811c, 811d, 811e, 811f, and 811g inserted into the user's skin to detect the user's bio signal.

The micro needles 811a, 811b, 811c, 811d, 811e, 811f, and 811g are of the same length and project in the same direction. However, the micro needles 811a, 811b, 811c, 811d, 811e, 811f, and 811g may include different lengths.

The micro needles 811a, 811b, 811c, 811d, 811e, 811f, and 811g are formed of an organic material containing a mixture of an enzyme member and a conductive polymer.

The micro needles 811a, 811b, 811c, 811d, 811e, 811f, and 811g include a reference electrode 811a, a counter electrode 811b, and working electrodes 811c, 811d, 811e, 811f, and 811g. The reference electrode 811a is electrically connected with the working electrodes 811c, 811d, 811e, 811f, and 811g via leads 811p, 811m, 811n, and 811r to apply voltage to the working electrodes 811c, 811d, 811e, 811f, and 811g.

The wearable electronic device includes a power supply for supplying power to the reference electrode and a controller for controlling the power supply. The controller controls the power supply to adjust the voltage between the reference electrode 811a and the working electrodes 811c, 811d, 811e, 811f, and 811g. That is, the power supply applies different voltages between the reference electrode 811a and the working electrodes 811c, 811d, 811e, 811f, and 811g.

The counter electrode 811b is electrically connected with each of the working electrodes 811c, 811d, 811e, 811f, and 811g. The current between each of the working electrodes 811c, 811d, 811e, 811f, and 811g and the counter electrode 811b may be varied depending on the voltage between each of the working electrodes 811c, 811d, 811e, 811f, and 811g and the reference electrode 811a. For example, when the voltage between any one 811c of the working electrodes and the reference electrode 811a is substantially 0.4V, the sensor unit 811 detects the current flowing between the working electrode 811c and the counter electrode 811b to measure the user's blood sugar concentration.

When the voltage between one 811c of the working electrodes and the reference electrode 811a is about 0.4V, and another 811d of the working electrodes and the reference electrode 811a is about 0.4V, the sensor unit 811 detects not only the current flowing between the working electrode 811c and the counter electrode 811b but also the current flowing between the working electrode 811c and the counter electrode 811b and the current flowing between the working electrode 811d and the counter electrode 811b to more precisely measure the user's blood sugar concentration. When the voltage between another 811e of the working electrodes and the reference electrode 811a is substantially 0.5V, the sensor unit 811 detects the current flowing between the working electrode 811e and the counter electrode 811b to measure the user's lactic acid concentration. When the voltage between another 811f of the working electrodes and the reference electrode 811a is substantially 0.7V, the sensor unit 811 detects the current flowing between the working electrode 811f and the counter electrode 811b to measure the user's mineral concentration. When the voltage between another 811g of the working electrodes and the reference electrode 811a is a voltage other than the above-described voltages, i.e., 0.4V, 0.5V, and 0.7V, the sensor unit 811 detects the current flowing between the working electrode 811g and the counter electrode 811b to measure the user's other bio signals, such as the concentration of disease biomarkers (hs-CRP, Troponin I, creatine kinase (CK)-MB, Mb, aspartate aminotransferase (AST) or cancer cell-derived substances), cytokine, hormones, viruses, virus-derived substances, germs, or germ-derived substances.

As such, the sensor unit 811 simultaneously measures various types of bio signals by varying the voltage between the reference electrode 811a and each of the working electrodes 811c, 811d, 811e, 811f, and 811g.

Figure 46:
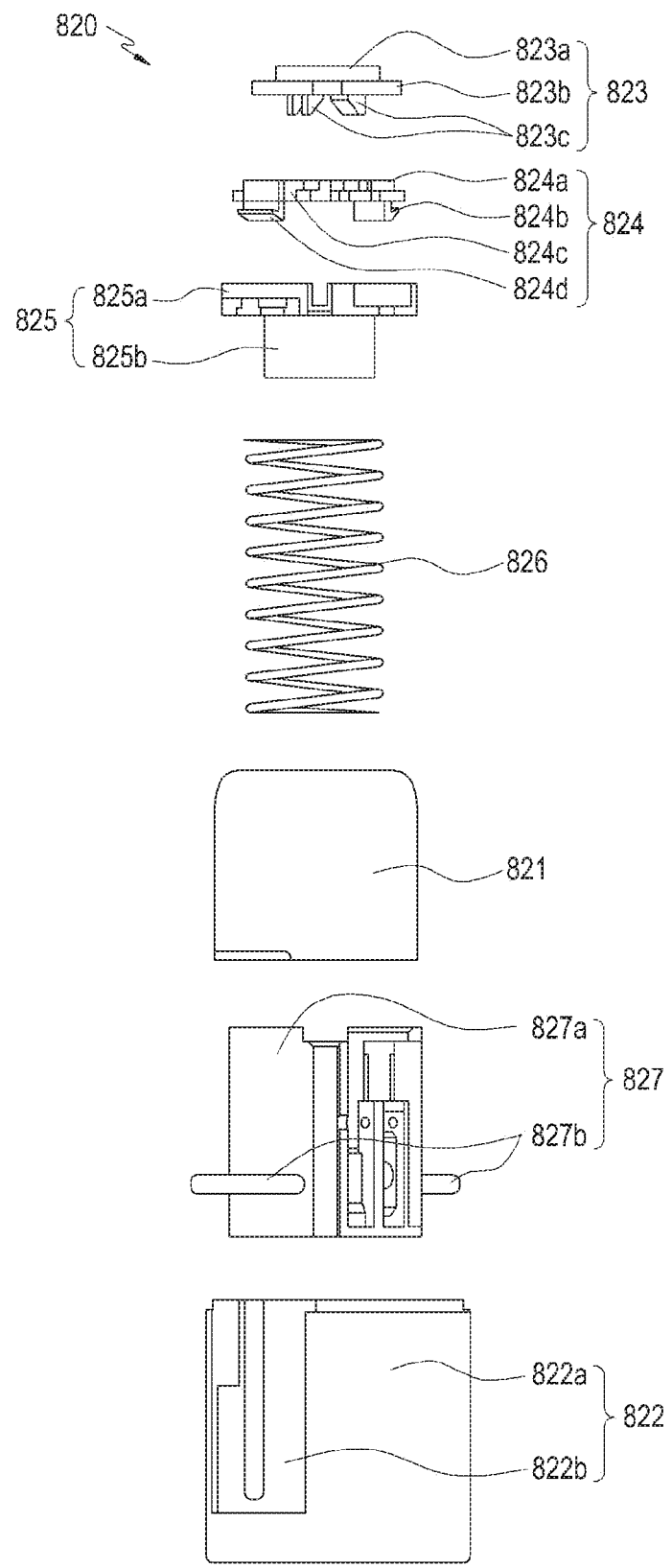
FIG. 46 is an exploded perspective view illustrating an attaching device of a wearable electronic device including a first housing and a second housing according to an embodiment of the present disclosure.
Figure 47:
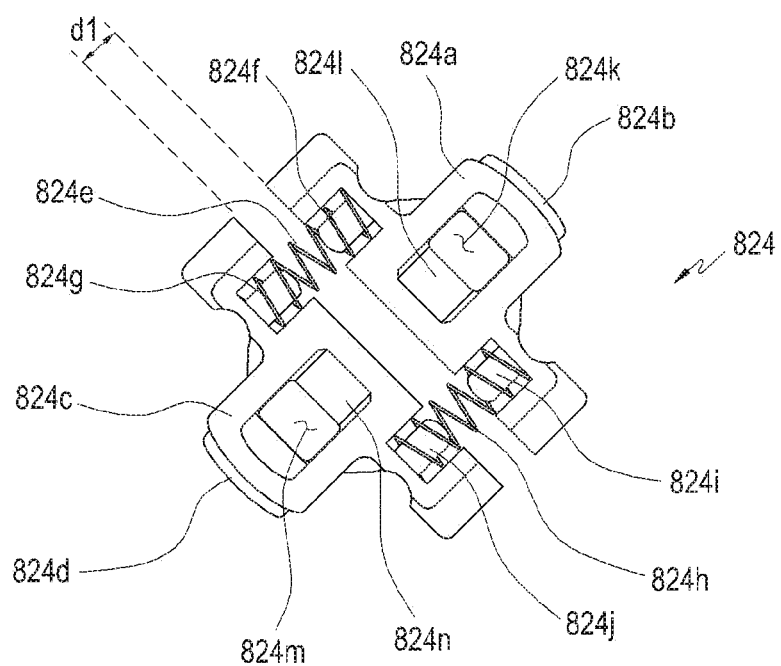
FIG. 47 is a plan view illustrating a hooking unit of a wearable electronic device according to an embodiment of the present disclosure.
Figure 48:
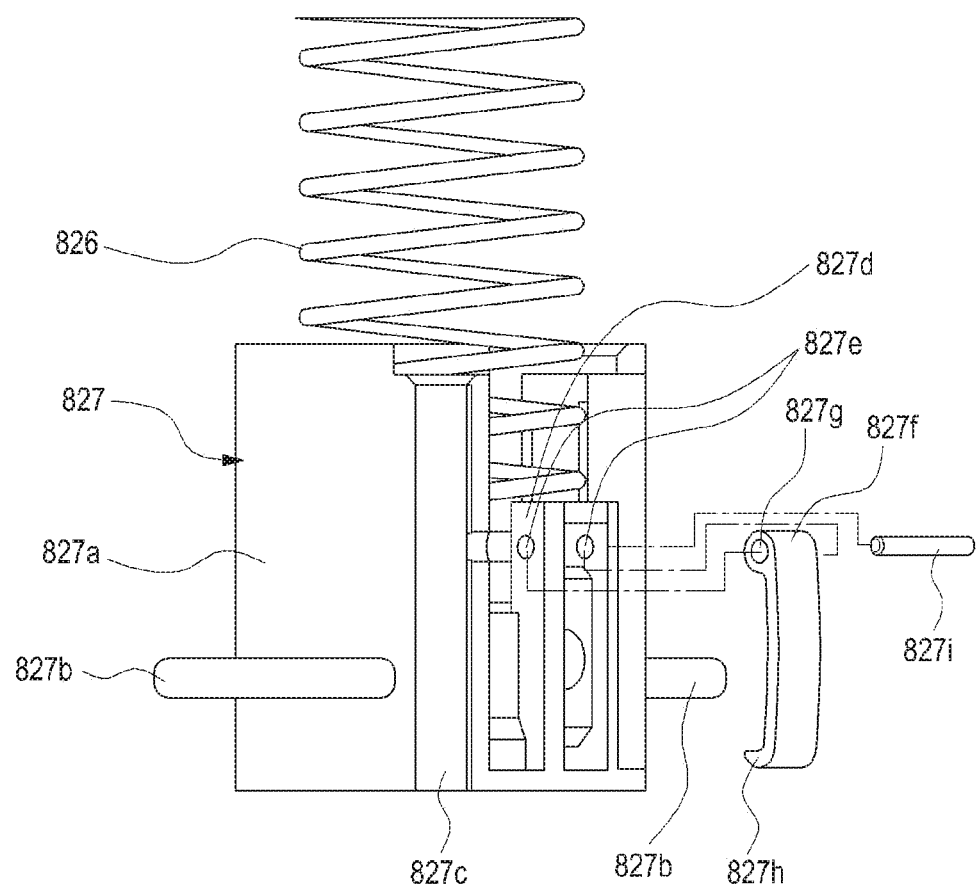
FIG. 48 is a perspective view illustrating a coupling unit of a wearable electronic device separated from a moving unit according to an embodiment of the present disclosure.
Figure 49:
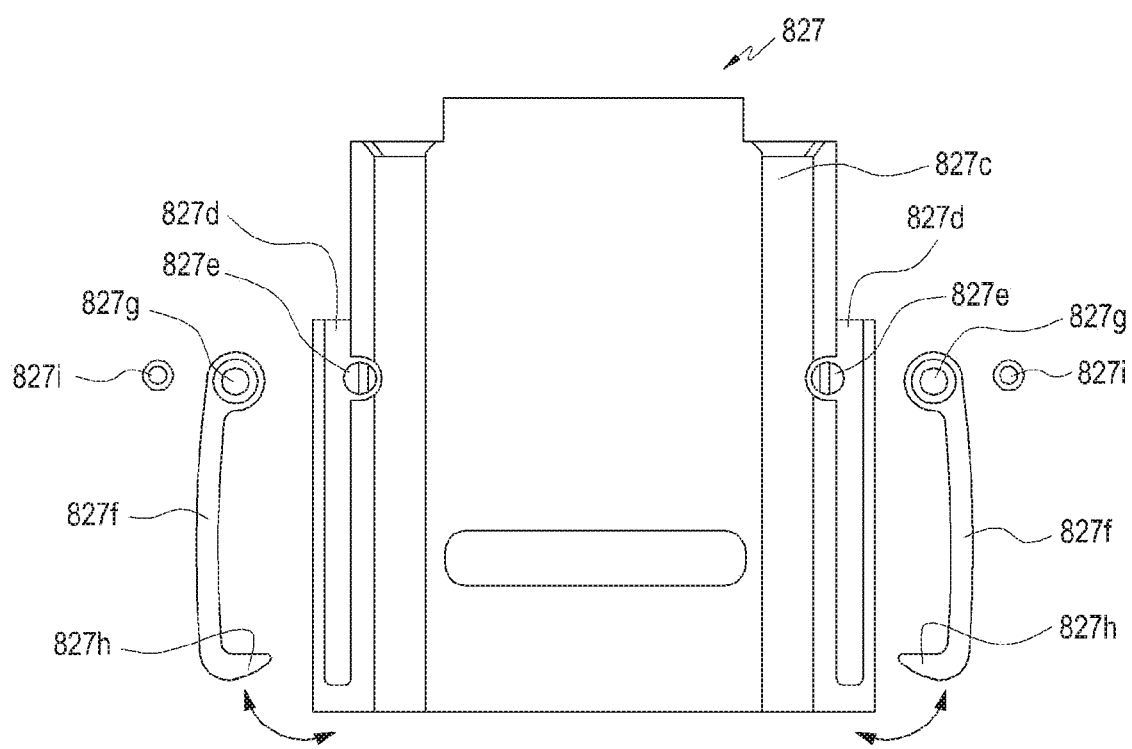
FIG. 49 is a front view illustrating a coupling unit of a wearable electronic device separated from a moving unit according to an embodiment of the present disclosure.
Figure 50:
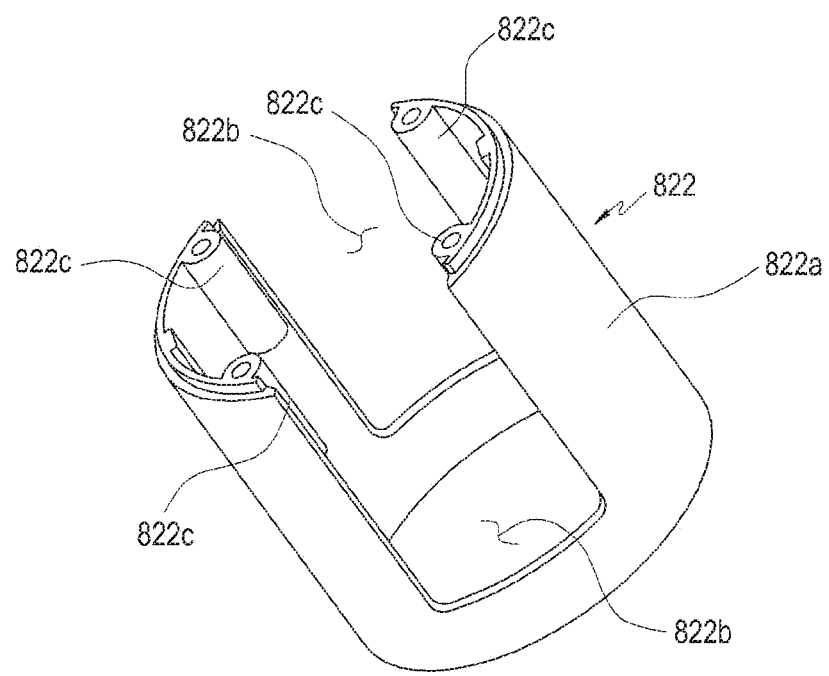
FIG. 50 is a perspective view illustrating a second housing of a wearable electronic device according to an embodiment of the present disclosure.
Figure 51:
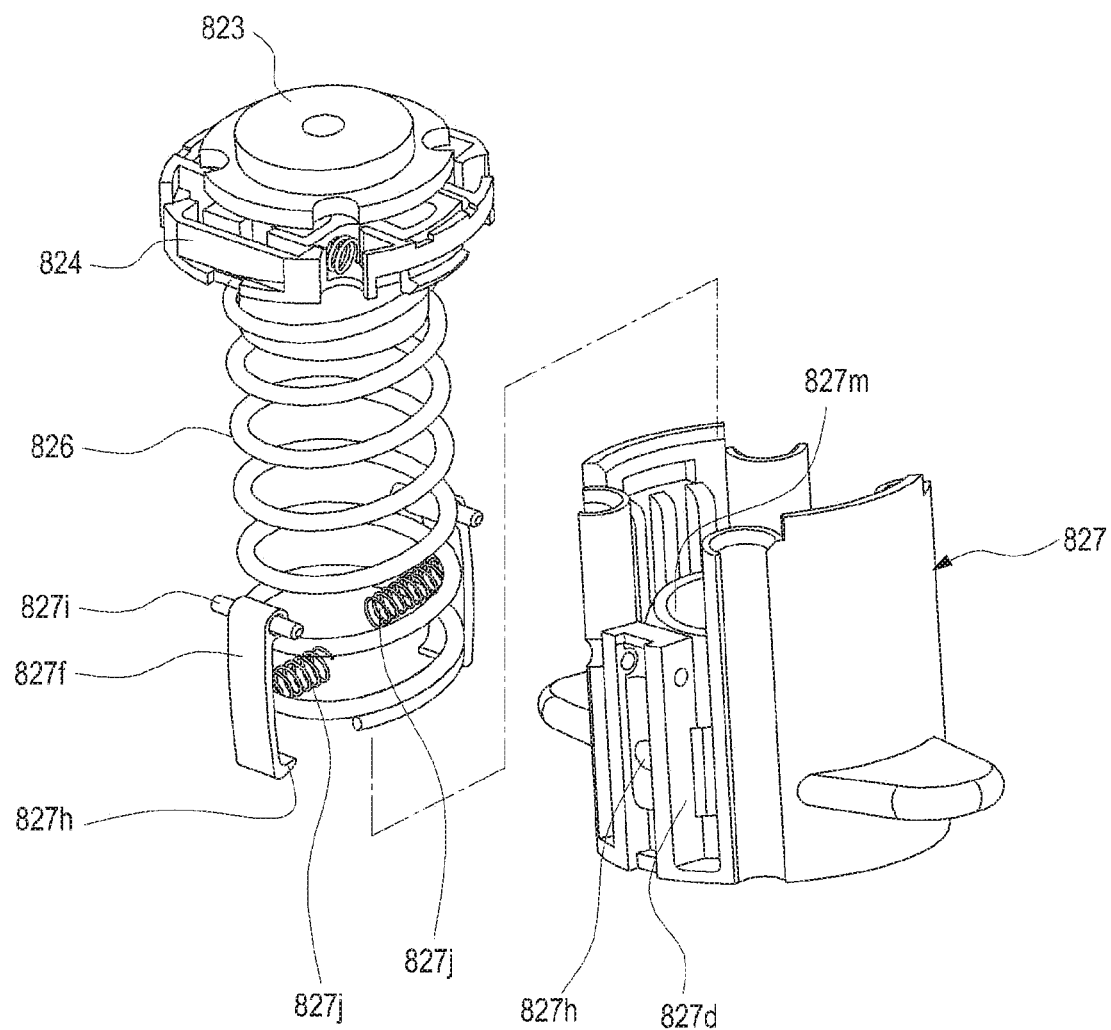
FIG. 51 is a perspective view illustrating an example where a main component of an attaching device of a wearable electronic device is partially separated according to an embodiment of the present disclosure.
Figure 52:
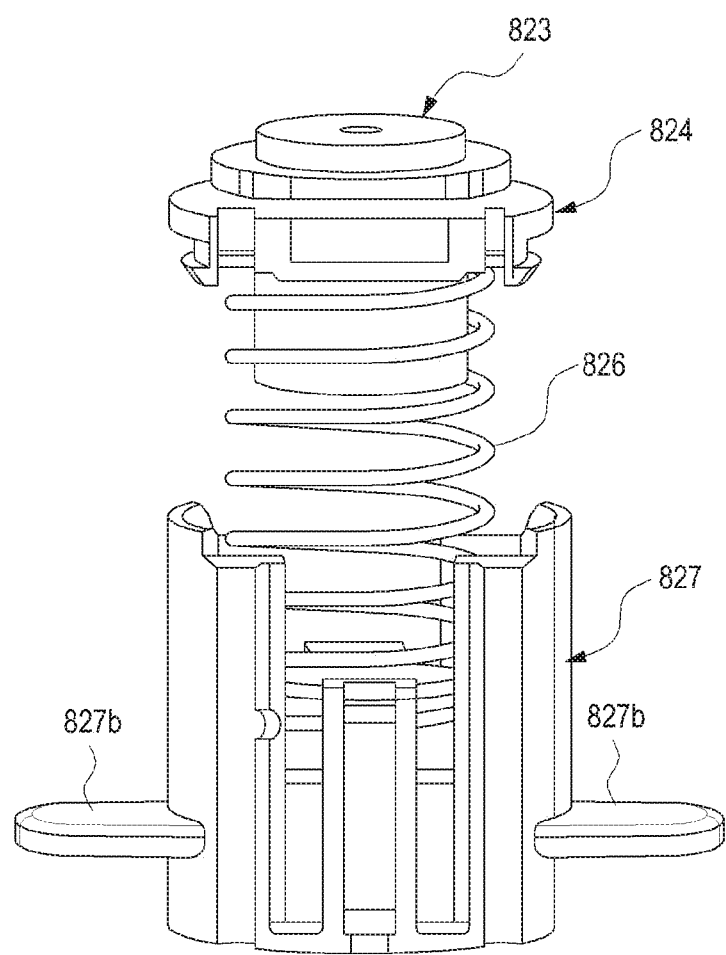
FIG. 52 is a perspective view illustrating an example where a main component of an attaching device of a wearable electronic device is partially coupled according to an embodiment of the present disclosure.

FIG. 46 is an exploded perspective view illustrating an attaching device of a wearable electronic device including a first housing according to an embodiment of the present disclosure. FIG. 47 is a plan view illustrating a hooking unit of a wearable electronic device according to an embodiment of the present disclosure. FIG. 48 is a perspective view illustrating a coupling unit of a wearable electronic device separated from a moving unit according to an embodiment of the present disclosure. FIG. 49 is a front view illustrating a coupling unit of a wearable electronic device separated from a moving unit according to an embodiment of the present disclosure. FIG. 50 is a perspective view illustrating a second housing of a wearable electronic device according to an embodiment of the present disclosure. FIG. 51 is a perspective view illustrating an example where a main component of an attaching device of a wearable electronic device is partially separated according to an embodiment of the present disclosure. FIG. 52 is a perspective view illustrating an example where a main component of an attaching device of a wearable electronic device is partially coupled according to an embodiment of the present disclosure.

Referring to FIGS. 46 to 52, the attaching device 820 of the wearable electronic device includes housings 821 and 822, a moving unit 827, a hooking unit 824, a seating unit 825, a first elastic unit 826, a button unit 823, and a coupling unit.

The housings 821 and 822 include a first housing 821 and a second housing 822 coupled with the first housing 821 by a screw or adhesive to form a cylindrical shape so that the moving unit 827 moves back and forth in the housings 821 and 822. However, the housings 821 and 822 are formed in various shapes having a longitudinal direction so that the moving unit 827 may move in the housings 821 and 822 without being limited to the cylindrical shape. The second housing 822 includes first guide units 822c projecting inward of the second housing 822 along the longitudinal direction of the second housing 822, and the first guide units 822c guides the moving unit 827 to move back and forth inside the second housing 822.

The moving unit 827 includes an outer surface 827a corresponding to an inner surface of the housings 821 and 822, and the outer surface 827a of the moving unit 827 may slide on the inner surface of the housings 821 and 822. The moving unit 827 includes second guide units 827c shaped as holes corresponding to the first guide units 822c, and the moving unit 827 may be smoothly moved back and forth in the second housing 822. The moving unit 827 includes a handle unit 823c to be gripped by the user, and the second housing 822 includes a first area 822a surrounding the outside of the moving unit 827 and a second area 822b where the handle unit 823c projects. The second area 822b passes through the inside/outside of the second housing 822 along the longitudinal direction of the second housing 822, and as the handle unit 823c moves along the longitudinal direction of the second housing 822, the handle unit 823c may be exposed to the outside of the second housing 827.

The hooking unit 824 is provided in the first housing 821 and includes a first hooking unit 824a, a first protrusion 824b, a second hooking unit 824c, a second protrusion 824d, second elastic units 824e and 824h, and inclined holes 824k and 824m having inclined surfaces 8241 and 824n. The first protrusion 824b projects from the first hooking unit 824a. The second hooking unit 824c is formed symmetrically with the first hooking unit 824a and may be spaced apart from the first hooking unit 824a by a first distance dl. The second protrusion 824d projects from the second hooking unit 824b and is formed symmetrically with the first protrusion 824b. The first hooking unit 824a includes a pair of second guide units 824f and 824i, and the second hooking unit 824c includes a pair of third guide units 824g and 824j facing the pair of second guide units 824*f* and 824*i*. The second elastic units 824*e* and 824*h* are provided between the second guide units 824*f* and 824*i* and the third guide units 824*g* and 824*j* and provide an elastic force to the first hooking unit 824*a* and the second hooking unit 824*c* so that the first hooking unit 824*a* and the second hooking unit 824*c* are separate from each other.

Although the second elastic units 824*e* and 824*h* are formed of springs, embodiments of the present disclosure are not limited thereto, and the second elastic units 824*e* and 824*h* may be differently formed to provide an elastic force to the first hooking unit 824*a* and the second hooking unit 824*c*. The inclined holes 824*k* and 824*m* are formed in the first hooking unit 824*a* and the second hooking unit 824*c*, respectively, and include inclined surfaces 8241 and 824*n*.

The seating unit 825 is provided in the first housing 821 and includes a first seating unit 825*a* where the hooking unit 825 is seated and a fourth guide unit 825*b* for guiding the first elastic unit 825*b*.

The first elastic unit 826 is provided between the moving unit 827 and the hooking unit 824 and is formed of a spring. The first elastic unit 826 is guided by the fourth guide unit 825*b* formed in the seating unit 825 and guided by a fifth guide unit 827*m* formed in the moving unit 827. The first elastic unit 826 provides an elastic force between the seating unit 825 and the moving unit 827.

The button unit 823 includes a first button unit 823*a* passing through a first hole formed in the first housing 821, a second button unit 823*b* provided in the first housing 821, and a third button unit 823*c* projecting from the bottom of the first button unit 823. The first button unit 823*a* moves along the first hole by an external force, and the second button unit 823*a* is projected along a side surface of the first button unit 823*a* to prevent the first button unit 823*a* from departing from the first hole. A unit of the third button unit 823*c* is formed to be inclined to correspond to the inclined surfaces 8241 and 824*n* of the hooking unit 824, and the third button unit 823*c* is inserted into the inclined holes 824*k* and 824*m* while abutting the inclined surfaces 8241 and 824*n*.

The coupling unit includes supports 827*d* formed in the moving unit 827, first rotating holes 827*e* formed in the supports 827*d*, a rotating unit 827*f* provided between the first rotating holes 827*e*, a rotating shaft 827*i* connecting the first rotating holes 827*e* with the rotating part 827, and a fixing unit 827*h* detachably coupled with the wearable electronic device.

The supports 827*d* provides a space where the rotating unit 827*f* is received. The rotating unit 827*f* includes a second rotating hole 827*g* corresponding to the first rotating hole 827*e*, and the rotating shaft 827*i* is inserted into the first rotating holes 827*e* and the second rotating hole 827*g*. The rotating unit 827*f* rotates about the rotating shaft 827*i*. The fixing unit 827*h* projects from an end of the rotating unit 827*f*.

Figure 53:
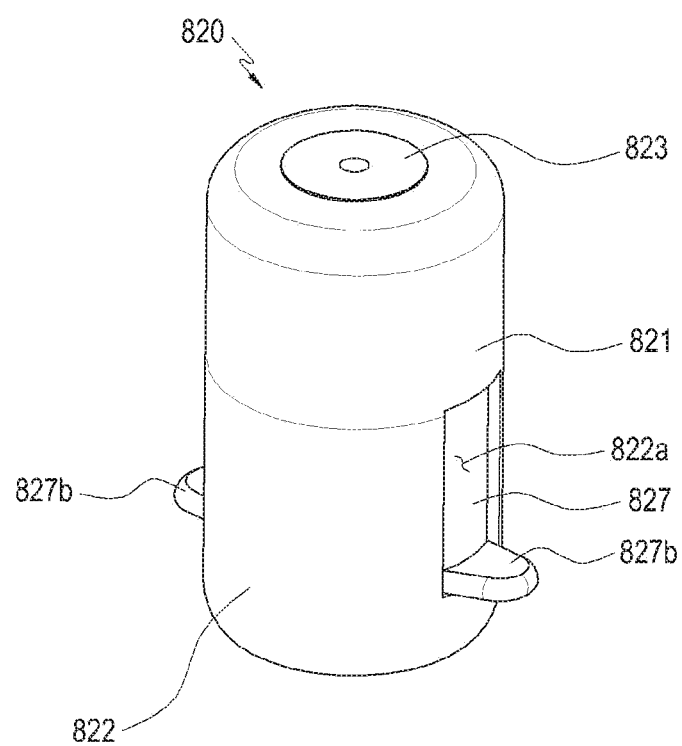
FIG. 53 is a perspective view illustrating an example where an attaching device of a wearable electronic device is coupled according to an embodiment of the present disclosure.
Figure 54:
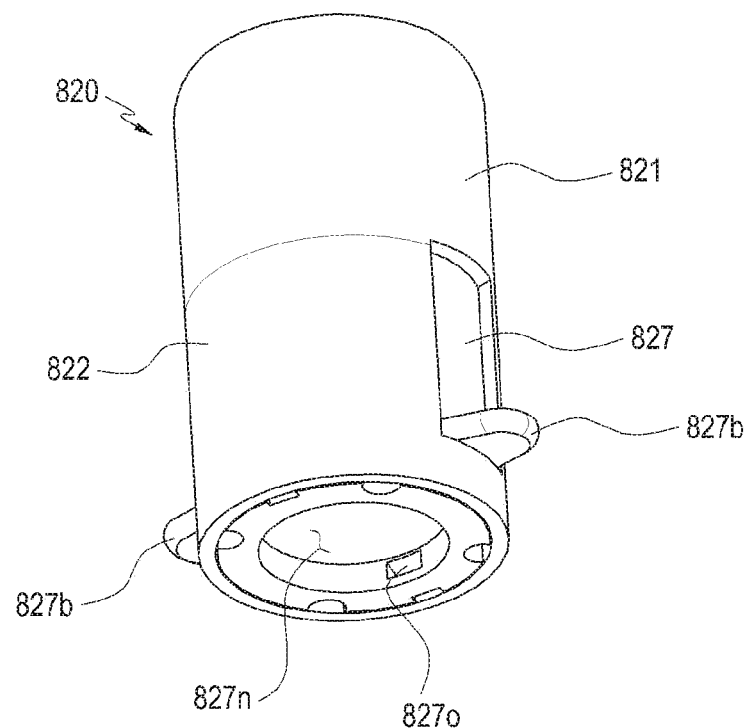
FIG. 54 is a perspective view illustrating an attaching device of a wearable electronic device in a different direction according to an embodiment of the present disclosure.
Figure 55:
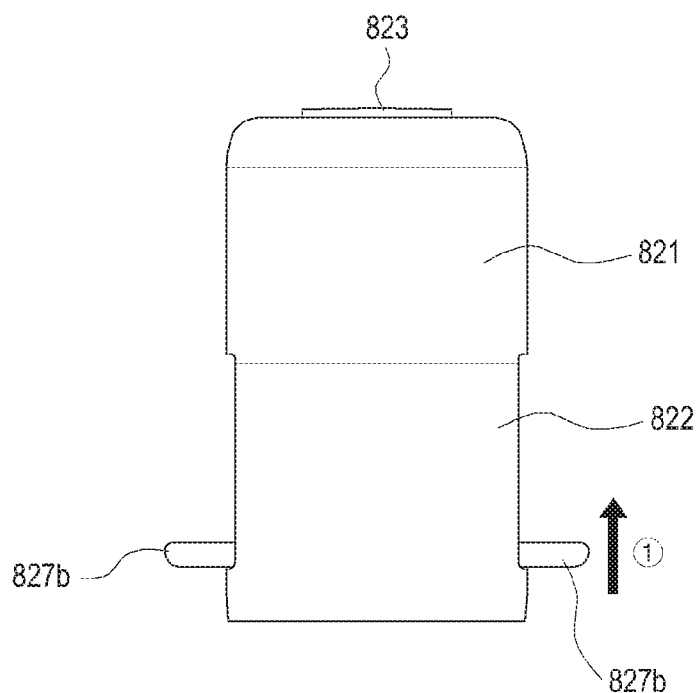
FIG. 55 is a side view illustrating an attaching device of a wearable electronic device according to an embodiment of the present disclosure.
Figure 56:
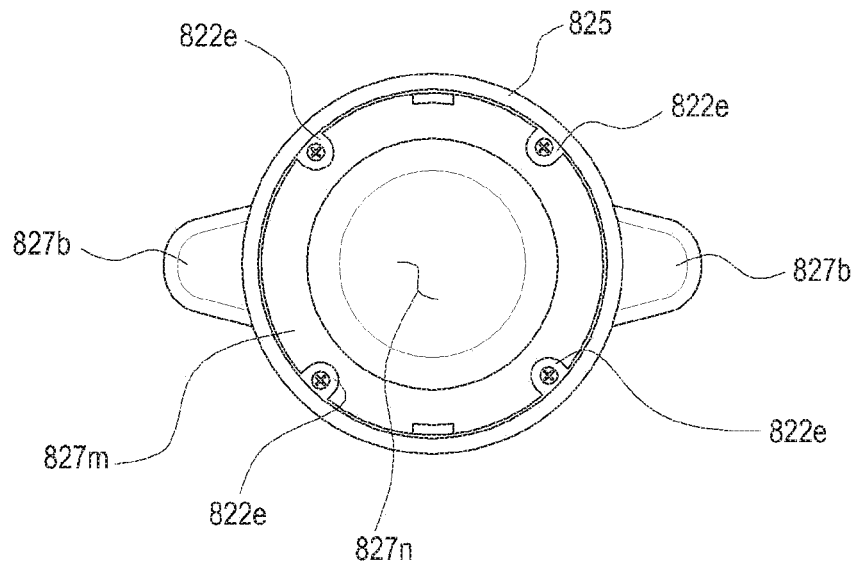
FIG. 56 is a bottom view illustrating an attaching device of a wearable electronic device according to an embodiment of the present disclosure.

FIG. 53 is a perspective view illustrating an attaching device of a wearable electronic device according to an embodiment of the present disclosure. FIG. 54 is a perspective view illustrating an attaching device of a wearable electronic device in a different direction according to an embodiment of the present disclosure. FIG. 55 is a side view illustrating an attaching device of a wearable electronic device according to an embodiment of the present disclosure. FIG. 56 is a bottom view illustrating an attaching device of a wearable electronic device according to an embodiment of the present disclosure.

Referring to FIGS. 53 to 56, the attaching device 820 of the wearable electronic device includes a receiving unit 827*n* for receiving the wearable electronic device.

The receiving unit 827*n* is provided in the form of a hole in the lower surface of the moving unit 827, and the wearable electronic device is received in the receiving unit 827*n*. A hole 827*o* is formed in a side surface of the receiving unit 827*n*, and as the fixing unit 827*h* of the coupling unit projects through the hole 827*o* to the internal space of the receiving unit 827*n*, the wearable electronic device is fastened to the receiving unit 827*n*.

An end of the second housing 827 includes protrusions 822*e* projecting towards the receiving unit 827*n* so that the moving unit 827 is locked to the protrusions 822*e* and prevented from releasing to the outside of the second housing 827.

Figure 57:
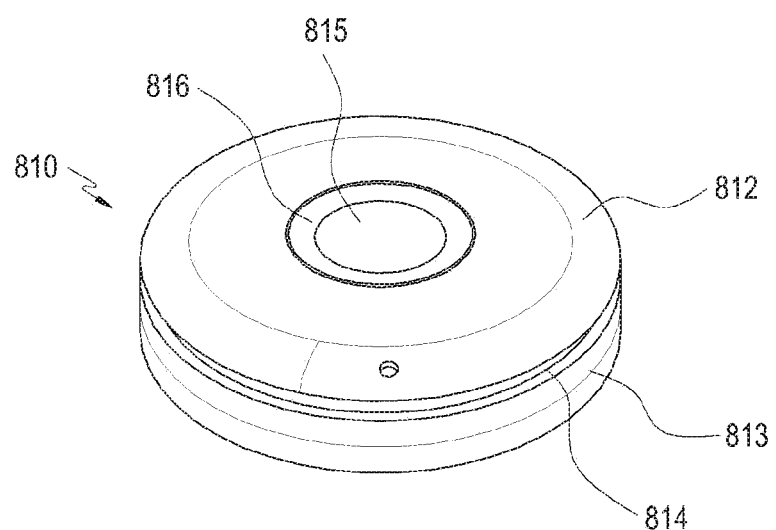
FIG. 57 is a perspective view illustrating a wearable electronic device according to an embodiment of the present disclosure.
Figure 58:
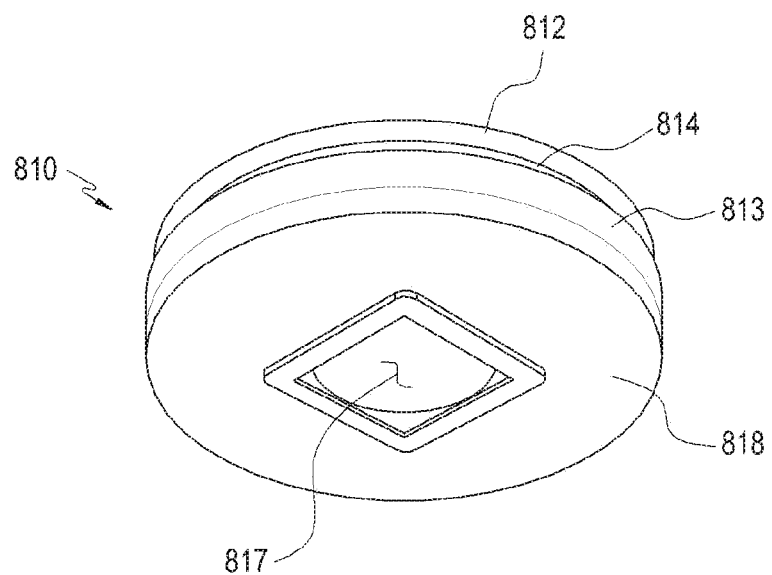
FIG. 58 is a perspective view illustrating a wearable electronic device in a different direction according to an embodiment of the present disclosure.

FIG. 57 is a perspective view illustrating a wearable electronic device according to an embodiment of the present disclosure. FIG. 58 is a perspective view illustrating a wearable electronic device in a different direction according to an embodiment of the present disclosure.

Referring to FIGS. 57 and 58, the wearable electronic device 810 includes a first main body 812 and a second main body 813 detachably coupled to the first main body 812 and includes a shape corresponding to the receiving unit 827*n* shown in FIG. 54 to be received in the receiving unit 827*n*.

A coupling hole 814 is formed in a side surface of the first main body 812, and the fixing unit 827*h* projecting through the hole 827*o* is locked to the coupling hole 814. The coupling hole 814 is formed along the side surface of the first main body 812. However, the coupling hole 814 has a shape corresponding to the fixing unit 827*h* without being limited to being formed along the side surface of the first main body 812. As the fixing unit 827*h* is stuck to the coupling hole 814, the wearable electronic device 810 remains fixed to the receiving unit 827*n*. The coupling hole 814 is formed in a side surface of the second main body 814 instead of in the side surface of the first main body 812.

A power button 815 is formed on a surface of the first main body 812 to power on/off the wearable electronic device. An illumination unit 816 is formed around the power button 815. The illumination unit 816 is formed of a light emitting diode (LED), but the present disclosure is not limited thereto.

The second main body 813 is detachably coupled with the first main body 812, and together form an outer shape and include the sensor unit 811, circuit board, and battery. An opening unit 817 is formed in a surface of the second main body 814, and the micro needles of the sensor unit 811 may be exposed to the outside of the second main body 813 through the opening unit 817.

A sticky pad is attached to a surface of the second main body 813 to attach the wearable electronic device 810 to the user's body through the pad.

Figure 59:
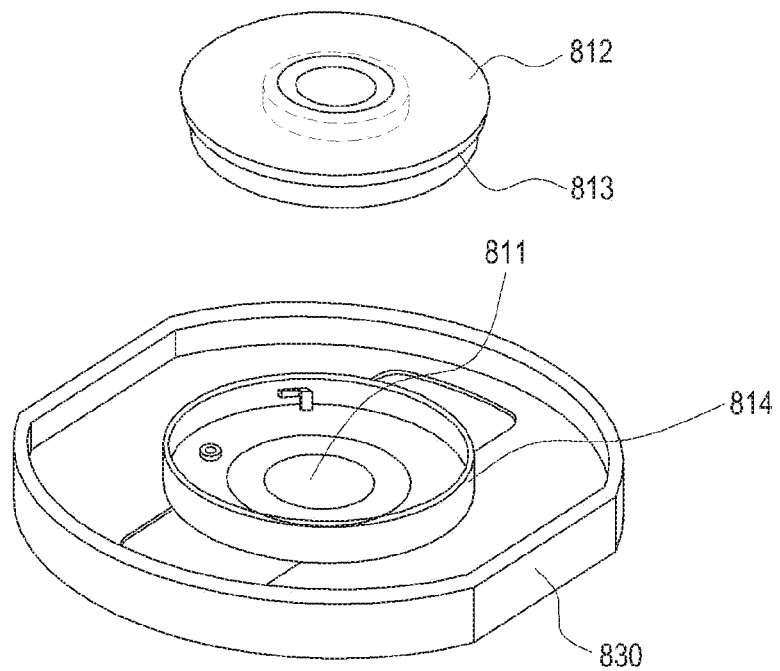
FIG. 59 illustrates a wearable electronic device received in a protecting case according to an embodiment of the present disclosure.
Figure 60:
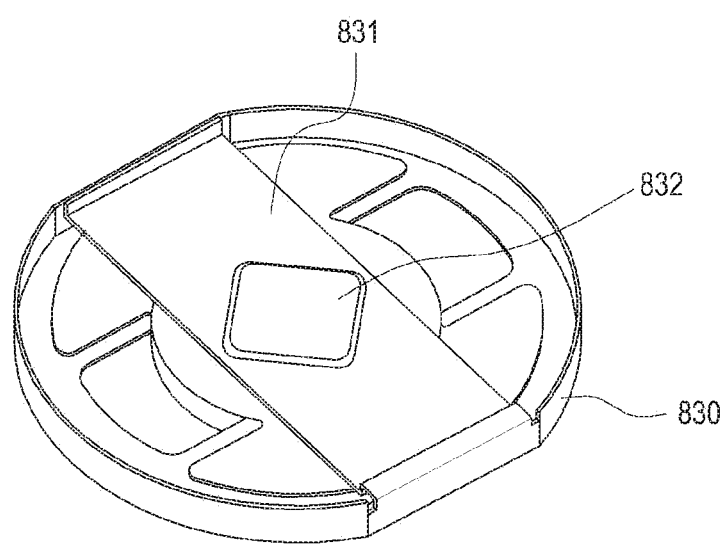
FIG. 60 is a rear perspective view illustrating a protecting case according to an embodiment of the present disclosure.
Figure 61:
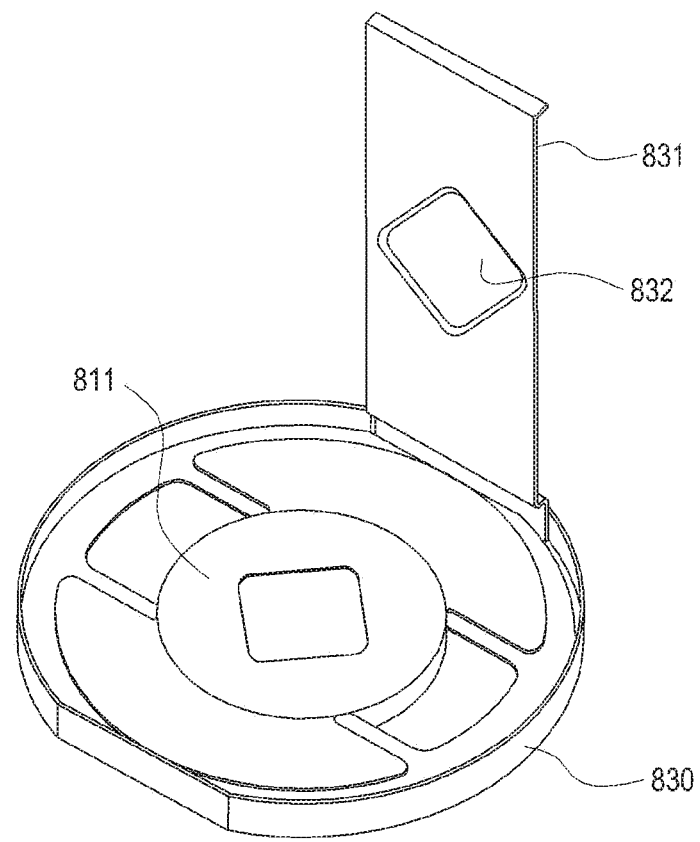
FIG. 61 illustrates a rear cover of a protecting case opened according to an embodiment of the present disclosure.

FIG. 59 illustrates a wearable electronic device received in a protecting case according to an embodiment of the present disclosure. FIG. 60 is a rear perspective view illustrating a protecting case according to an embodiment of the present disclosure. FIG. 61 illustrates a rear cover of a protecting case opened according to an embodiment of the present disclosure.

Referring to FIGS. 59 and 61, the protecting case 830 receives the second housing 814 and protects the sensor unit 811 mounted in the second housing 814.

As the second housing 814 is press-fittingly coupled to the protecting case 830, the second housing 814 may be pulled by an external force, so that the second housing 814 may be separated from the protecting case 830. The protecting case 830 includes a rear cover 831 coupled to rotate on a side surface of the protecting case 830 while protecting the sensor unit 811 mounted in the protecting case 830. The rear cover 831 includes a protrusion 832 corresponding in shape to the protrusion of the sensor unit 811, and the protrusion 832 protects the micro needles of the sensor unit 811 from the outside.

As such, the protecting case 830 protects the sensor unit of the wearable electronic device 810 from the outside, preventing damage to the micro needles.

The protecting case 830 is formed to have an opened side and to have a shape corresponding to the bottom 827*m* of the attaching device of the wearable electronic device.

Figure 62:
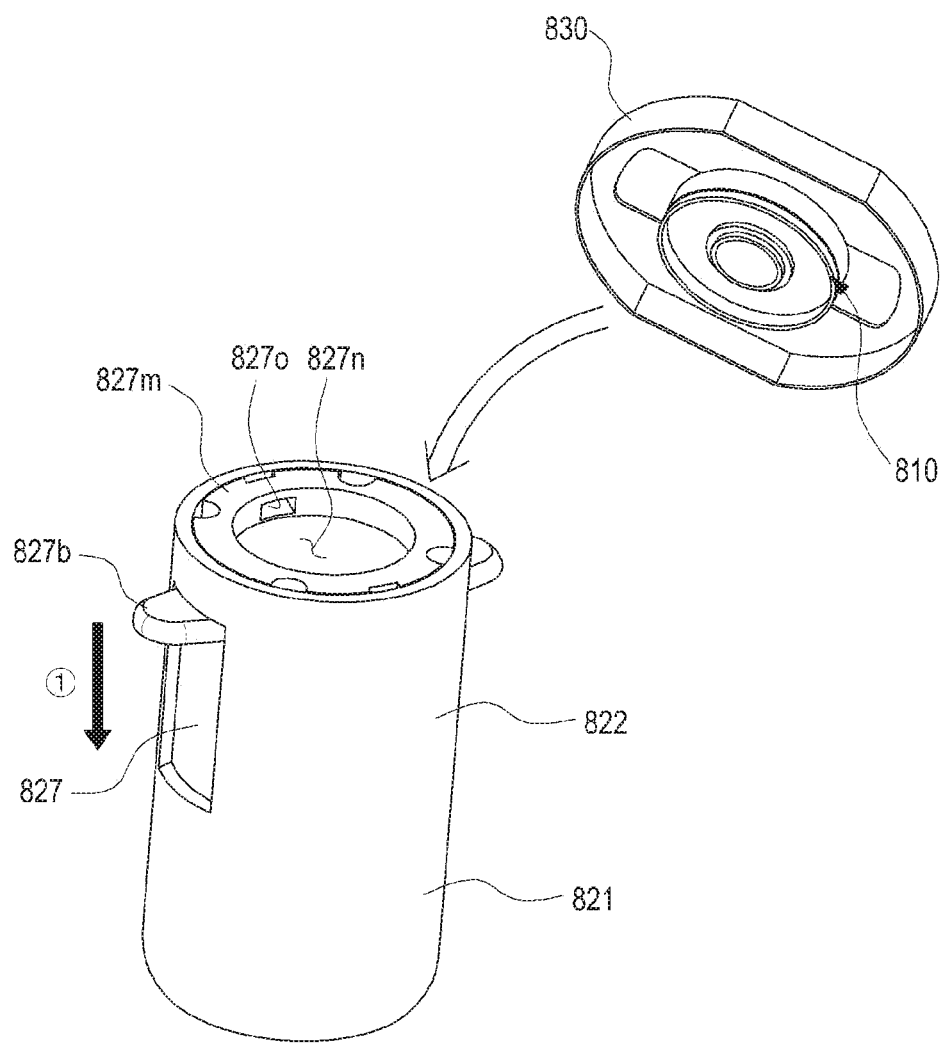
FIG. 62 illustrates a wearable device received in an attaching device thereof according to an embodiment of the present disclosure.

FIG. 62 illustrates a wearable device received in an attaching device thereof according to an embodiment of the present disclosure.

Referring to FIG. 62, the wearable electronic device 810 is received in the receiving unit 827*n* while accommodated in the protecting case 830, which is seated on the bottom 827*m* of the wearable electronic device.

As the handle unit 827*b* is moved along a first direction ①, the wearable electronic device 810 moves along the first direction ① while coupled with the receiving unit 827*n*. The wearable electronic device 810 may be separated from the protecting case 830. The process in which the wearable electronic device 810 is received in the receiving unit 827*n* will now be described below in greater detail.

Figure 63:
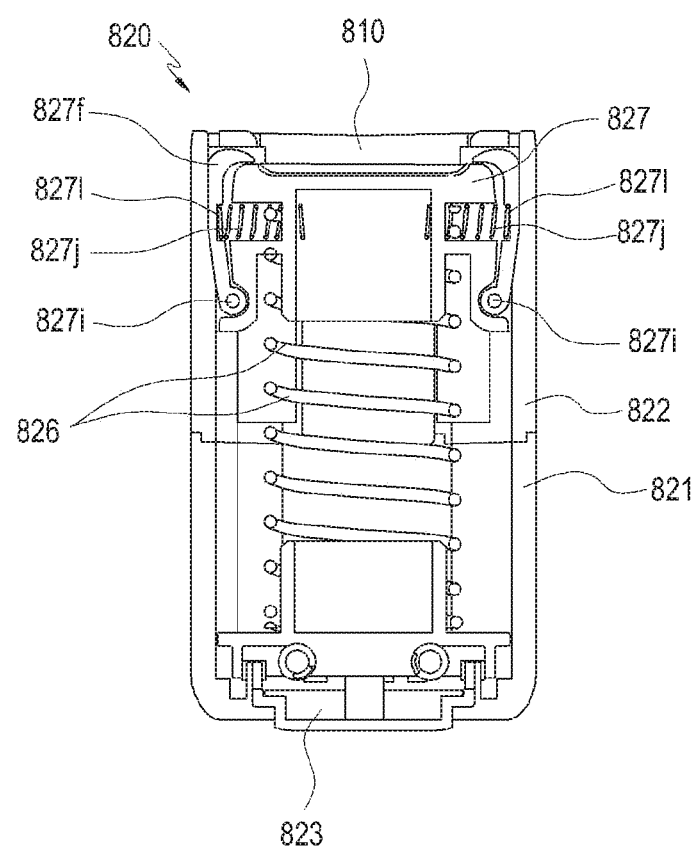
FIG. 63 is a cross-sectional view illustrating an attaching device of a wearable electronic device according to an embodiment of the present disclosure.
Figure 64:
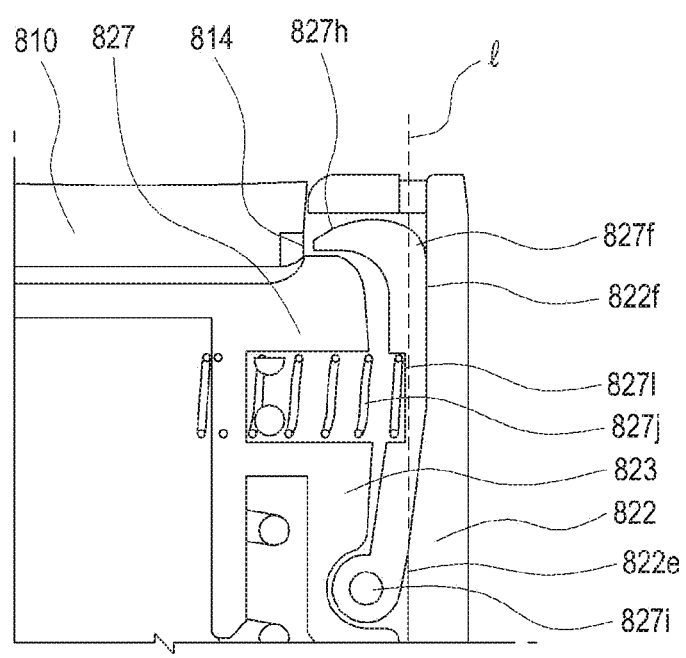
FIG. 64 is a cross-sectional view illustrating a main unit of an attaching device of a wearable electronic device according to an embodiment of the present disclosure.
Figure 65:
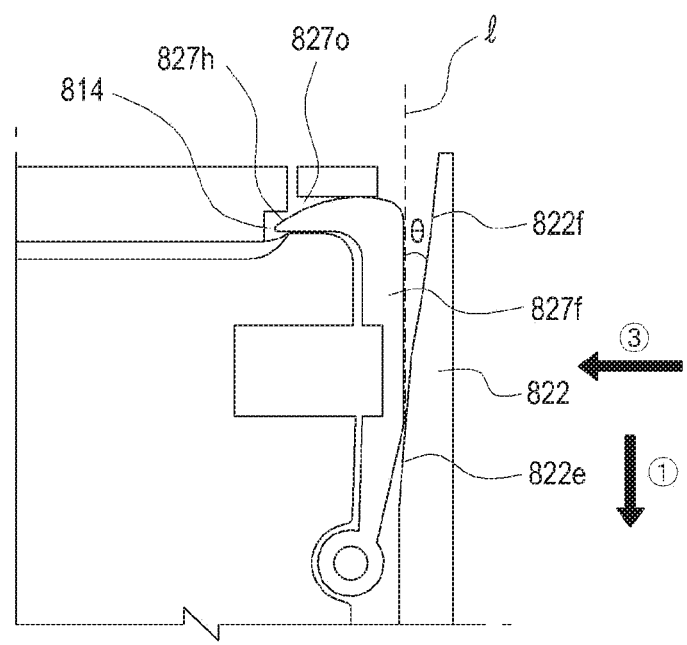
FIG. 65 is a cross-sectional view illustrating an example where a coupling unit of a wearable electronic device is hooked to the wearable electronic device according to an embodiment of the present disclosure.

FIG. 63 is a cross-sectional view illustrating an attaching device of a wearable electronic device according to an embodiment of the present disclosure. FIG. 64 is a cross-sectional view illustrating a main unit of a wearable electronic device according to an embodiment of the present disclosure. FIG. 65 is a cross-sectional view illustrating an example where a coupling unit of a wearable electronic device is hooked to the wearable electronic device according to an embodiment of the present disclosure.

The rotating unit 827*f* is provided between the second housing 822 and the moving unit 827 to rotate about the hinge shaft 827*i*. The moving unit 827 includes a third elastic unit 827*j*, such as a spring. The third elastic unit 827*j* provides an elastic force to bring the rotating unit 827*f* in tight contact with the inner surface of the second housing 822. The rotating unit 827*f* includes a hole 8271 corresponding to an end of the third elastic unit 827*j*, and the end of the third elastic unit 827*j* is inserted into the hole 8271. Accordingly, the rotating unit 827*f* is brought in tight contact with the inner surface of the second housing 822 by an elastic force of the third elastic unit 827*j*.

The inner surface of the second housing 822 includes a first inner surface 822*f* positioned adjacent to an end of the second housing 822 and a second inner surface 822*e* provided in a central area of the second housing 822. The first inner surface 822*f* is formed to be depressed in a direction outside the second housing 822 to be inclined about the second inner surface 822*e*. For example, the second inner surface 822*e* is formed to be flat, and the first inner surface 822*f* is formed to have a predetermined slope θ with respect to a line extending from the second inner surface 822*e*.

As the moving unit 827 is moved in a first direction ① with the wearable electronic device 810 received in the receiving unit 827*n*, the rotating unit 827*f* moves in the first direction ① along with the moving unit 827. As the rotating unit 827*f* is moved from the first inner surface 822*f* along the second inner surface 822*e*, the rotating unit 827*f* is rotated in a direction ③ inside the second housing 822. The fixing unit 827*h* is projected through the hole 827*o* and fastened to the coupling hole 814 of the wearable electronic device. Accordingly, the wearable electronic device 810 moves along the first direction ① while received in the receiving unit 827*n*.

Figure 66:
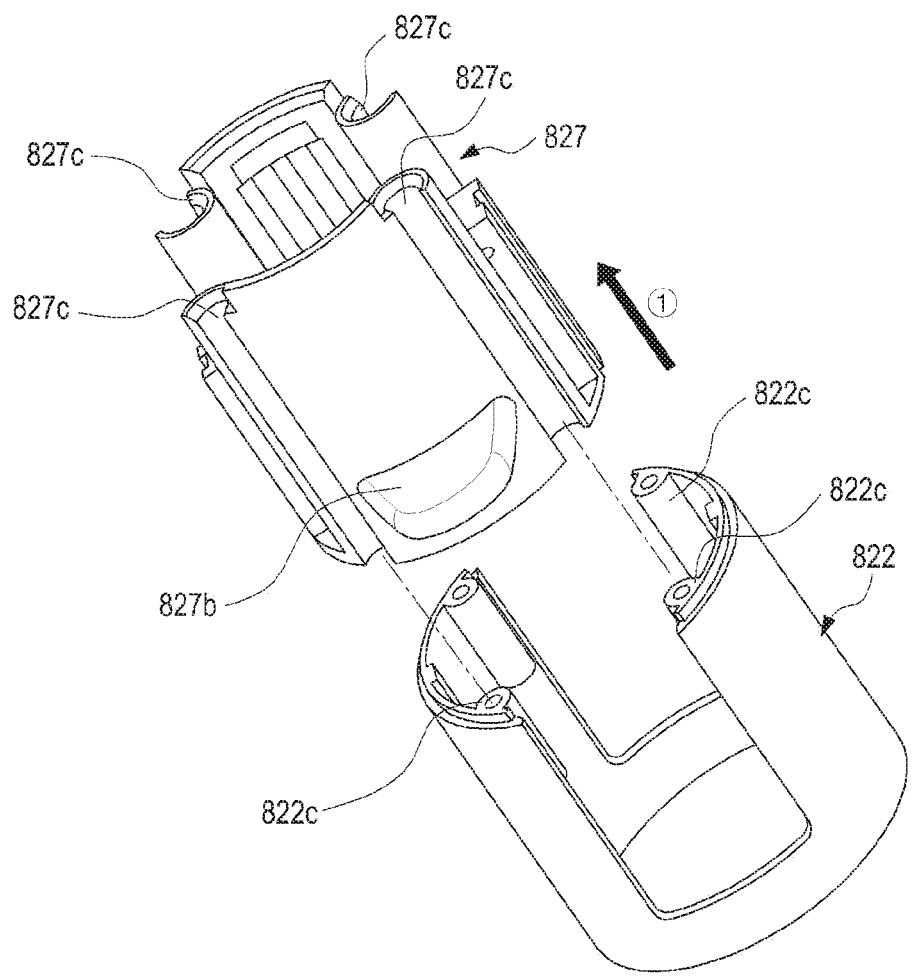
FIG. 66 is a perspective view illustrating an example where a moving unit of an attaching device of a wearable electronic device moves in a second housing according to an embodiment of the present disclosure.

FIG. 66 is a perspective view illustrating an example where a moving unit of an attaching device of a wearable electronic device moves in a second housing according to an embodiment of the present disclosure.

Referring to FIGS. 52 and 66, as the moving unit 827 is moved in the first direction from the second housing 822, the first elastic unit 826 is compressed between the seating unit 824 and the moving unit 827 to accumulate elastic energy.

Figure 67:
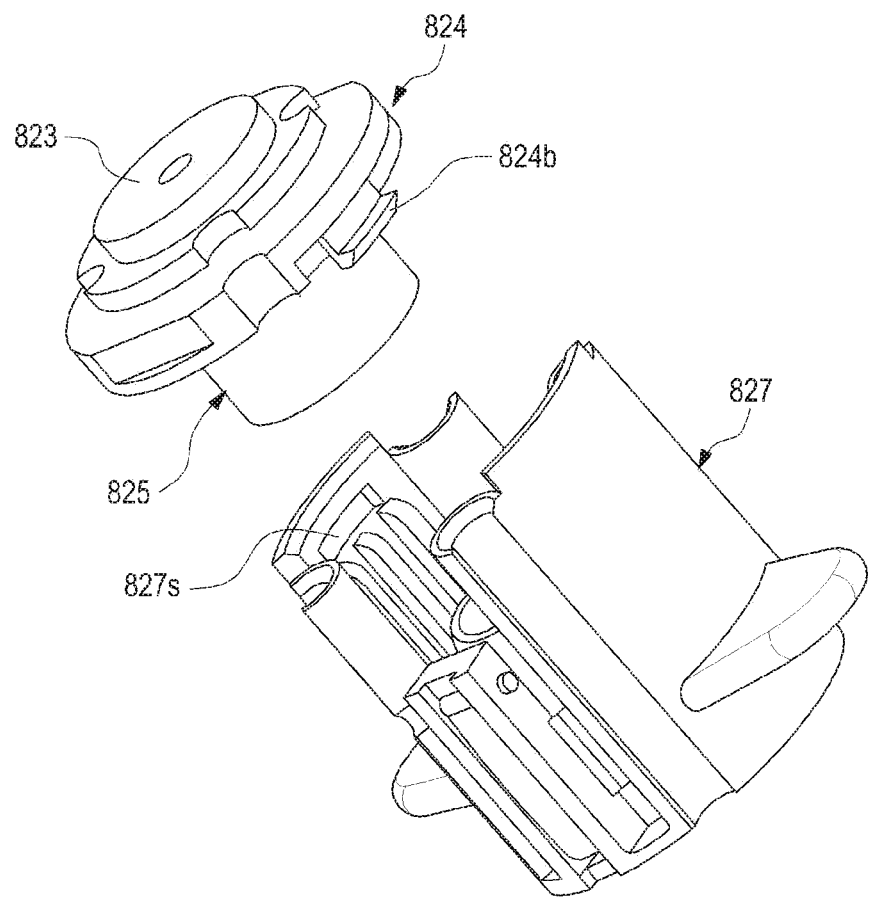
FIG. 67 is a perspective view illustrating a moving unit and hooking unit of an attaching device of a wearable electronic device according to an embodiment of the present disclosure.
Figure 68:
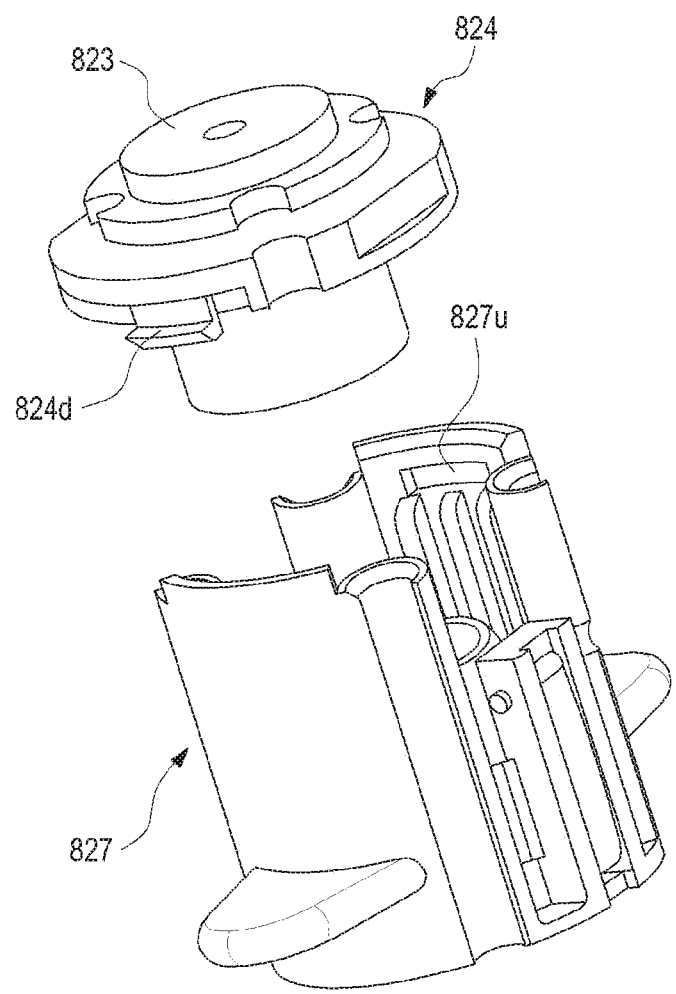
FIG. 68 is a perspective view illustrating a moving unit and hooking unit of an attaching device of a wearable electronic device in a different direction according to an embodiment of the present disclosure.
Figure 69:
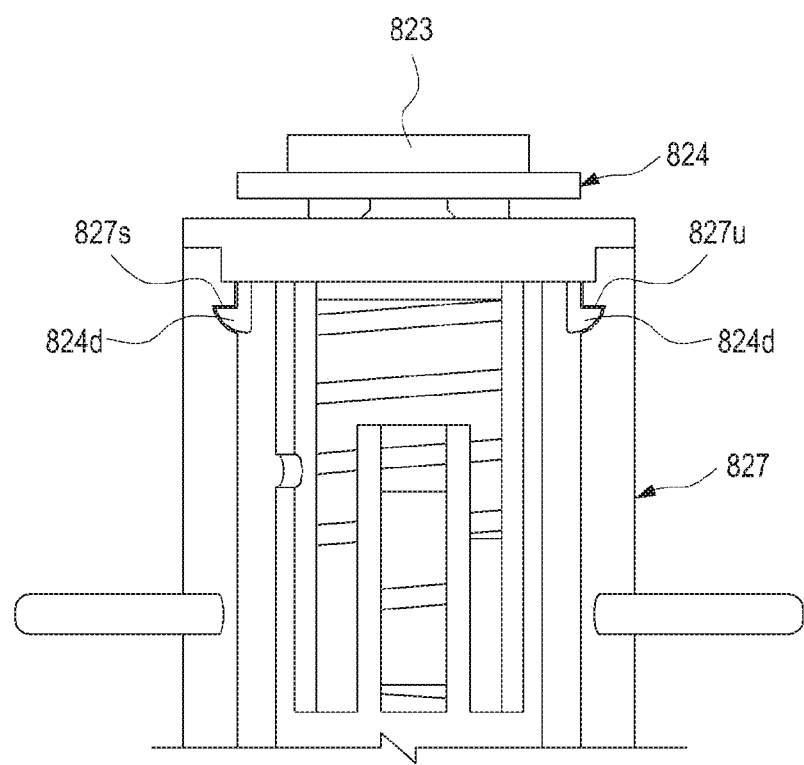
FIG. 69 is a cross-sectional view illustrating an example where a hooking unit and moving unit of an attaching device of a wearable electronic device are coupled according to an embodiment of the present disclosure.

FIG. 67 is a perspective view illustrating a moving unit and hooking unit of an attaching device of a wearable electronic device according to an embodiment of the present disclosure. FIG. 68 is a perspective view illustrating a moving unit and hooking unit of an attaching device of a wearable electronic device in a different direction according to an embodiment of the present disclosure. FIG. 69 is a cross-sectional view illustrating an example where a hooking unit and moving unit of an attaching device of a wearable electronic device are coupled according to an embodiment of the present disclosure.

Referring to FIGS. 67 to 69, the moving unit 827, after moved to the inside of the first housing 821, is coupled and fastened to the hooking unit 824.

The moving unit 827 includes a first hooking hole 827*u* coupled to the first protrusion 824*b* and a second hooking hole 827*s* coupled to the second protrusion 824*d*. As the moving unit 827 is moved in the first direction, the first protrusion 824*b* and the second protrusion 824*d* are locked to the first hooking hole 827*u* and the second hooking hole 827*s*, respectively. The first hooking unit 824*a* and the second hooking unit 824*c* remain away from each other by the elastic force of the second elastic units 824*e* and 824*h*. As the moving unit 827 is coupled and fastened to the hooking unit 824, the first elastic unit 826 maintains an elastic force.

Figure 70:
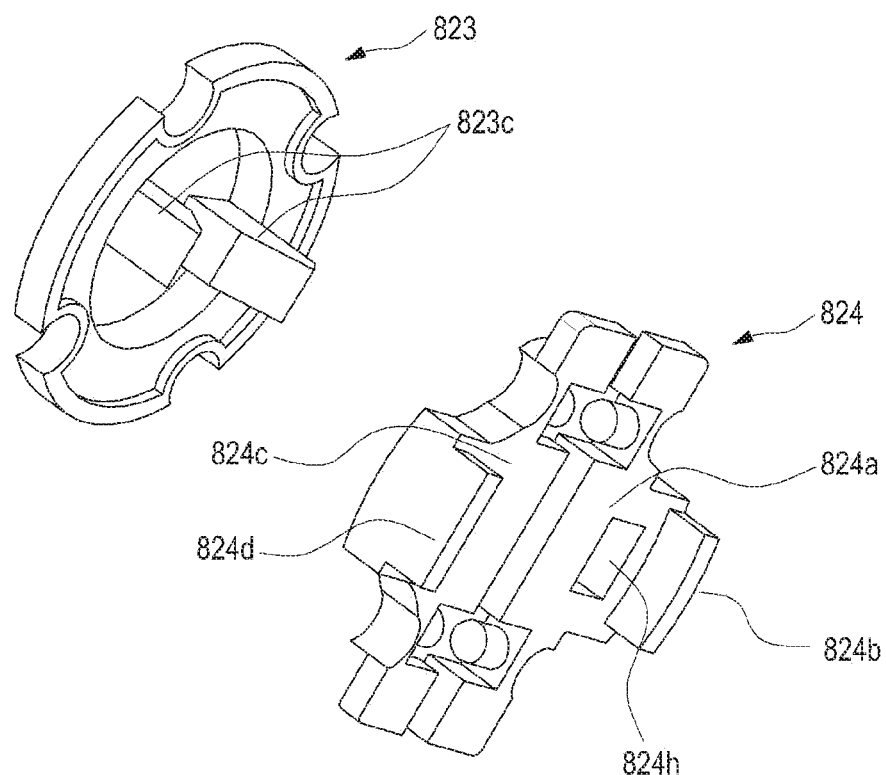
FIG. 70 is an exploded perspective view illustrating a button unit and hooking unit of a wearable electronic device according to an embodiment of the present disclosure.
Figure 71:
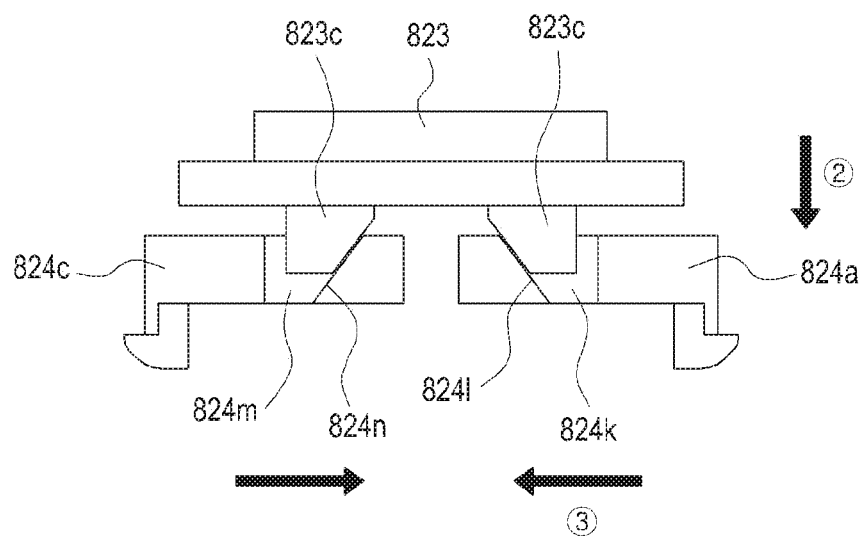
FIG. 71 is a cross-sectional view illustrating an example where a button unit of a wearable electronic device operates on a hooking unit according to an embodiment of the present disclosure.
Figure 72:
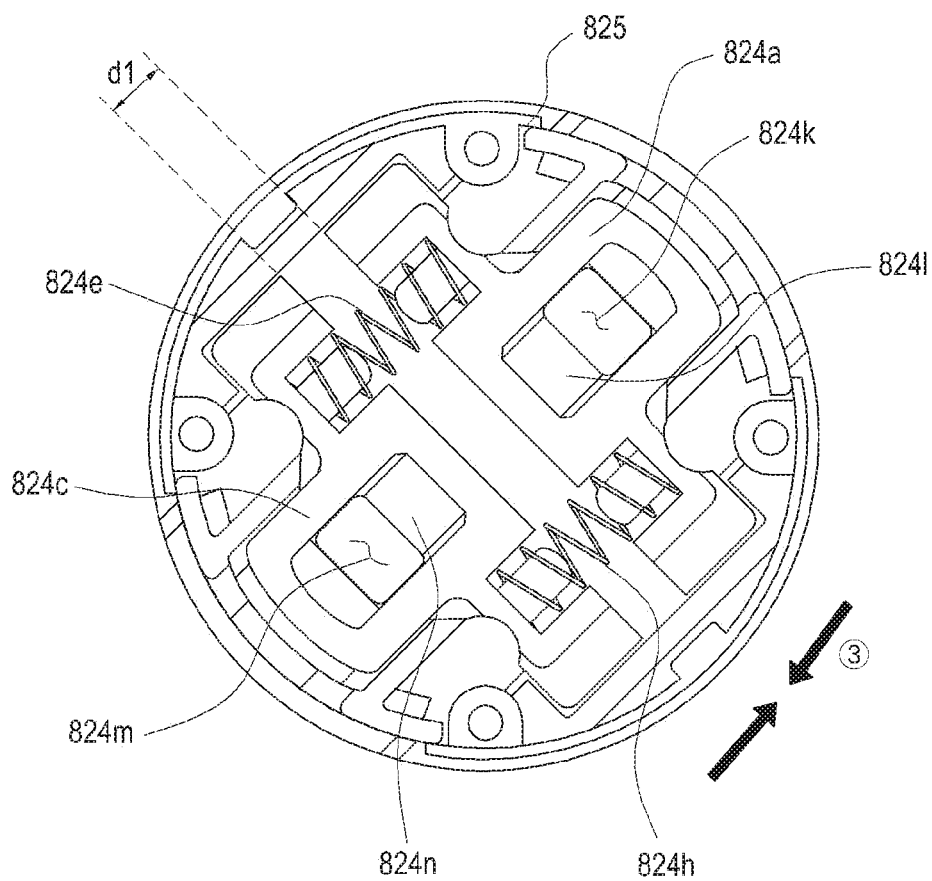
FIG. 72 is a plan view illustrating an example where a hooking unit of a wearable electronic device operates according to an embodiment of the present disclosure.
Figure 73:
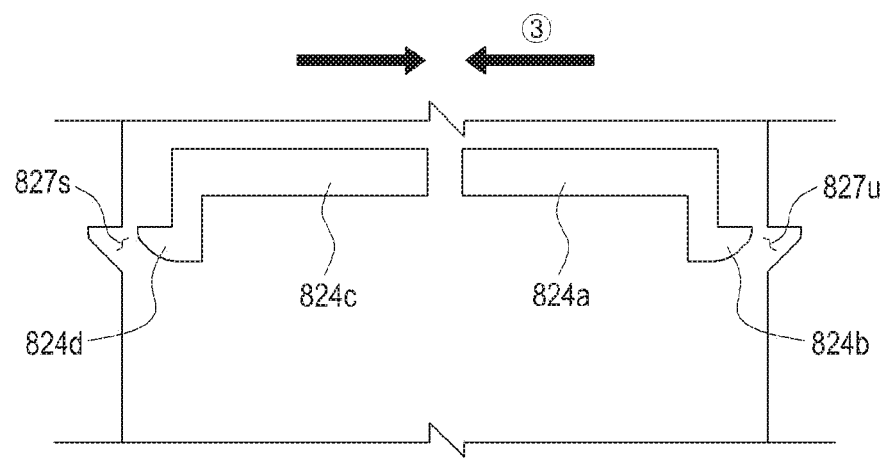
FIG. 73 is a cross-sectional view illustrating an example where a hooking unit and moving unit of a wearable electronic device are separated according to an embodiment of the present disclosure.

FIG. 70 is an exploded perspective view illustrating a button unit and hooking unit of a wearable electronic device according to an embodiment of the present disclosure. FIG. 71 is a cross-sectional view illustrating an example where a button unit of a wearable electronic device operates on a hooking unit according to an embodiment of the present disclosure.

The button unit 823 moves in a second direction, such as an opposite direction of the first direction, by an external force. The third button unit 823*c* may be rendered to abut the inclined surfaces 8241 and 824*n* as inserted into the inclined holes 824*k* and 824*m*. As the third button unit 823*c* is moved in the second direction ② and thus applies a force to the inclined surfaces 8241 and 824*n*, the first hooking unit 824*a* and the second hooking unit 824*c* move in the third direction ③ along which they approach. As the first hooking unit 824*a* and the second hooking unit 824*c* approach, the first protrusion 824*b* and the second protrusion 824*d* are separated from the first hooking hole 827*u* and the second hooking hole 827*s*, respectively. Accordingly, the moving unit 827 separates from the hooking unit 824.

Figure 74:
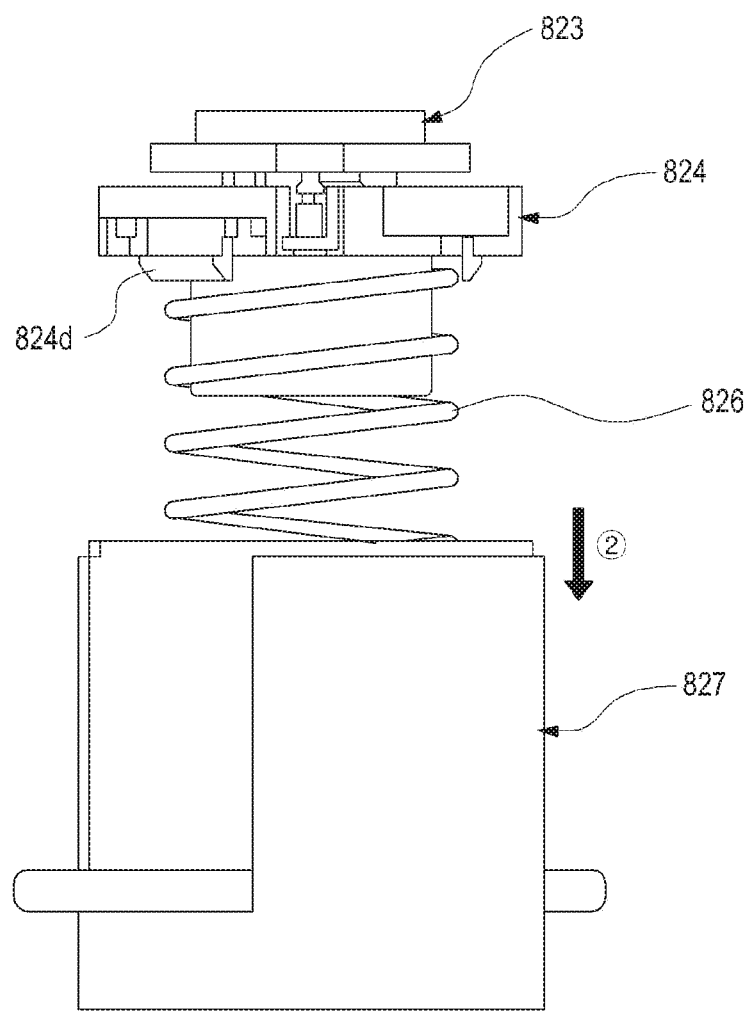
FIG. 74 is a perspective view illustrating an example where a moving unit of an attaching device of a wearable electronic device is moved according to an embodiment of the present disclosure.

FIG. 74 is a perspective view illustrating an example where a moving unit of an attaching device of a wearable electronic device is moved according to an embodiment of the present disclosure.

Specifically, FIG. 74 illustrates a process after the moving unit 827 has been separated from the hooking unit 824.

As the moving unit 827 is released from coupling with the hooking unit 824, the first elastic unit 826 provides an elastic force to the moving unit 827 in the second direction ②. The moving unit 827 may be accelerated in the second direction ② by the elastic force of the first elastic unit 826.

Figure 75:
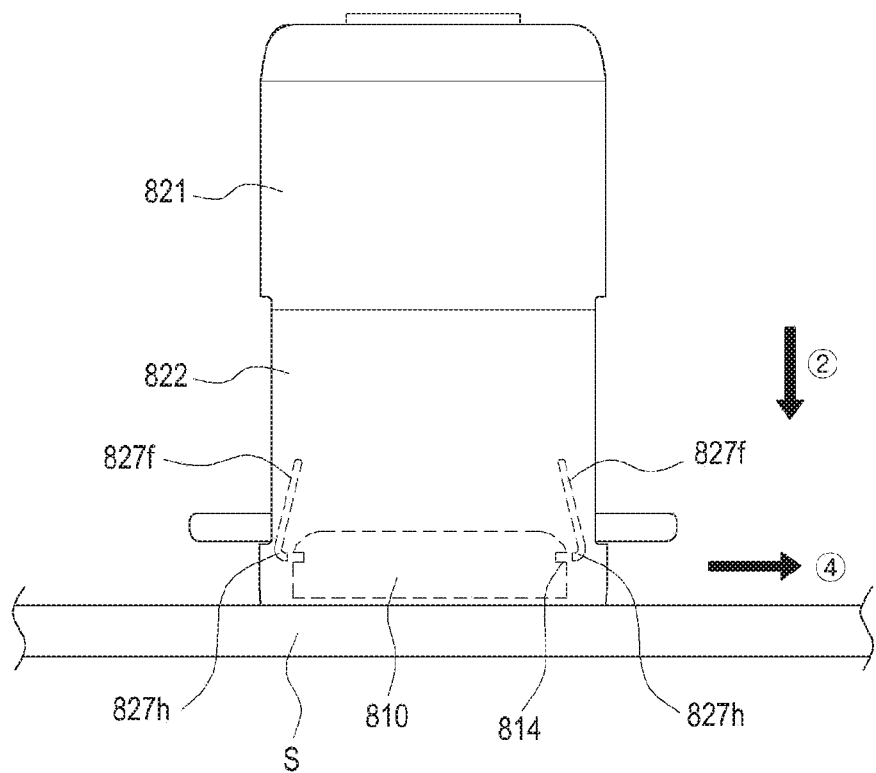
FIG. 75 is a cross-sectional view illustrating an example where a main body is separated in an attaching device of a wearable electronic device according to an embodiment of the present disclosure.

FIG. 75 is a cross-sectional view illustrating an example where a main body is separated in an attaching device of a wearable electronic device according to an embodiment of the present disclosure.

Referring to FIGS. 64, 65, and 75, as the moving unit 827 is moved in the second direction ② by the elastic force of the first elastic unit 826, the wearable electronic device 810 received in the receiving unit 827n may be accelerated in an opposite direction of the second direction ②. As the rotating unit 827f is moved from the second inner surface 822e to the first inner surface 822f, the rotating unit 827f is rotated while brought in tight contact with the first inner surface 822f by the elastic force of the third elastic unit 827j applied in a fourth direction ④, such as an opposite direction of the third direction. As the rotating unit 827f rotates, the fixing unit 827h is removed from the coupling unit 814 of the wearable electronic device 810. Accordingly, the wearable electronic device 810 is removed from the receiving unit 827n and may pressurize the user's skin (S) by the acceleration. That is, the micro needles of the wearable electronic device 810 are easily inserted into the user's skin (S) by the acceleration.

Figure 76:
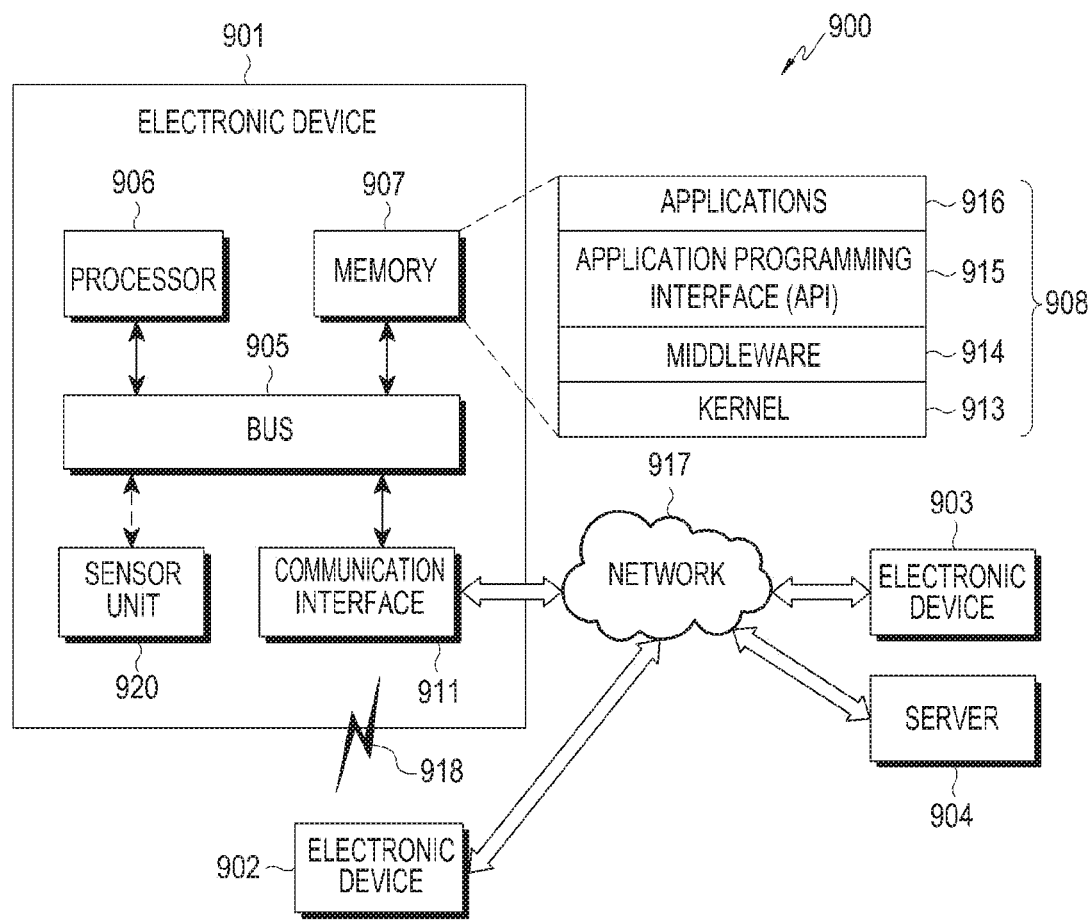
FIG. 76 illustrates a network environment where a wearable electronic device operates according to an embodiment of the present disclosure.

FIG. 76 illustrates a network environment where a wearable electronic device operates according to an embodiment of the present disclosure.

In FIG. 76, the wearable electronic device may be an electronic device 901. The wearable electronic device 901 interworks with various electronic devices 902, 903, and 904.

Examples of the electronic device includes at least one of a smartphone, a tablet personal computer (PC), a mobile phone, a video phone, an e-book reader, a desktop PC, a laptop computer, a netbook computer, a workstation, a personal digital assistant (PDA), a portable multimedia player (PMP), an MP3 player, a mobile medical device, a camera, or a wearable device such as smart glasses, a head-mounted device (HMD), electronic clothes, an electronic bracelet, an electronic necklace, an electronic appcessory, an electronic tattoo, a smart mirror, or a smart watch.

According to an embodiment of the present disclosure, the electronic device may be a smart home appliance such as a television, a digital video disk (DVD) player, an audio player, a refrigerator, an air conditioner, a cleaner, an oven, a microwave oven, a washer, a drier, an air cleaner, a set-top box, a home automation control panel, a security control panel, a TV box such as Samsung HomeSync™, Apple TV™, or Google TV™, a gaming console such as Xbox™ or PlayStation™, an electronic dictionary, an electronic key, a camcorder, or an electronic picture frame.

According to an embodiment of the present disclosure, the electronic device includes at least one of various portable medical measuring devices such as a body substance analyzer, a blood sugar measuring device, a heartbeat measuring device, or a body temperature measuring device, a magnetic resource angiography (MRA) device, a magnetic resource imaging (MM) device, a computed tomography (CT) device, an imaging device, or an ultrasonic device, a navigation device, a global positioning system (GPS) receiver, an event data recorder (EDR), a flight data recorder (FDR), an automotive infotainment device, an sailing electronic device (such as a sailing navigation device or a gyro compass), avionics, security devices, vehicular head units, industrial or home robots, automatic teller machines (ATMs), point of sales (POS) devices, or Internet of Things (IoT) devices such as a light bulb, various sensors, an electric or gas meter, a sprinkler, a fire alarm, a thermostat, a street light, a toaster, fitness equipment, a hot water tank, a heater, or a boiler.

According to various embodiments of the disclosure, the electronic device may be at least one of part of furniture or building/structure, an electronic board, an electronic signature receiving device, a projector, or various measurement devices such as devices for measuring water, electricity, gas, or electromagnetic waves. The electronic device may be one or a combination of the above-listed devices, and may be a flexible electronic device. The electronic device disclosed herein is not limited to the above-listed devices, and also includes new electronic devices to be developed.

Hereinafter, the wearable electronic device is referred to as an electronic device 901. As used herein, the term "user" may denote a human or another device, such as an artificial intelligence electronic device, using the electronic device.

Referring to FIG. 76, an electronic device 901 is included in a network environment 900 and includes a bus 905, a processor 906, a memory 907, a sensor unit 920, and a communication interface 911. In some embodiments, the electronic device 901 may exclude at least one of the components or may add another component.

The bus 905 includes a circuit for connecting the components 905 to 911 with one another and transferring communications such as control messages and/or data between the components.

The processing module 906 includes one or more of a central processing unit (CPU), an application processor (AP), and a communication processor (CP). The processor 906 performs control on at least one of the other components of the electronic device 901, and/or performs an operation or data processing relating to communication.

The memory 907 includes a volatile and/or non-volatile memory, and stores commands or data related to at least one other component of the electronic device 901. The memory 907 stores electrical signal values by the biomarker, and stores software and/or a program 908. The program 908 includes a kernel 913, middleware 914, an application programming interface (API) 915, and/or application programs (or "applications") 916. At least a portion of the kernel 913, middleware 914, or API 915 may be denoted an operating system (OS).

For example, the kernel 913 controls or manages system resources used to perform operations or functions implemented in other programs. The kernel 913 provides an interface that allows the middleware 914, the API 915, or the applications 916 to access the individual components of the electronic device 901 to control or manage the system resources.

The middleware 914 functions as a relay to allow the API 915 or the applications 916 to communicate data with the kernel 913, for example. A plurality of applications 916 is provided. The middleware 914 controls work requests received from the applications 916, such as by allocation the priority of using the system resources of the electronic device 901 to at least one of the plurality of applications 134.

The API 915 allows the applications 916 to control functions provided from the kernel 913 or the middleware 914. For example, the API 133 includes at least one interface or function for filing control, window control, image processing or text control.

The sensor unit 920 detects a biomarker from the body fluid, and detects a bio signal by the biomarker or a bio signal, such as electrocardiogram (ECG), generated from the user's body.

The communication interface 911 establishes short-range communication 918 with an external electronic device 902, such as Bluetooth (BT) or near-field communication (NFC). The electronic device transfers an electrical signal value by the biomarker, to the first external electronic device 902 through the short-range communication 918. The first external electronic device 902 transfers the biomarker to the second external electronic device 903 or server 904 through the network 917.

The communication interface 911 establishes communication between the electronic device 901 and an external electronic device. For example, the communication interface 911 is connected with the network 917 through wireless or wired communication to communicate with the external electronic device to transfer the bio signal value obtained by measuring the concentration of the detected biomarker to the external device.

The wireless communication uses at least one of long term evolution (LTE), long term evolution-advanced (LTE-A), code division multiple access (CDMA), wideband code division multiple access (WCDMA), universal mobile telecommunication system (UMTS), wireless broadband (Wi-Bro), or global system for mobile communication (GSM), as a cellular communication protocol. The wired connection includes at least one of universal serial bus (USB), high definition multimedia interface (HDMI), recommended standard 232 (RS-232), or plain old telephone service (POTS). The network 917 includes at least one of a local area network (LAN) or wide area network (WAN), Internet, or a telephone network.

The first and second external electronic devices 902 and 903 may be the same or a different type than the electronic device 901. The server 904 includes a group of one or more servers. According to an embodiment of the present disclosure, all or some of operations executed on the electronic device 901 may be executed on another or multiple other electronic devices. When the electronic device 901 should perform some function or service automatically or at a request, the electronic device 901, instead of executing the function or service on its own or additionally, requests another device, such as electronic devices 902 and 903 or server 904, to perform at least some functions associated therewith. The other electronic device may execute the requested functions or additional functions and transfer a result of the execution to the electronic device 901, which provides a requested function or service by processing the received result as-is or in addition to another execution. To that end, a cloud computing, distributed computing, or client-server computing technique may be used, for example.

According to an embodiment of the present disclosure, the electronic device includes an input/output interface and a display.

The input/output interface transfers commands or data input from a user or other external devices to other component(s) of the electronic device 901, and outputs commands or data received from other component(s) of the electronic device 901 to the user or the other external device.

The display may be a liquid crystal display (LCD), a light emitting diode (LED) display, an organic light emitting diode (OLED) display, or a microelectromechanical systems (MEMS) display, or an electronic paper display. The display displays various contents, such as text, images, videos, icons, or symbols, to the user. The display includes a touchscreen and receives a touch, gesture, proximity or hovering input using an electronic pen or a body portion of the user.

Figure 77:
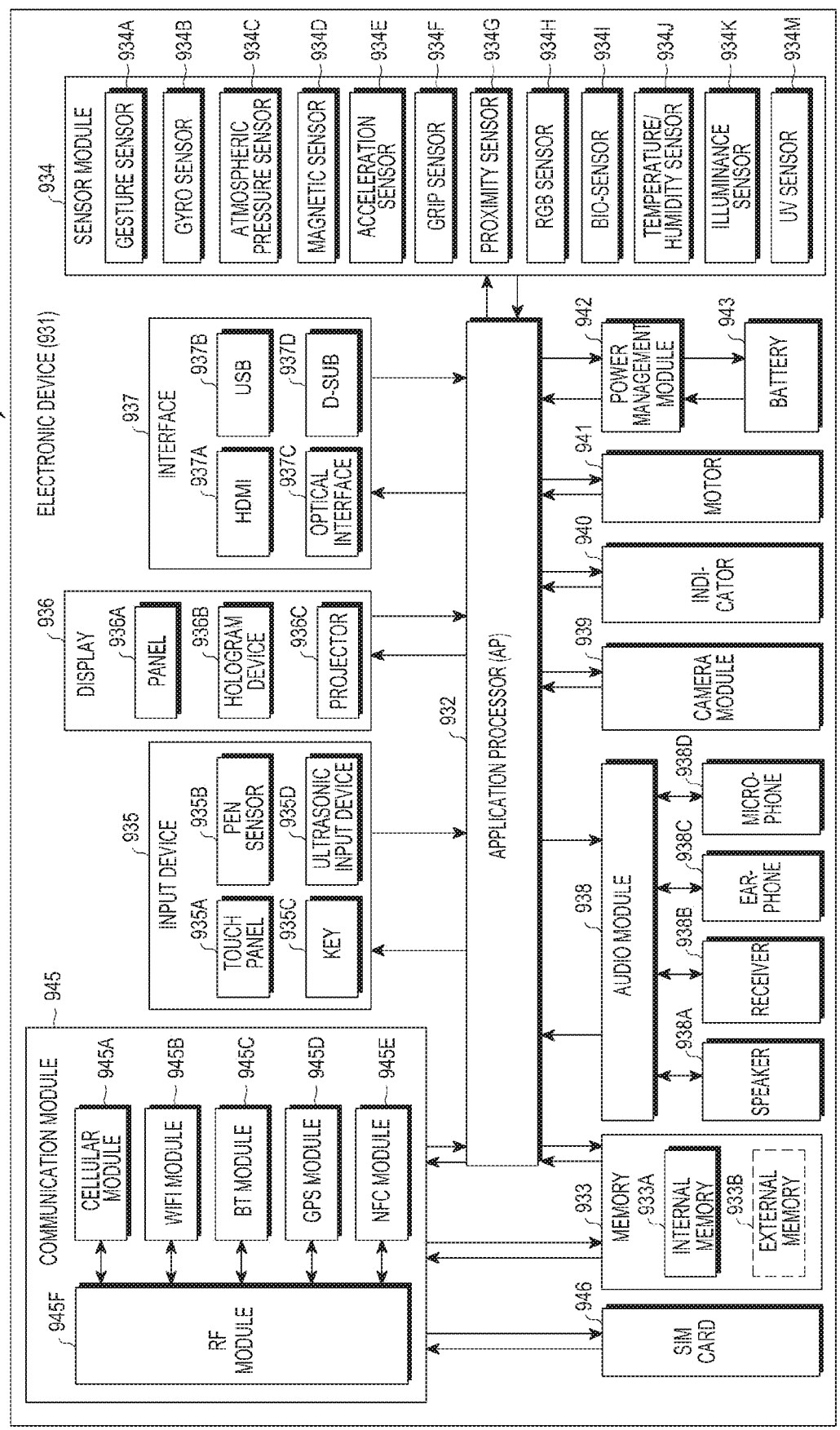
FIG. 77 is a block diagram illustrating a wearable electronic device according to an embodiment of the present disclosure.

FIG. 77 is a block diagram 930 illustrating an electronic device 931 according to an embodiment of the present disclosure. The electronic device 931 includes the entire or part of the configuration of, such as the electronic device 902 and 903 shown in FIG. 76. The electronic device 931 includes one or more application processors (APs) 932, a communication module 945, a subscriber identification module (SIM) card 946, a memory 933, a sensor module 934, an input device 935, a display 936, an interface 937, an audio module 938, a camera module 939, a power management module 942, a battery 943, an indicator 940, and a motor 941.

The AP 932 controls multiple hardware and software components connected to the AP 932 by running an operating system or application programs, and the AP 932 processes and computes various data.

The AP 932 performs a computing process for generating bio information using bio signal values by a biomarker detected from a body fluid. The AP 932 may be implemented in a system on chip (SoC) and may further include a graphic processing unit (GPU) and/or an image signal processor. The AP 932 includes at least some of the components shown in FIG. 77. The AP 932 loads a command or data received from at least one of other components, such as a non-volatile memory, on a volatile memory, processes the command or data, and stores various data in the non-volatile memory. The communication module 945 includes the same or similar configuration to the communication interface 911 of FIG. 76. The communication module 945 includes a cellular module 945A, a wireless fidelity (Wi-Fi) module 945B, a Bluetooth (BT) module 945C, a global positioning system (GPS) module 945D, a near-field communication (NFC) module 945E, and a radio frequency (RF) module 945F.

The cellular module 945A provides voice call, video call, text, or Internet services through a communication network and performs identification or authentication on the electronic device 931 in the communication network using the SIM card 946. The cellular module 945A performs at least some of the functions provided by the AP 932, and includes a communication processor (CP).

The Wi-Fi module 945B, the BT module 945C, the GPS module 945D, and the NFC module 945E include a process for processing data communicated through the module. At least two of the cellular module 945A, the Wi-Fi module 945B, the BT module 945C, the GPS module 945D, and the NFC module 945E may be included in a single integrated circuit (IC) or an IC package.

The RF module 945F communicates RF signals and includes, for example, a transceiver, a power amp module (PAM), a frequency filter, a low noise amplifier (LNA), and an antenna. At least one of the cellular module 945A, the Wi-Fi module 945B, the BT module 945C, the GPS module 945D, and the NFC module 945E communicate RF signals through a separate RF module.

The SIM card 946 includes a subscriber identification module and/or an embedded SIM, and may contain unique identification information, such as an integrated circuit card identifier (ICCID) or subscriber information, such as an international mobile subscriber identity (IMSI).

The memory 933 includes an internal memory 933A and may include an external memory 933B. The internal memory 933A includes at least one of a volatile memory, such as a dynamic random access memory (DRAM), a static RAM (SRAM), or a synchronous dynamic RAM (SDRAM), and a non-volatile memory, such as a one-time programmable read only memory (OTPROM), a programmable ROM (PROM), an erasable and programmable ROM (EPROM), an electrically erasable and programmable ROM (EEPROM), a mask ROM, a flash ROM, a flash memory such as a NAND or a NOR flash, a hard drive, or solid state drive (SSD). The external memory 933B includes a flash drive, such as a compact flash (CF) memory, a secure digital (SD) memory, a micro-SD memory, a min-SD memory, an extreme digital (xD) memory, or a Memory Stick™. The external memory 933B may be functionally and/or physically connected with the electronic device 931 via various interfaces.

For example, the sensor module 934 measures a physical quantity or detects an operational state of the electronic device 931, and the sensor module 940 converts the measured or detected information into an electrical signal. The sensor module 934 includes at least one of a gesture sensor 934A, a gyro sensor 934B, an air pressure sensor 934C, a magnetic sensor 934D, an acceleration sensor 934E, a grip sensor 934F, a proximity sensor 934G, a color sensor 934H such as a red-green-blue (RGB) sensor, a bio sensor 934I, a temperature/humidity sensor 934J, an illumination sensor 934K, or an ultra violet (UV) sensor 934M.

Additionally or alternatively, the sensing module 934 includes an E-nose sensor, an electromyography (EMG) sensor, an electroencephalogram (EEG) sensor, an electrocardiogram (ECG) sensor, an infrared (IR) sensor, an iris sensor, or a finger print sensor, for example. The sensor module 934 may further include a control circuit for controlling at least one or more of the sensors included in the sensing module. The electronic device 931 may further include a processor configured to control the sensor module 934 as part of or separately from the AP 932, and the electronic device 931 controls the sensor module 934 while the AP is in a sleep mode.

The input unit 935 includes a touch panel 935A, a (digital) pen sensor 935B, a key 935C, and an ultrasonic input device 935D. The touch panel 935A uses at least one of capacitive, resistive, infrared, or ultrasonic methods, and further includes a control circuit and a tactile layer that provides a user with a tactile reaction.

The (digital) pen sensor 935B may be part of a touch panel or a separate sheet for recognition. The key 935C includes a physical button, optical key or key pad. The ultrasonic input device 935D uses an input tool that generates an ultrasonic signal and enable the electronic device 931 to identify data by sensing the ultrasonic signal to a microphone 938D.

The display 936 includes a panel 936A, a hologram device 936B, and a projector 936C. The panel 936A may be implemented to be flexible, transparent, or wearable, and may be incorporated with the touch panel 935A in a module. The hologram device 936B provides three dimensional (3D) images (holograms) in the air by using light interference. The projector 936C displays an image by projecting light onto a screen that is located inside or outside of the electronic device 931. The display 936 may further include a control circuit to control the panel 936A, the hologram device 936B, and the projector 936C.

The interface 937 includes a high definition multimedia Interface (HDMI) 937A, a universal serial bus (USB) 937B, an optical interface 937C, and a D-subminiature (D-sub) 937D. The interface 937 performs a function similar to the communication interface 811 shown in FIG. 76. Additionally or alternatively, the interface 937 includes a mobile high-definition link (MHL) interface, a secure digital (SD) card/multimedia card (MMC) interface, or IrDA standard interface.

The audio module 938 converts a sound into an electric signal or vice versa, for example. At least some components of the audio module 938 may process sound information input or output through a speaker 938A, a receiver 938B, an earphone 938C, or the microphone 938D.

For example, the camera module 939 captures still images and videos, and includes, one or more image sensors such as front and back sensors, a lens, an Image Signal Processor (ISP), or a flash such as an LED or xenon lamp.

The power manager module 942 manages power of the electronic device 931. Although not shown, the power manager module 942 includes a power management integrated circuit (PMIC), a charger IC, or a battery gauge. The PMIC includes a wired and/or wireless recharging scheme. The wireless charging scheme includes a magnetic resonance scheme, a magnetic induction scheme, or an electromagnetic wave based scheme, and an additional circuit, such as a coil loop, a resonance circuit, or a rectifier may be added for wireless charging. The battery gauge measures an amount of remaining power of the battery 943, a voltage, a current, or a temperature while the battery 943 is being charged. The battery 943 is a rechargeable battery or a solar battery.

The indicator 940 indicates a particular state of the electronic device 931 or a part of the electronic device, including such as a booting state, a message state, or recharging state. The motor 941 converts an electric signal to a mechanical vibration and generates a vibrational or haptic effect. A processing unit for supporting mobile TV, such as a GPU may be included in the electronic device 931 to process media data conforming to a standard for Digital Multimedia Broadcasting (DMB), Digital Video Broadcasting (DVB), or mediaFLO™.

Each of the aforementioned components of the electronic device includes one or more parts, and a name of the part may vary with a type of the electronic device. The electronic device in accordance with various embodiments of the present disclosure includes at least one of the aforementioned components, omits some of the components, or includes other additional component(s). Some of the components may be combined into an entity, but the entity may perform the same functions as the components perform.

Figure 78:
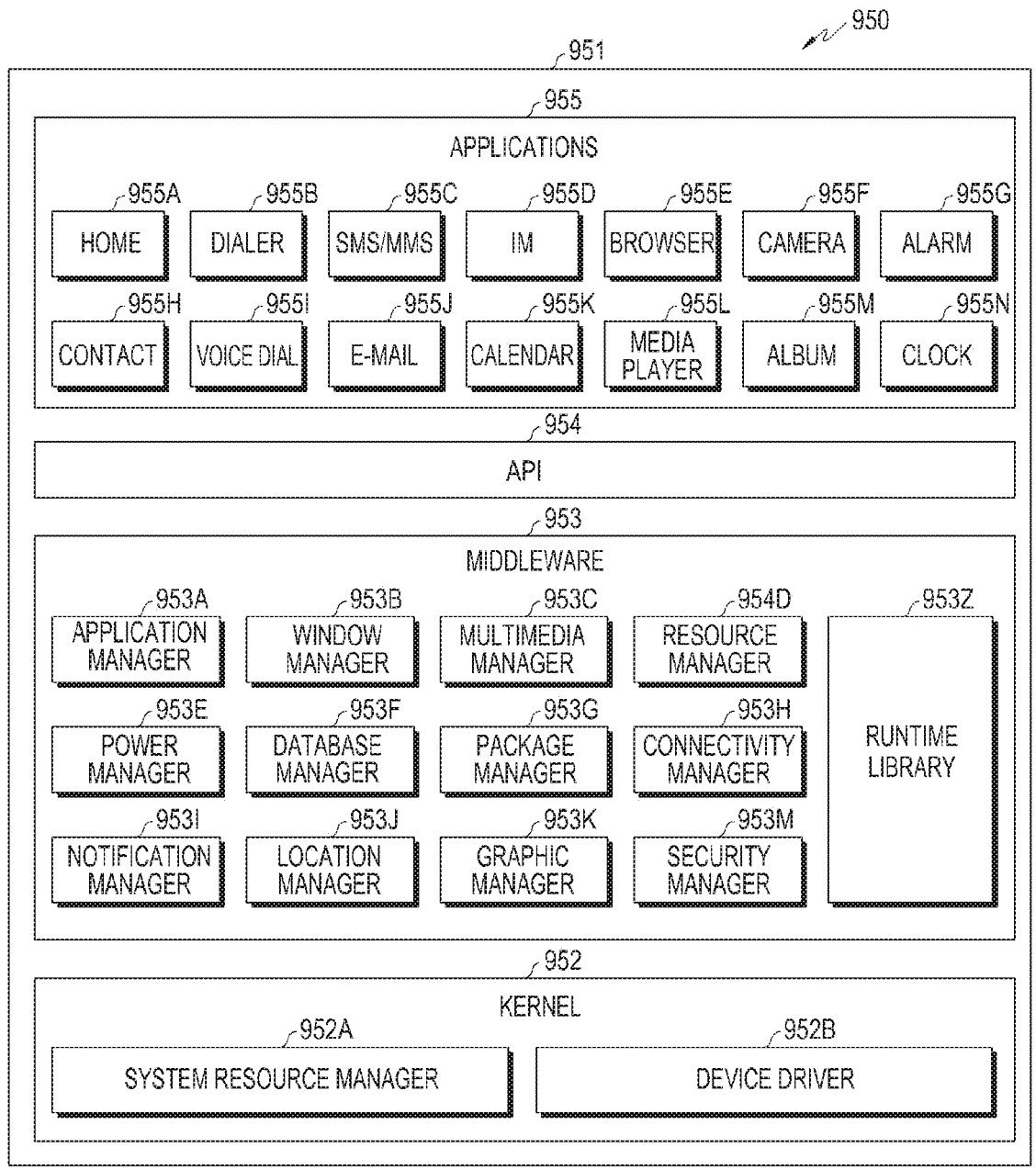
FIG. 78 is a block diagram illustrating a program module according to an embodiment of the present disclosure.

FIG. 78 is a block diagram 950 illustrating a program module 951 according to an embodiment of the present disclosure. The program module 951 includes an operating system (OS) controlling resources related to the electronic device and/or various applications driven on the operating system. The operating system may be Android, iOS, Windows, Symbian, Tizen, or Bada.

The program 951 includes a kernel 952, middleware 953, an application programming interface (API) 954, and/or applications 955. At least a part of the program module 951 may be preloaded on the electronic device or may be downloaded from a server.

The kernel 952 includes a system resource manager 952A and a device driver 952B. The system resource manager 952A may perform control, allocation, or recovery of system resources and includes a process managing unit, a memory managing unit, or a file system managing unit. The device driver 952B includes a display driver, a camera driver, a Bluetooth driver, a shared memory driver, a USB driver, a keypad driver, a Wi-Fi driver, an audio driver, or an inter-process communication (IPC) driver.

The middleware 953 provides various functions to the application 955 through the API 954 so that the application 955 may efficiently use limited system resources in the electronic device or provides functions jointly required by the applications 955. The middleware 953 includes at least one of a runtime library 953Z, an application manager 953A, a window manager 953B, a multimedia manager 953C, a resource manager 953D, a power manager 953E, a database manager 953F, a package manager 953G, a connectivity manager 953H, a notification manager 953I, a location manager 953J, a graphic manager 953K, and a security manager 953M.

The runtime library 953Z includes a library module used by a compiler in order to add a new function through a programming language while at least one of the applications 955 is being executed. The runtime library 953Z may perform input/output management, memory management, or operation on arithmetic functions.

The application manager 953A manage the life cycle of at least one of the applications 955. The window manager 953B manages GUI resources used on the screen. The multimedia manager 953C procures formats necessary to play various media files and uses a codec appropriate for a format to perform encoding or decoding on media files. The resource manager 953D manages resources, such as source code of at least one of the applications 955, memory or storage space.

The power manager 953E operates together with a basic input/output system (BIOS) to manage battery or power and provide power information necessary for operating the electronic device. The database manager 953F generates, searches, or varis a database to be used in at least one of the applications 955. The package manager 953G manages installation or update of an application that is distributed in the form of a package file.

The connectivity manager 953H manages wireless connectivity, such Wi-Fi or Bluetooth. The notification manager 953I displays or notifies an event, such as a coming message, appointment, or proximity notification, of the user without interfering with the user. The location manager 953J manages locational information on the electronic device. The graphic manager 953K manages graphic effects to be offered to the user and their related user interface. The security manager 352 provides various security functions necessary for system security or user authentication. When the electronic device has telephony capability, the middleware 953 may further include a telephony manager for managing voice call or video call functions of the electronic device.

The middleware 953 includes a middleware module forming a combination of various functions of the above-described components. The middleware 953 provides a specified module per type of the operating system in order to provide a differentiated function. The middleware 953 may dynamically omit some existing components or add new components.

The API 954 may be a set of API programming functions and includes different configurations depending on operating systems. For example, in the case of Android or iOS, one API set is provided per platform, and in the case of Tizen, two or more API sets may be offered per platform.

The applications 955 provide functions such as a home 955A, a dialer 955B, an SMS/MMS 955C, an instant message (IM) 955D, a browser 955E, a camera 955F, an alarm 955G, a contact 955H, a voice dial 955I, an email 955J, a calendar 955K, a media player 955L, an album 955M, and a clock 955N function, as well as a health-care application measuring the degree of workout or blood sugar, or provision of environmental information such as air pressure, moisture, or temperature information.

According to an embodiment of the present disclosure, the applications 955 include an information exchanging application supporting information exchange between the electronic device and an external electronic device. Examples of the information exchange application include, but are not limited to, a notification relay application for transferring specific information to the external electronic device, and a device management application for managing the external electronic device.

For example, the notification relay application includes a function for relaying notification information generated from other applications of the electronic device, such as short messaging service/multimedia messaging service (SMS/MMS), email, health-care, or environmental information applications to the external electronic device. The notification relay application receives notification information from the external electronic device and provides the received notification information to the user. The application may interwork with a hospital or medical center to transfer a bio signal by a biomarker or bio information obtained by analyzing a bio signal value to a medical doctor. The medical doctor may diagnose the patient's condition through the bio signal or bio information. The application transfers the result of the diagnosis by the medical doctor to the user.

The device management application performs at least one function of the external electronic device communicating with the electronic device, such as turning on/off the external electronic device or some components of the external electronic device or control of brightness or resolution) of the display, and the device management application manages an application operating in the external electronic device or a service provided from the external electronic device.

According to an embodiment of the present disclosure, the applications 955 include a health-care application designated depending on the attribute or the type of the electronic device, includes an application received from the external electronic device or the electronic device 902 and 903, and includes a preloaded application or a third party application downloadable from a server. The names of the components of the program module 951 according to the shown embodiment may be varied depending on the type of operating system.

According to an embodiment of the present disclosure, at least a part of the program module 951 may be implemented in software, firmware, hardware, or in a combination of two or more thereof by the AP 932 At least a part of the program module 951 includes a module, program, routine, or set of instructions or process for performing one or more functions.

The term 'module' may refer to a unit including one of hardware, software, and firmware, or a combination thereof. The term 'module' may be interchangeably used with a unit, logic, logical block, component, or circuit. The module may be one unit or part of an integrated component or part of performing one or more functions. The module may be implemented mechanically or electronically. For example, the module includes at least one of application specific integrated circuit (ASIC) chips, field programmable gate arrays (FPGAs), or programmable logic arrays (PLAs) that perform some operations, which have already been known or will be developed in the future.

According to an embodiment of the present disclosure, at least a part of the device or method may be implemented as instructions stored in a computer-readable storage medium, such as in the form of a program module. The instructions, when executed by a processor, may cause the processor to carry out a corresponding function. The computer-readable storage medium may be the memory.

The computer-readable storage medium may include a hardware device, such as hard discs, floppy discs, and magnetic tapes, optical media such as compact disc read only memories (ROMs) (CD-ROMs) and digital versatile discs (DVDs), magneto-optical media such as floptical disks, ROMs, random access memories (RAMs), flash memories, and/or the like. Examples of the program instructions include not only machine language codes but also high-level language codes which are executable by various computing means using an interpreter. The aforementioned hardware devices may be configured to operate as one or more software modules to carry out exemplary embodiments of the present disclosure, and vice versa.

Modules or programming modules in accordance with various embodiments of the present disclosure includes at least one or more of the aforementioned components, omit some of them, or further include other additional components. Operations performed by modules, programming modules or other components in accordance with various embodiments of the present disclosure may be carried out sequentially, simultaneously, repeatedly, or heuristically. Furthermore, some of the operations may be performed in a different order, or omitted, or include other additional operation(s).

As described above, a wearable electronic device includes a main body wearable on a human body, a circuit unit mounted on the body unit, and a receiving unit provided in the main body and receiving a sensor unit contacting the human body to measure a bio signal, the sensor unit is detachably coupled to the body unit.

The wearable electronic device includes a battery mounted in the main body to supply power to the circuit unit and a cover unit fastening the sensor unit received in the receiving unit.

The cover unit is hinged to the main body and rotate.

The sensor unit is disposed between the battery and the circuit unit.

The main body includes a first main body where the circuit unit is mounted, a second main body where the battery is mounted, and a third main body where the sensor unit is mounted, the first main body and the second main body include a cover guide unit guiding each of two opposite ends of the cover unit, and the cover unit may slide along the cover guide unit to open and close the receiving unit.

The cover unit includes a sensor guide unit corresponding to two opposite ends of the sensor unit, and the sensor unit may slide along the sensor guide unit to be coupled with the cover unit.

The main body includes a plurality of sensor units arranged therein, and the cover unit includes contact terminals electrically connected with the plurality of sensor units.

The plurality of sensor units each detects the same biomarker and transfer a bio signal by the biomarker to the circuit unit, and the circuit unit compares the concentration of the biomarker through the bio signals received from the sensor units.

The plurality of sensor units detects different biomarkers or measure different bio signals. For example, the sensor units are formed of sensors, such as a blood sugar and lactic acid sensor, measuring different biomarkers and includes an optic sensor for measuring body temperature.

The sensor unit includes connection holes corresponding to at least one of the contact terminals, and the circuit unit determines the type of the sensor unit depending on the contact terminals inserted into the connection holes or a combination of the contact terminals.

The circuit unit determines the type of the sensor unit mounted in the main body depending on whether each of the contact terminals is electrically connected with any one of the connection holes.

The sensor unit includes a contact pad electrically connected with at least a pair of contact terminals of the contact terminals, and the circuit unit determines the type of the sensor unit mounted in the main body depending on a combination of the contact terminals electrically connected through the contact pad.

The receiving unit includes an opening through which a rear surface of the sensor unit is partially exposed to an outside of the main body and a seating unit where another unit of the rear surface of the sensor unit is seated.

The sensor unit includes micro needles.

The sensor unit measures at least one of glucose, lactic acid, body temperature, blood pressure, skin conductivity, heartbeat, and ECG.

A wearable electronic device includes a main body wearable on a human body and a sensor unit provided in the main body and contacting a human body to measure a bio signal, the sensor unit includes a working electrode, a counter electrode electrically connected with the working electrode, and a reference electrode electrically connected with the working electrode. The sensor unit measures a bio signal by varying a voltage between the reference electrode and the working electrode.

The wearable electronic device includes a controller adjusting the voltage between the reference electrode and the working electrode to vary the voltage between the reference electrode and the working electrode.

Each of the working electrode, the counter electrode, and the reference electrode is formed of a micro needle.

A plurality of the working electrodes is provided, the counter electrode is connected with each of the working electrodes, and the reference electrode apply a different voltage to each of the working electrodes.

A wearable electronic device includes a main body wearable on a human body, a sensor unit provided in the main body and including micro needles, and an attaching device attaching the sensor unit to a human body, the attaching device includes a housing, a moving unit moving back and forth in the housing, a hooking unit provided in the housing and detachably coupled with the moving unit, a first elastic unit provided between the moving unit and the hooking unit to provide an elastic force to the moving unit, a button unit releasing a coupling between the hooking unit and the moving unit, a receiving unit provided in the moving unit and receiving the body unit, and a coupling unit provided in the moving unit and detachably coupled with the body unit.

The housing includes a first guide unit formed along a longitudinal direction of the housing and guiding a movement of the moving unit.

The moving unit includes a second guide unit corresponding to the first guide unit.

The housing includes a first hole where the button unit is inserted.

The button unit includes a first button unit moved along the first hole by an external force, a second button unit projecting along a side surface of the first button unit, and a third button unit projecting from a bottom of the first button unit and having a unit formed to be inclined.

The hooking unit includes a first hooking unit, a first protrusion projecting from the first hooking unit, a second hooking unit formed to be symmetrical with the first hooking unit, a second protrusion projecting from the second hooking unit, a second elastic unit provided between the first hooking unit and the second hooking unit, and an inclined hole formed in each of the first hooking unit and the second hooking unit and having an inclined surface corresponding to the third button unit, the first hooking unit and the second hooking unit approaching each other as the third button unit is inserted into the inclined hole, and the first hooking unit and the second hooking unit separating from each other as the third button unit departs from the inclined hole.

The housing includes a first hooking hole and a second hooking hole respectively corresponding to the first protrusion and the second protrusion, and the first protrusion and the second protrusion is locked are bound to the first hooking hole and the second hooking hole, respectively, as the first hooking unit and the second hooking unit are separate from each other.

The main body includes a first body unit, a second main body detachably coupled with the first body unit, and a coupling hole formed in any one of a side surface of the first main body or a side surface of the second main body and coupled with the coupling unit.

The coupling hole is formed along a periphery of any one of the side surface of the first main body or the side surface of the second body unit.

The coupling unit includes first rotating holes formed in the moving unit, a rotating unit provided between the first rotating holes and having second rotating holes, a rotating shaft inserted between the first rotating holes and the second rotating holes, and a fixing unit projecting from the rotating unit and detachably coupled with the coupling hole as the rotating unit rotates.

An inner wall of the housing includes an inclined surface formed to be partially inclined, the rotating unit may be rotated toward the inclined surface by an elastic force of the third elastic unit, and the fixing unit leaves the coupling hole as the rotating unit rotates.

The moving unit moves back and forth along a second hole formed in a side surface of the housing.

The main body is coupled with the coupling unit as the body unit, together with the moving unit, is moved in a first direction while received in the moving unit, the first elastic unit may accumulate an elastic force as the moving unit moves, the moving unit moves in the first direction to be coupled with the hooking unit, the button unit may release a coupling between the hooking unit and the moving unit, the moving unit may be accelerated in a second direction, which is an opposite direction of the first direction, by the elastic force of the first elastic unit, and as the main body is released from the coupling unit while the body unit, together with the moving unit, may be accelerated in the second direction, the main body moves to an outside of the moving unit.

In the wearable electronic device, the sensor unit is detachably coupled to the body unit, so that the sensor unit may be replaced with a new sensor unit when its lifetime expires while the circuit unit mounted in the main body may be continuously used.

In the wearable electronic device, the sensor unit is detachably coupled to the body unit, enabling replacement of a sensor unit for measuring blood sugar with a sensor unit for measuring various bio signals, such as body temperature.

Further in the wearable electronic device, various bio information is measured as the voltage between reference electrode and working electrode varies.

The wearable electronic device includes the attaching device for attaching the sensor unit with micro needles to the human body, allowing easier insertion of the micro needles into the human body.

While the present disclosure has been shown and described with reference to exemplary embodiments thereof, it will be apparent to those of ordinary skill in the art that various changes in form and detail may be made thereto without departing from the spirit and scope of the present disclosure as defined by the following claims.

What is claimed is:

1. A wearable electronic device, comprising:
a main body wearable on a human body and including a cover unit;
a circuit unit mounted on the main body; and
a sensor unit configured to contact the human body to measure a bio signal,
wherein the sensor unit is received in a receiving unit provided in the main body and is detachably coupled to the main body,
wherein the cover unit is configured to open the receiving unit by a rotation and to detach the sensor unit from the main body by the rotation,
wherein the receiving unit includes an opening through which a first portion of a rear surface of the sensor unit is exposed to an outside of the main body and a seating unit where a second portion of the rear surface of the sensor unit is seated, and
wherein the cover unit is configured to fasten the sensor unit in the receiving unit.

2. The wearable electronic device of claim 1, further comprising:
a battery mounted in the main body and configured to supply power to the circuit unit.

3. The wearable electronic device of claim 2, wherein the cover unit includes a sensor guide unit that engages two opposite ends of the sensor unit, and
wherein the sensor unit is configured to slide along the sensor guide unit to be coupled with the cover unit.

4. The wearable electronic device of claim 2, wherein a plurality of sensor units are arranged in the main body, and
wherein the at least one contact terminal is composed of a plurality of contact terminals that are electrically connected with the plurality of sensor units, respectively.

5. The wearable electronic device of claim 4, wherein the sensor unit includes connection holes into which at least one of the contact terminals is configured to be inserted, and
wherein the circuit unit is configured to determine a type of the sensor unit depending on the contact terminals inserted into the connection holes or a combination of the contact terminals.

6. The wearable electronic device of claim 4, wherein the sensor unit includes a contact pad electrically connected with at least two of the contact terminals, and
wherein the circuit unit is configured to determine a type of the sensor unit mounted in the main body depending on a combination of the contact terminals electrically connected through the contact pad.

7. A wearable electronic device, comprising:
a main body wearable on a human body and including a cover unit; and
a sensor unit provided in the main body and configured to contact the human body to measure a bio signal, the sensor unit being in a receiving unit provided in the main body and being detachably coupled to the main body,
wherein the cover unit is configured to open the receiving unit by a rotation and to detach the sensor unit from the main body by the rotation,
wherein the sensor unit includes a working electrode, a counter electrode electrically connected with the working electrode, and a reference electrode electrically connected with the working electrode, wherein the sensor unit is configured to measure the bio signal by varying a voltage between the reference electrode and the working electrode, wherein the receiving unit includes an opening through which a first portion of a rear surface of the sensor unit is exposed to an outside of the main body and a seating unit where a second portion of the rear surface of the sensor unit is seated, and wherein the cover unit is configured to fasten the sensor unit in the receiving unit.

8. The wearable electronic device of claim 7, further comprising a controller configured to adjust the voltage between the reference electrode and the working electrode to vary the voltage between the reference electrode and the working electrode.

9. The wearable electronic device of claim 7, wherein a plurality of the working electrode is provided, wherein the counter electrode is connected with each of the working electrodes, and wherein the reference electrode is configured to apply a different voltage to each of the working electrodes.

10. A wearable electronic device, comprising:

a main body wearable on a human body;

a sensor unit provided in the main body and including micro needles; and an attaching device configured to attach the sensor unit to the human body, wherein the attaching device includes a housing, a moving unit that is configured to move back and forth in the housing, a hooking unit provided in the housing and detachably coupled with the moving unit, a first elastic unit provided between the moving unit and the hooking unit to provide an elastic force to the moving unit, a button unit that releases a coupling between the hooking unit and the moving unit, a receiving unit provided in the moving unit and receiving the main body, and a coupling unit provided in the moving unit and detachably coupled with the body unit.

11. The wearable electronic device of claim 10, wherein the housing includes a first hole where the button unit is inserted.

12. The wearable electronic device of claim 11, wherein the button unit includes a first button unit that moves along the first hole by an external force, a second button unit projecting along a side surface of the first button unit, and a third button unit projecting from a bottom of the first button unit and having an inclined unit.

13. The wearable electronic device of claim 12, wherein the hooking unit includes a first hooking unit, a first protrusion projecting from the first hooking unit, a second hooking unit formed to be symmetrical with the first hooking unit, a second protrusion projecting from the second hooking unit, a second elastic unit provided between the first hooking unit and the second hooking unit, and an inclined hole formed in each of the first hooking unit and the second hooking unit and having an inclined surface corresponding to the third button unit, wherein the first hooking unit and the second hooking unit are configured to approach each other as the third button unit is inserted into the inclined hole, and wherein the first hooking unit and the second hooking unit are separated from each other as the third button unit departs from the inclined hole.

14. The wearable electronic device of claim 13, wherein the housing further includes a first hooking hole and a second hooking hole respectively corresponding to the first protrusion and the second protrusion, and wherein the first protrusion and the second protrusion are configured to lock to the first hooking hole and the second hooking hole, respectively, as the first hooking unit and the second hooking unit are separated from each other.

15. The wearable electronic device of claim 10, wherein the main body includes a first body unit, a second main body detachably coupled with the first body unit, and a coupling hole formed in any one of a side surface of the first main body and a side surface of the second main body and coupled with the coupling unit.

16. The wearable electronic device of claim 15, wherein the coupling unit includes first rotating holes formed in the moving unit, a rotating unit provided between the first rotating holes and having second rotating holes, a rotating shaft inserted between the first rotating holes and the second rotating holes, and a fixing unit projecting from the rotating unit and detachably coupled with the coupling hole as the rotating unit rotates.

17. The wearable electronic device of claim 16, wherein the main body is coupled with the coupling unit as the body unit, together with the moving unit, is moved in a first direction while received in the moving unit, wherein the first elastic unit is configured to accumulate an elastic force as the moving unit moves, wherein the moving unit is configured to move in the first direction to be coupled with the hooking unit, wherein the button unit is configured to release a coupling between the hooking unit and the moving unit, wherein the moving unit is configured to move in a second direction, which is an opposite direction of the first direction, by the elastic force of the first elastic unit, and wherein, as the main body is released from the coupling unit while the body unit, together with the moving unit, is moved in the second direction, the main body is configured to move to an outside of the moving unit.

18. The wearable electronic device of claim 1, further comprising a receiving unit provided in the main body and configured to receive the sensor unit.

19. A wearable electronic device, comprising:

a main body wearable on a human body and including a cover unit;

a circuit unit mounted on the main body; and a sensor unit configured to contact the human body to measure a bio signal, wherein the main body includes a first main body where the circuit unit is mounted, a second main body where the battery is mounted, and a third main body where the sensor unit is mounted, wherein the first main body and the second main body have a cover guide unit configured to guide each of two opposite ends of the cover unit, and wherein the cover unit is configured to slide along the cover guide unit to open and close the receiving unit.

* * * * *